US011408900B2

(12) United States Patent
Bleier et al.

(10) Patent No.: US 11,408,900 B2
(45) Date of Patent: Aug. 9, 2022

(54) SECRETED P-GLYCOPROTEIN IS A NON-INVASIVE BIOMARKER OF CHRONIC RHINOSINUSITIS

(71) Applicant: Massachusetts Eye and Ear Infirmary, Boston, MA (US)

(72) Inventors: Benjamin S. Bleier, Weston, MA (US); Angela Nocera, Boston, MA (US)

(73) Assignee: Massachusetts Eye and Ear Infirmary, Boston, MA (US)

( * ) Notice: Subject to any disclaimer, the term of this patent is extended or adjusted under 35 U.S.C. 154(b) by 183 days.

(21) Appl. No.: 16/070,053

(22) PCT Filed: Jan. 13, 2017

(86) PCT No.: PCT/US2017/013418
§ 371 (c)(1),
(2) Date: Jul. 13, 2018

(87) PCT Pub. No.: WO2017/123933
PCT Pub. Date: Jul. 20, 2017

(65) Prior Publication Data
US 2019/0086426 A1 Mar. 21, 2019

Related U.S. Application Data

(60) Provisional application No. 62/279,590, filed on Jan. 15, 2016.

(51) Int. Cl.
*G01N 33/53* (2006.01)
*G01N 33/68* (2006.01)
*A61K 9/00* (2006.01)
*A61K 45/06* (2006.01)
*A61K 31/277* (2006.01)
*A61K 31/4725* (2006.01)
*A61K 31/496* (2006.01)
*A61K 31/4164* (2006.01)
*A61K 31/4545* (2006.01)
*A61K 31/473* (2006.01)
*A61K 31/55* (2006.01)
*A61K 38/13* (2006.01)
*A61K 38/00* (2006.01)

(52) U.S. Cl.
CPC ....... *G01N 33/6893* (2013.01); *A61K 9/0043* (2013.01); *A61K 31/277* (2013.01); *A61K 31/4164* (2013.01); *A61K 31/4545* (2013.01); *A61K 31/473* (2013.01); *A61K 31/4725* (2013.01); *A61K 31/496* (2013.01); *A61K 31/55* (2013.01); *A61K 38/13* (2013.01); *A61K 45/06* (2013.01); *A61K 38/00* (2013.01); *G01N 2800/14* (2013.01)

(58) Field of Classification Search
None
See application file for complete search history.

(56) References Cited

U.S. PATENT DOCUMENTS

| 1,603,758 A | 10/1926 | Fisher |
| 1,856,811 A | 5/1932 | Inaki |
| 2,989,437 A | 6/1961 | Wruble et al. |
| 3,847,145 A | 11/1974 | Grossan |
| 5,045,694 A | 9/1991 | Beavis et al. |
| 5,118,937 A | 6/1992 | Hillenkamp et al. |
| 5,649,530 A | 7/1997 | Ballini |
| 5,719,060 A | 2/1998 | Hutchens et al. |
| 5,898,037 A | 4/1999 | Marx |
| 6,225,047 B1 | 5/2001 | Hutchens et al. |
| 6,328,718 B1 | 12/2001 | Chiang et al. |
| 6,451,815 B1 | 9/2002 | Hwang et al. |
| 6,468,798 B1 | 10/2002 | Debs et al. |
| 6,503,953 B2 | 1/2003 | Vyden |
| 6,520,284 B2 | 2/2003 | Spannbauer et al. |
| 6,579,898 B2 | 6/2003 | Humphrey |
| 6,736,792 B1 | 5/2004 | Liu |
| 6,907,879 B2 | 6/2005 | Drinan et al. |
| 7,115,565 B2 | 10/2006 | Gao et al. |
| 7,544,192 B2 | 6/2009 | Eaton et al. |
| 7,888,049 B2 | 2/2011 | Shaari |
| 7,935,731 B2 | 5/2011 | Davis |
| 8,003,106 B2 | 8/2011 | Mikayama et al. |
| 8,124,091 B2 | 2/2012 | Kato et al. |
| 8,162,921 B2 | 4/2012 | Flickinger et al. |
| 8,357,696 B2 | 1/2013 | Surber et al. |

(Continued)

FOREIGN PATENT DOCUMENTS

| CN | 101380328 | 3/2009 |
| WO | WO 01/58470 | 8/2001 |

(Continued)

OTHER PUBLICATIONS

Chiampanichayakul et al., Production of monoclonal antibodies to P-glycoprotein: its application in detection of soluble and surface P-glycoprotein of leukemia patients, Int J Hematol (2010) 92:326-333 (Year: 2010).*
Anderson, The Clinical Plasma Proteome: A Survey of Clinical Assays for Proteins in Plasma and Serum, Clinical Chemistry, 56:2, 177-185 (2010) (Year: 2010).*
Van Der Vekiens et al., Human and equine cardiovascular endocrinology: beware to compare, Cardiovascular Endocrinology 2013, vol. 2, No. 4, pp. 67-76 (Year: 2013).*
Torzewski et al., Animal Models of C-Reactive Protein, Hindawl Publishing Corporation, Mediators of Inflammation, vol. 2014, Article ID 683598, 2014, pp. 1-7. (Year: 2014).*
Akdis et al., "Endotypes and phenotypes of chronic rhinosinusitis: a PRACTALL document of the European Academy of Allergy and Clinical Immunology and the American Academy of Allergy, Asthma & Immunology," J Allergy Clin Immunol, 2013,131(6):1479-90.
Amin, "P-glycoprotein Inhibition for Optimal Drug Delivery," Drug Target Insights, 2013, 7:27-34.

(Continued)

*Primary Examiner* — Gary Counts
(74) *Attorney, Agent, or Firm* — Fish & Richardson P.C.

(57) ABSTRACT

Methods for identifying and optionally treating subjects, e.g., subjects who have Chronic Rhinosinusitis (CRS), based on the detection of elevated levels of soluble P-glycoprotein in nasal secretions. The methods of treatment can include administration of a therapeutically effective amount of a P-glycoprotein inhibitor.

16 Claims, 17 Drawing Sheets

(56) References Cited

U.S. PATENT DOCUMENTS

| | | |
|---|---|---|
| 8,637,469 B2 | 1/2014 | Levitt |
| 8,980,848 B2 | 3/2015 | Chan et al. |
| 9,744,210 B2 | 8/2017 | Bleier |
| 10,653,745 B2 | 5/2020 | Bleier |
| 11,007,246 B2 | 5/2021 | Bleier |
| 2003/0180815 A1 | 9/2003 | Rawson et al. |
| 2004/0166110 A1 | 8/2004 | Mechetner et al. |
| 2005/0245906 A1 | 11/2005 | Makower et al. |
| 2006/0051300 A1 | 3/2006 | Chaudry |
| 2006/0134009 A1 | 6/2006 | Deaver et al. |
| 2006/0275920 A1 | 12/2006 | Petrilla et al. |
| 2006/0276743 A1 | 12/2006 | MacMahon et al. |
| 2007/0015719 A1 | 1/2007 | Jenkins et al. |
| 2007/0020299 A1 | 1/2007 | Pipkin et al. |
| 2007/0105237 A1 | 5/2007 | Corstjens et al. |
| 2007/0178526 A1 | 8/2007 | Kountakis et al. |
| 2007/0226012 A1 | 9/2007 | Salgado et al. |
| 2008/0081341 A1 | 4/2008 | Maher et al. |
| 2008/0118925 A1 | 5/2008 | Cuppens et al. |
| 2008/0160538 A1 | 7/2008 | Saul et al. |
| 2008/0199522 A1 | 8/2008 | Sawada et al. |
| 2008/0221507 A1 | 9/2008 | Hoke et al. |
| 2009/0202665 A1 | 8/2009 | Javer et al. |
| 2009/0246886 A1 | 10/2009 | Buck |
| 2010/0016267 A1 | 1/2010 | Theeuwes et al. |
| 2010/0024530 A1 | 2/2010 | Hopkins |
| 2010/0129316 A1 | 5/2010 | Levitt |
| 2010/0285610 A1 | 11/2010 | Saul et al. |
| 2011/0118199 A1 | 5/2011 | Dormeyer |
| 2011/0240012 A1 | 10/2011 | Pilon |
| 2012/0095019 A1 | 4/2012 | Sinha et al. |
| 2012/0219565 A1 | 8/2012 | Presta |
| 2012/0240930 A1 | 9/2012 | Kristensson et al. |
| 2013/0059399 A9 | 3/2013 | Saul et al. |
| 2013/0189794 A1 | 7/2013 | Emeric et al. |
| 2013/0295691 A1 | 11/2013 | Saul |
| 2014/0093880 A1* | 4/2014 | Kim .............. C12Q 1/6886 435/6.12 |
| 2014/0206100 A1 | 7/2014 | Saul |
| 2014/0336463 A1 | 11/2014 | Shikani |
| 2014/0370616 A1 | 12/2014 | Gupta et al. |
| 2015/0017099 A1 | 1/2015 | Cohen et al. |
| 2017/0128659 A1 | 5/2017 | Mehta |
| 2018/0104253 A1 | 4/2018 | Yadidi et al. |
| 2020/0197481 A1 | 6/2020 | Bleier |
| 2021/0330737 A1 | 10/2021 | Bleier |

FOREIGN PATENT DOCUMENTS

| | | | |
|---|---|---|---|
| WO | WO 2005/072704 | 8/2005 | |
| WO | WO 2006/051206 | 5/2006 | |
| WO | WO 2008/058160 | 5/2008 | |
| WO | WO 2009/140715 | 11/2009 | |
| WO | WO-2009140715 A1 * | 11/2009 | ............ G01N 33/569 |
| WO | WO 2012/006599 | 1/2012 | |
| WO | WO 2014/106021 | 7/2014 | |
| WO | WO-2014106021 A1 * | 7/2014 | ......... A61K 31/4164 |
| WO | WO 2019/139901 | 7/2019 | |
| WO | WO 2020/198232 | 10/2020 | |

OTHER PUBLICATIONS

Bebawy et al., "Membrane microparticles mediate transfer of P-glycoprotein to drug sensitive cancer cells," Leukemia, 2009, 23:1643-1649.

Bleier et al., "P-glycoprotein functions as an immunomodulator in healthy human primary nasal epithelial cells," Int Forum Allergy Rhinol, 2013, 3 (6):433-8.

Bleier et al., "P-glycoprotein promotes epithelial T helper 2-associated cytokine secretion in chronic sinusitis with nasal polyps," Int Forum Allergy Rhinol, 2014, 4 (6):488-94.

Bleier et al., "P-glycoprotein regulates *Staphylococcus aureus* enterotoxin B-stimulated interleukin-5 and thymic stromal lymphopoietin secretion in organotypic mucosal explants," Int Forum Allergy Rhinol, 2016, 6(2):169-77.

Bleier et al., "Primary human sinonasal epithelial cell culture model for topical drug delivery in patients with chronic rhinosinusitis with nasal polyposis," J. Pharm. Pharmacol, 2012, 64:449-56.

Bleier et al., "Verapamil modulates interleukin-5 and interleukin-6 secretion in organotypic human sinonasal polyp explants," Int Forum Allergy Rhinol, 2014, 5 (1):10-13.

Bleier, "P-glycoprotein and Epithelial Cell Function," Slideshow Presented at Federation of Clinical Immunology Societies, San Diego, CA, 2015, 24 pages.

Bleier, "P-glycoprotein in Epithelial Cell Function," Federation of Clinical Immunology Societies, Scientific Program, San Diego, CA, 2015, p. 8.

Bleier, "Regional expression of epithelial MDR1/P-glycoprotein in chronic rhinosinusitis with and without nasal polyposis," Int Forum Allergy Rhinol, 2012, 2 (2):122-5.

Chiampanichayakul et al., "Production of monoclonal antibodies to P-glycoprotein: its application in detection of soluble and surface P-glycoprotein of leukemia patients," Int J Hematol, 2010, 92 (2):326-33.

Chu et al., "Detection of soluble P-glycoprotein in culture media and extracellular fluids," Biochem Biophys Res Commun, 1994, 203 (1):506-12.

Cleves and Kelly, "Protein translocation: Rehearsing the ABCs," Curr. Biol, 1996, 6:276-8.

Di Noto et al., "Immunoglobulin free light chains and GAGs mediate multiple myeloma extracellular vesicles uptake and secondary NFkB nuclear translocation," Frontiers in Immunology, Oct. 2014, 5: Article 517.

Drach et al., "Involvement of P-glycoprotein in the transmembrane transport of interleukin-2 (IL-2), IL-4, and interferon-gamma in normal human T lymphocytes," Blood, 1996, 88:1747-1754.

Dror et al., "Potentiation of anticancer-drug cytotoxicity by multidrug-resistance chemosensitizers involves alterations in membrane fluidity leading to increased membrane permeability," Eur J Biochem, 1995, 228:1020-9.

Ehrhardt et al., "16HBE14o—human bronchial epithelial cell layers express P-glycoprotein, lung resistance-related protein, and caveolin-1," Pharm. Res, 2003, 20 (4):545-51.

Feldman et al., "P-glycoprotein is a marker of tissue eosinophilia and radiographic inflammation in chronic rhinosinusitis without nasal polyps," Int Forum Allergy Rhinol, 2013, 3 (8):684-7.

Fernandez et al., "Influence of the pro-inflammatory cytokines on P-glycoprotein expression and functionality," J. Pharm. Pharm. Sci, 2004, 7:359-371.

Fokkens et al., "European Position Paper on Rhinosinusitis and Nasal Polyps 2012," Rhinol Suppl. 2012, (23):3 p preceding table of contents, 1-298.

Golden and Pollack, "Blood-brain barrier efflux transport," J Pharm Sci. 2003; 92(9):1739-53.

Gong et al., "Microparticles and their emerging role in cancer multidrug resistance," Cancer Treatment Reviews, 2012, 38: 226-234.

Gudis et al., "Acquired cilia dysfunction in chronic rhinosinusitis," Am. J. Rhinol. Allergy, 26:1-6.

Harding et al., "Receptor-mediated Endocytosis of Transferrin and of the Transferrin Receptor in Rat Reticulocytes Recycling," The Journal of Cell Biology, Aug. 1983, 97: 329-339.

Henrique et al., "Epigenetic regulation of MDR1 gene through post-translational histone modifications in prostate cancer," BMC Genomics, 2013, 14:898.

Hopkins et al., "Psychometric validity of the 22-item Sinonasal Outcome Test," Clin Otolaryngol, 2009, 34:447-454.

Hu et al., "Release of Luminal Exosomes Contributes to TLR4-Mediated Epithelial Antimicrobial Defense," PLOS Pathogens, Apr. 2013, 9: e1003261.

International Preliminary Report on Patentability in International Application No. PCT/US2017/013418, dated Jul. 17, 2018, 9 pages.

International Search Report and Written Opinion in International Application No. PCT/US2017/013418, dated Apr. 4, 2017, 16 pages.

(56) References Cited

OTHER PUBLICATIONS

Jansen et al., "Exosomal Secretion of Cytoplasmic Prostate Cancer Xenograft-derived Proteins," Molecular & Cellular Proteomics, 2009, 8: 1192-1205.

Johnstone et al., "Reticulocyte Maturation and Exosome Release: Transferrin Receptor Containing Exosomes Shows Multiple Plasma Membrane Functions," Blood, 1989, 74: 1844-1851.

Kandimalla and Donovan, "Localization and differential activity of P-glycoprotein in the bovine olfactory and nasal respiratory mucosae," Pharm Res, 2005, 22 (7):1121-8.

Kato et al., "Serum exosomal P-glycoprotein is a potential marker to diagnose docetaxel resistance and select a taxoid for patients with prostate cancer," Urologic Oncology: Seminars and Original Investigations, 2015, 1-6.

Kern et al., "Perspectives on the etiology of chronic rhinosinusitis: An immune barrier hypothesis," Am J Rhinol, 2008, 22:549-559.

Kharaziha et al., "Tumor cell-derived exosomes: A message in a bottle," Biochimica et Biophysica Acta, 2012, 1826: 103-111.

Lam et al., "Itraconazole and clarithromycin inhibit P-glycoprotein activity in primary human sinonasal epithelial cells," Int Forum Allergy Rhinol, 2015, 5(6):477-80.

Lee et al., "Exosomes and microvesicles: Extracellular vesicles for genetic information transfer and gene therapy," Hum. Mol. Genet, 2012, 21:125-134.

Lee et al., "Microvesicles as mediators of intercellular communication in cancer—the emerging science of cellular 'debris'," Semin. Immunopathol, 2011, 33: 455-467.

Levchenko et al., "Intercellular transfer of P-glycoprotein mediates acquired multidrug resistance in tumor cells," PNAS, 2005, 102:1933-1938.

Lo Cicero et al., "Exosomes released by keratinocytes modulate melanocyte pigmentation," Nature Communications, 2015, 6: 7506.

Lopes-Rodrigues et al., "The network of P-glycoprotein and microRNAs interactions," Int. J. Cancer, 2014, 135: 253-263.

Lopez and Martinez-Luis, "Marine Natural Products with P-Glycoprotein Inhibitor Properties," Mar Drugs, 2014, 12 (1): 525-546.

Lund and Mackay, "Staging in rhinosinusitis," Rhinology, 1993, 31 (4):183-4.

Lv et al., "Exosomes mediate drug resistance transfer in MCF-7 breast cancer cells and a probable mechanism is delivery of P-glycoprotein," Tumor Biol, 2014, 35:10773-10779.

Mack et al., "Transfer of the chemokine receptor CCR5 between cells by membrane-derived microparticles: a mechanism for cellular human immunodeficiency virus 1 infection," Nat. Med, 2000, 6:769-775.

Mallegol et al., "T84-Intestinal Epithelial Exosomes Bear MHC Class II/Peptide Complexes Potentiating Antigen Presentation by Dendritic Cells," Gastroenterology, 2007, 132:1866-1876.

McCloy et al., "Partial inhibition of Cdk1 in G2 phase overrides the SAC and decouples mitotic events," Cell Cycle, 2014, 13 (9):1400-1412.

Meckes, Jr., "Exosomal Communication Goes Viral," Journal of Virology, 2015, 89: 5200-5203.

Min et al., "Level of secreted HMGB1 correlates with severity of inflammation in chronic rhinosinusitis," Laryngoscope, 2015, 125: E225-E230.

Munagala et al., "Synthesis and evaluation of Strychnos alkaloids as MDR reversal agents for cancer cell eradication," Bioorganic & Medicinal Chemistry, 2014, 22 (3):1148-1155.

Munoz et al., "Delivery of Functional Anti-miR-9 by Mesenchymal Stem Cell-derived Exosomes to Glioblastoma Multiforme Cells Conferred Chemosensitivity," Molecular Therapy—Nucleic Acids, 2013, 2: e126.

Nocera et al., "Exosomes mediate interepithelial transfer of functional P-glycoprotein in chronic rhinosinusitis with nasal polyps," The Laryngoscope, May 2017.

Nocera et al., "Intact Soluble P-glycoprotein is Secreted by Sinonasal Epithelial Cells," Am. J. Rhinol. Allergy, 2016, 4:246-9.

Nocera et al., "Secreted P-Glycoprotein Is a Noninvasive Biomarker of Chronic Rhinosinusitis," The Laryngoscope, 2016, 4 pages.

Palmeira et al., "Three Decades of P-gp Inhibitors: Skimming Through Several Generations and Scaffolds," Current Medicinal Chemistry, 2012, 19: 1946-2025.

Pan et al., "Electron Microscopic Evidence for Externalization of the Transferrin Receptor in Vesicular Form in Sheep Reticulocytes," The Journal of Cell Biology, 1985, 101: 942-948.

Pasquier et al., "Different modalities of intercellular membrane exchanges mediate cell-to-cell P-glycoprotein transfers in MCF-7 breast cancer cells," J. Biol. Chem, 2012, 287:7374-7387.

Pauwels et al., "Emerging biologics for the treatment of chronic rhinosinusitis," Expert Rev Clin Immunol, 2015, 11 (3):349-61.

Ponikau et al., "An immunologic test for chronic rhinosinusitis based on free intranasal eosinophilic major basic protein," Int Forum Allergy Rhinol, 2015, 5 (1):28-35.

Rabinowits et al., "Exosomal MicroRNA: A Diagnostic Marker for Lung Cancer," Clinical Lung Cancer, 2009, 10: 42-46.

SBI System Biosciences, Exo-Glow™ Tracking Labels, 2014, 2 pages.

SBI System Biosciences, ExoQuick-TC™ Exosome Precipitation Solution-User Manual, 2013, 10 pages.

SBI System Biosciences, ExoQuick-TC™ Exosome precipitation, 2011, 2 pages.

SBI System Biosciences, ExoQuick™ Exosome Precipitation Solution—User Manual, 2013, 14 pages.

SBI System Biosciences, ExoQuick™ Exosome precipitation, 2011, 2 pages.

SBI System Biosciences, Exosome Antibodies, Array & ELISA Kits, 2014, 19 pages.

SBI System Biosciences, G-25 Spin column removal of ExoQuick polymers, downloaded from the internet on Jul. 3, 2015, presently available at https://www.systembio.com/wp-content/uploads/Remove-EXOQ-polymers.pdf. 1 page.

Scheffer et al., "Multidrug resistance related molecules in human and murine lung," J Clin Pathol, 2002, 55:332-339.

Schmid et al., "Released intranasal eosinophilic major basic protein as a diagnostic marker for polypoid chronic rhinosinusitis," Otolaryngol Head Neck Surg, 2010, 143 (3):386-91.

Schorey et al., "Exosomes and other extracellular vesicles in host-pathogen interactions," EMBO Rep, 2015, 16:24-43.

Shapiro and Ling, "Effect of quercetin on hoechst 33342 transport by purified and reconstituted p-glycoprotein," Biochem Pharmacol 1997; 53:587-96.

Sigma-Aldrich, Product Information: PKH26 Red Fluorescent Cell Linker Kits for General Cell Membrane Labeling, Technical Bulletin, Mar. 2011, 4 pages.

Szakács et al., "Targeting multidrug resistance in cancer," Nature Reviews, 2006, 5: 219-234.

Taylor and Gercel-Taylor, MicroRNA signatures of tumor-derived exosomes as diagnostic biomarkers of ovarian cancer, Gynecologic Oncology, 2008, 110: 13-21.

Théry et al., "Isolation and characterization of exosomes from cell culture supernatants and biological fluids," Curr. Protoc. Cell Biol, 2006, Supplement 30: Unit 3.22.1-3.22.29.

Tomassen et al., "Inflammatory endotypes of chronic rhinosinusitis based on cluster analysis of biomarkers," J. Allergy Clin. Immunol, 2016, 137: 1449-1456.e4.

Valadi et al., "Exosome-mediated transfer of mRNAs and microRNAs is a novel mechanism of genetic exchange between cells," Nature Cell Biology, 2007, 9: 654-659.

Van Deun et al., "The impact of disparate isolation methods for extracellular vesicles on downstream RNA profiling," Journal of Extracellular Vesicles, 2014, 3: 24858.

Van Niel et al., "Intestinal Epithelial Cells Secrete Exosome-like Vesicles," Gastroenterology, 2001, 121: 337-349.

Varma et al., "P-glycoprotein inhibitors and their screening: a perspective from bioavailability enhancement," Pharmacological Research, 2003, 48: 347-359.

Wioland et al., "CFTR, MDR1, and MRP1 immunolocalization in normal human nasal respiratory mucosa," J Histochem Cytochem, 2000, 48:1215-122.

(56) References Cited

OTHER PUBLICATIONS

Wolking et al., "Impact of Genetic Polymorphisms of ABCB1 (MDR1, P-Glycoprotein) on Drug Disposition and Potential Clinical Implications: Update of the Literature," Clin Pharmacokinet, 2015, 54 (7):709-35.
Wu et al., "Altered microRNA Expression Profiles of Extracellular Vesicles in Nasal Mucus From Patients With Allergic Rhinitis," Allergy Asthma Immunol Res, 2015, 7:449-457.
Bleier, "Regional Expression of Epithelial MDR1/P-gp in Chronic Sinusitis with and without Nasal Polyposis," Abstract of Presentation at Proceedings of the 57th Annual Meeting of the American Rhinologic Society, San Francisco, CA, Sep. 10, 2011, p. 71-72, 3 pages.
Bleier & Feldman, "Corticosteroid Sensitivity of Epithelial MDR1/P-gp in Chronic Sinusitis with Nasal Polyps," Abstract of Presentation at Proceedings of the 58th Annual Meeting of the American Rhinologic Society, Washington, DC, Sep. 8, 2012, p. 32, 2 pages.
Al-Massarani et al., "In vitro Cytotoxic, Antibacterial and Antiviral Activities of Triterpenes from the Red Sea Sponge, *Siphonochalina siphonella*," Tropical Journal of Pharmaceutical Research, Jan. 2015, 14(1):33-40.
Amorim et al., "Nasal eosinophilia: an indicator of eosinophilic inflammation in asthma," Clin Exp Allergy, Jun. 2010; 40(6):867-874.
Aqil et al., "Antimicrobial, antioxidant, and antimutagenic activities of selected marine natural products and tobacco cembranoids," Drug and Chemical Toxicology, 2011, 34(2):167-179.
Bachert et al., "*Staphylococcus aureus* enterotoxins: a key in airway disease?" Allergy, Jun. 2002;57(6):480-7.
Bark et al., "PSC833, cyclosporine analogue, downregulates MORI expression by activating JNK/c-Jun/AP-1 and suppressing NF-kB," Cancer Chemother Pharmacol., May 2010, 65(6):1131-1136.
Blackwell et al., "Summary health statistics for U.S. adults: National Health Interview Survey, 1997," Vital Health Stat 10, May 2002, (205):1-109.
Bleier et al., "Chitosan glycerophosphate-based semirigid dexamethasone eluting biodegradable stent," Am J Rhinol Allergy, 2009, 23:76-79.
Brody et al., "High-content affinity-based proteomics: unlocking protein biomarker discovery," Expert Rev. Mol. Diagn., 2010, 10(8):1013-1022.
CA Office Action in Canadian Appln. No. 2,928,035, dated Jun. 26, 2020, 4 pages.
Cervin et al., "Effects of long-term clarithromycin treatment on lavage-fluid markers of inflammation in chronic rhinosinusitis." Clinical Physiology and Functional Imaging, 2009, 29(2):136-142.
Chin et al., "Nasal polyposis: an inflammatory condition requiring effective anti-inflammatory treatment," Curr Opin Otolaryngol Head Neck Surg, 2013, 21(1):23-30.
Cho et al., "Impact of chronic rhinosinusitis and endoscopic sinus surgery on bone remodeling of the paranasal sinuses," Am J Rhinol, 2008, 22(5):537-541.
Damm et al., "Proinflammatory effects of *Staphylococcus aureus* exotoxin B on nasal epithelial cells," Otolaryngol Head Neck Surg., 2006, 134(2):245-9.
Detwiller et al., "Steroid-independent upregulation of matrix metalloproteinase 9 in chronic rhinosinusitis patients with radiographic evidence of osteitis," Int Forum Allergy Rhinol., May 2013, 3(5):364-368.
Erbek et al., "The role of allergy in the severity of nasal polyposis," Am J Rhinol, 2007, 21(6):686-90.
European Search Report in Application No. 13866961.9, dated Jun. 6, 2016, 7 pages.
Ferguson, "Categorization of eosinophilic chronic rhinosinusitis," Curr Opin Otolaryngol Head Neck Surg., 2004, 12(3):237-242.
Fokkens et al., "EPOS 2012: European position paper on rhinosinusitis and nasal polyps 2012. A summary for otorhinolaryngologists," Rhinology, 2012, 50(1):1-12.

Georgalas et al., "Global Osteitis Scoring Scale and chronic rhinosinusitis: a marker of revision surgery," Clin Otolaryngol, 2010, 35(6):455-461.
Georgalas, "Osteitis and paranasal sinus inflammation: what we know and what we do not," Curr Opin Otolaryngol Head Neck Surg, Feb. 2013, 21(1):45-49.
Han et al., "Predictors of bronchial hyperresponsiveness in chronic rhinosinusitis with nasal polyp," Allergy, Jan. 2009, 64(1):118-22.
Hopkins et al., "The Lund-Mackay staging system for chronic rhinosinusitis: how is it used and what does it predict?," Otolaryngol Head Neck Surg., 2007, 137(4):555-61.
International Preliminary Report on Patentability in International Application No. PCT/US2013/077945, dated Jul. 9, 2015, 6 pages.
International Search Report and Written Opinion in International Application No. PCT/US2013/077945, dated Apr. 29, 2014, 7 pages.
Iqbal et al., "Corticosteroid regulation of P-glycoprotein in the developing blood-brain barrier," Endocrinology, Mar. 2011, 152(3):1067-79.
Jain et al., "Reversal of P-Glycoprotein-Mediated Multidrug Resistance by Sipholane Triterpenoids," Journal of Natural Products, 2007, 70:928-931.
JP Office Action in Japanese Application No. 2018-536890, dated Dec. 8, 2020, 6 pages (with English translation).
Kim et al., "Automated Heart-Type Fatty Acid-Binding Protein Assay for the Early Diagnosis of Acute Myocardial Infarction," Am J Clin Pathol, Jul. 2010,134:157-162.
Kirkeby et al., "Quantitative immunohistochemistry of fluorescence labelled probes using low-cost software," J Immunol. Methods, Jun. 2005, 301(1-2):102-13.
Kooij et al., "P-glycoprotein acts as an immunomodulator during neuroinflammation," PLoS One, Dec. 2009, 4(12):e8212.
Kopriva et al., "The anti-inflammatory effects of inhaled corticosteroids versus anti-leukotrienes on the lymphocyte P-glycoprotein (PGP) expression in asthmatic children," J Asthma., May 2009, 46(4):366-70.
Lalaker et al. "Chitin stimulates expression of acidic mammalian chitinase and eotaxin-3 by human sinonasal epithelial cells in vitro," Am J Rhinol Allergy, 2009, 23(1):8-14.
Lane et al., "Altered expression of genes associated with innate immunity and inflammation in recalcitrant rhinosinusitis with polyps," Am J Rhinol., 2006, 20(2):138-44.
Lee et al., "The incidence of concurrent osteitis in patients with chronic rhinosinusitis: a clinicopathological study," Am J Rhinol, 2006, 20(3):278-282.
Lee et al., "Risk factors for protracted sinusitis in pediatrics after endoscopic sinus surgery," Auris Nasus Larynx., Dec. 2009, 36(6):655-60.
Marty et al., "ATP binding cassette transporter ABC1 is required for the release of interleukin-1beta by P2X7-stimulated and lipopolysaccharide-primed mouse Schwann cells," Glia, Mar. 2005, 49(4):511-9.
Mehta et al., "Blood and sputum eosinophil levels in asthma and their relationship to sinus computed tomographic findings," Mayo Clin Proc., Jun. 2008, 83(6):671-8.
Mjösberg et al., "Human IL-25- and IL-33-responsive type 2 innate lymphoid cells are defined by expression of CRTH2 and CD161," Nat Immunol., Sep. 2011, 11;12(11):1055-62.
Morjani et al., "Immunosuppressors as multidrug resistance reversal agents," Methods Mol Biol., 2010, 596:433-46.
Newman et al., "Chronic sinusitis. Relationship of computed tomographic findings to allergy, asthma, and eosinophilia," JAMA, Feb. 1994, 271(5):363-7.
Nickel, "The mystery of nonclassical protein secretion. A current view on cargo proteins and potential export routes," Eur J Biochem., May 2003, 270(10):2109-19.
Olze et al., "Eosinophilic nasal polyps are a rich source of eotaxin, eotaxin-2 and eotaxin-3," Rhinology, Jun. 2006, 44(2):145-50.
Peters et al., "Evidence for altered activity of the IL-6 pathway in chronic rhinosinusitis with nasal polyps," J Allergy Clin Immunol., Feb. 2010, 125(2):397-403.
Pfaffe et al., "Diagnostic Potential of Saliva: Current State and Future Applications," Clin. Chem., May 2011, 57(5):675-687.

(56) References Cited

OTHER PUBLICATIONS

Philips et al., "Rapid Point-Of-Care Breath Test for Biomarkers of Breast Cancer and Abnormal Mammograms," PLoS One, 2014, 9(3):e90226.
Piccirillo et al., "Psychometric and clinimetric validity of the 20-Item Sino-Nasal Outcome Test (SNOT-20)," Otolaryngol Head Neck Surg., 2002, 126(1):41-7.
Quintanilla-Dieck, et al., "Comparison of disease-specific quality-of-life instruments in the assessment of chronic rhinosinusitis," International Forum of Allergy & Rhinology, 2012, 2(6):437-443.
Reh et al., "Treatment-recalcitrant chronic rhinosinusitis with polyps is associated with altered epithelial cell expression of interleukin-33," Am J Rhinol Allergy, 2010, 24(2):105-9.
Riechelmann et al., "Biological markers in nasal secretions," Eur. Respir. J., Apr. 2003, 21(4):600-605.
Rosenfeld et al., "Clinical practice guideline: adult sinusitis," Otolaryngol Head Neck Surg., Sep. 2007, 137(3 Suppl):S1-31.
Ruocco et al., "A new collection method for the evaluation of nasal mucus proteins," Clin Exp Allergy, Jul. 1998, 28(7):881-888.
Ryan et al., "Correlations Between Symptoms, Nasal Endoscopy, and In-Office Computed Tomography in Post-Surgical Chronic Rhinosinusitis Patients," Laryngoscope, 2011, 121(3):674-678.
Sachse et al., "*Staphylococcus aureus* invades the epithelium in nasal polyposis and induces IL-6 in nasal epithelial cells in vitro," Allergy, Nov. 2010, 65(11):1430-7.
Secher et al., "Intranasal Verapamil in Allergen-Induced Rhinitis." Allergy, 1983, 38:565-570.
Snidvongs et al., "Correlation of the Kennedy Osteitis Score to clinico-histologic features of chronic rhinosinusitis," Int Forum Allergy Rhinol., May 2013, 3(5):369-75.
Snidvongs et al., "Osteitic bone: a surrogate marker of eosinophilia in chronic rhinosinusitis," Rhinology, Sep. 2012, 50(3):299-305.
Soler et al., "Impact of mucosal eosinophilia and nasal polyposis on quality-of-life outcomes after sinus surgery," Otolaryngol Head Neck Surg., Jan. 2010, 142(1):64-71.
Soler et al., "Relationship between clinical measures and histopathologic findings in chronic rhinosinusitis," Otolaryngol Head Neck Surg., Oct. 2009, 141(4):454-61.
Stein et al., "Modulation of mdr1 expression by cytokines in human colon carcinoma cells: an approach for reversal of multidrug resistance," Br J Cancer, Nov. 1996, 74(9):1384-91.
Sun et al., "Clinical significance of eosinophilic cationic protein levels in nasal secretions of patients with nasal polyposis," Eur Arch Otorhinolaryngol., Jul. 2009, 266(7):981-6.
Szucs et al., "Eosinophilia in the ethmoid mucosa and its relationship to the severity of inflammation in chronic rhinosinusitis," Am J Rhinol., 2002, 16(3):131-4.
Takeno et al., "Pathological mechanisms and clinical features of eosinophilic chronic rhinosinusitis in the Japanese population," Allergol Int., Sep. 2010, 59(3):247-56.
Van Crombruggen et al., "Pathogenesis of chronic rhinosinusitis: inflammation," J Allergy Clin Immunol., Oct. 2011, 128(4):728-32.
Walsh and Falsey, "A simple and reproducible method for collecting nasal secretions in frail elderly adults, for measurement of virus-specific IgA," J Infect Dis., May 1999, 179(5):1268-73.
Wanek et al., "A comparative small-animal PET evaluation of ["C]tariquidar, ["C]elacridar and (R)-["C]verapamil for detection of P-glycoprotein-expressing murine breast cancer." Eur J Nucl Med Mol Imaging., Jan. 2012, 39(1):149-159.
Wisniewski et al., "Novel cytokines and cytokine-producing T cells in allergic disorders," Allergy Asthma Proc., 2011, 32(2):83-94.
Yakimchuk, "Exosomes: isolation and characterization methods and specific markers," Mater Methods, 2015, 5:1450-1453.
Yasun et al., "Enrichment and Detection of Rare Proteins with Aptamer-conjugated Gold Nanorods," Anal Chem, Jul. 2012, 84(14):6008-6015.
Zadeh et al., "Significance of eosinophilia in chronic rhinosinusitis," Am J Rhinol., 2002, 16(6):313-7.
ClinicalTrials.gov [online], "Trial of Topical Verapamil in Chronic Rhinosinusitis With Nasal Polyps," NCT03102190, Apr. 5, 2017, retrieved May 9, 2020, retrieved from URL <https://clinicaltrials.gov/ct2/show/NCT03102190>, 9 pages.
International Search Report and Written Opinion in International Appln. No. PCT/US2020/024476, dated Jun. 11, 2020, 10 pages.
JP Office Action in Japanese Application No. 2018-536890, dated Sep. 7, 2021, 4 pages (with English translation).
Northwestern Medicine [online], "Nasal Saline Irrigation Instructions," Jun. 2018, retrieved May 11, 2020, retrieved from URL <file:///U:/Downloads/northwestern-medicine-nasal-saline-irrigation-instructions.pdf>, 1 page.
Abdel Mouez et al., "Bioavailability enhancement of verapamil HCl via intranasal chitosan microspheres," Eur. J. Pharm. Sci., 2014, 51:59-66.
Arnold et al., "Pharmacodynamics of acute intranasal administration of verapamil: comparison with i.v. and oral administration," Biopharm. Drug Dispos, 1985, 6(4):447-54.
Bachert et al., "Effect of Subcutaneous Dupilumab on Nasal Polyp Burden in Patients With Chronic Sinusitis and Nasal Polyposis: A Randomized Clinical Trial," JAMA, Feb. 2016, 315(5):469-79.
Becker, "Cluster headache: a conventional pharmacological management," Headache, Jun. 2013, 53(7):1191-1196.
Cohen et al., "Electrocardiographic abnormalities in patients with cluster headache on verapamil therapy," Neurology, 2007; 69(7):668-675.
Derycke et al., "Mixed T helper cell signatures in chronic rhinosinusitis with and without polyps," PLoS One, Jun. 2014, 9(6):e97581, 8 pages.
Dinis et al., "Sinus tissue concentration of moxifloxacin after a single oral dose," Ann. Otol. Rhinol. Laryngol., 2004, 113(2):142-146.
Edmiston et al., "Tissue and fluid penetration of garenoxacin in surgical patients," Surg. Infect. (Larchmt)., Apr. 2007, 8(2):179-88.
Gehanno et al., "A prospective, multicentre study of moxifloxacin concentrations in the sinus mucosa tissue of patients undergoing elective surgery of the sinus," J. Antimicrob. Chemother., May 2002, 49(5):821-826.
Gevaert et al., "Mepolizumab, a humanized anti-IL-5 mAb, as a treatment option for severe nasal polyposis," J. Allergy Clin. Immunol., Nov. 2011, 128(5):989-95, 15 pages.
Gevaert et al., "Nasal IL-5 levels determine the response to anti-IL-5 treatment in patients with nasal polyps," J. Allergy Clin. Immunol., Nov. 2006, 118(5):1133-41.
Harvey et al., "Fluid residuals and drug exposure in nasal irrigation," Otolaryngol. Head Neck Surg., Dec. 2009, 141(6):757-761.
Hashemi et al., "Effectiveness of itraconazole on clinical symptoms and radiologic findings in patients with recurrent chronic rhinosinusitis and nasal polyposis," Adv. Biomed. Res., 2014, 3(162): 5 pages.
Hashioka et al., "Inhibition of human astrocyte and microglia neurotoxicity by calcium channel blockers," Neuropharmacology, Sep. 2012, 63(4):685-691.
Hedman et al., "Prevalence of asthma, aspirin intolerance, nasal polyposis and chronic obstructive pulmonary disease in a population-based study," Int. J. Epidemiol., Aug. 1999, 28(4):717-22.
Hissaria et al., "Short course of systemic corticosteroids in sinonasal polyposis: a double-blind, randomized, placebo-controlled trial with evaluation of outcome measures," J. Allergy Clin. Immunol., Jul. 2006, 118(1):128-33.
Hopkins et al., "Long-term outcomes from the english national comparative audit of surgery for nasal polyposis and chronic rhinosinusitis," Laryngoscope, Dec. 2009, 119(12):2459-2465.
Hospira GEHS, "Verapamil Hydrochloride Injection: Safety Data Sheet," Hospira Inc., revised Jun. 2014, 7 pages.
Hsiao et al., "National Ambulatory Medical Care Survey: 2007 summary," Natl. Health Stat. Report., Nov. 2010, 3(27):1-32.
Johansson et al., "Prevalence of nasal polyps in adults: the Skovde population-based study," Ann. Otol. Rhinol. Laryngol., Jul. 2003, 112(7):625-9.
Khakzad et al., "Effect of verapamil on bronchial goblet cells of asthma: an experimental study on sensitized animals," Pulm. Pharmacol. Ther., Apr. 2012, 25(2):163-168.
Klossek et al., "Prevalence of nasal polyposis in France: a cross-sectional, casecontrol study," Allergy, Feb. 2005, 60(2):233-7.

(56) References Cited

OTHER PUBLICATIONS

Kocharyan et al., "P-glycoprotein inhibition promotes prednisone retention in human sinonasal polyp explants," Int. Forum Allergy Rhinol., Aug. 2014, 4(9):734-738.

Lanteri-Minet et al., "Cardiac safety in cluster headache patients using the very high dose of verapamil (>720 mg/day)," J. Headache Pain, Apr. 2011, 12(2):173-176.

Lasser et al., "Exosomes in the nose induce immune cell trafficking and harbour an altered protein cargo in chronic airway inflammation," J. Transl. Med., Jun. 2016, 14(1)181, 14 pages.

Li et al., "Verapamil modulates LPS-induced cytokine production via inhibition of NF-kappa B activation in the liver," Inflamm. Res., Mar. 2006, 55(3):108-13.

Matsumori et al., "Calcium Channel Blockers Differentially Modulate Cytokine Production by Peripheral Blood Mononuclear Cells," Circ. J., Mar. 2010, 74(3):567-571.

Meltzer et al., "Development of questionnaires to measure patient preferences for intranasal corticosteroids in patients with allergic rhinitis," Otolaryngol. Head Neck Surg., Feb. 2005, 132(2):197-207.

Miyake et al., "Double-blind placebo-controlled randomized clinical trial of verapamil for chronic rhinosinusitis with nasal polyps," J. Allergy Clin. Immunol., Jul. 2017, 140(1):271-273.

Nagarkar et al., "Thymic stromal lymphopoietin activity is increased in nasal polyps of patients with chronic rhinosinusitis," J. Allergy Clin. Immunol., Sep. 2013, 132(3):593-600.e12.

Orlandi et al., "International Consensus Statement on Allergy and Rhinology: Rhinosinusitis," Int. Forum Allergy Rhinol., Feb. 2016, 6 Suppl 1:S22-S209.

Peric et al., "Effect of long-term, low-dose clarithromycin on T helper 2 cytokines, eosinophilic cationic protein and the 'regulated on activation, normal T cell expressed and secreted' chemokine in the nasal secretions of patients with nasal polyposis," J. Laryngol. Otol., May 2012, 126(5):495-502.

Poetker et al., "Oral corticosteroids in the management of adult chronic rhinosinusitis with and without nasal polyps: an evidence-based review with recommendations," Int. Forum Allergy Rhinol., Feb. 2013, 3(2):104-120, 17 pages.

Rawal et al., "Post-operative budesonide irrigations for patients with polyposis: a blinded, randomized controlled trial," Rhinology, Sep. 2015, 53(3):227-34.

Rotenberg et al., "Postoperative care for Samter's triad patients undergoing endoscopic sinus surgery: a double-blinded, randomized controlled trial," Laryngoscope, Dec. 2011, 121(12):2702-5.

Rudmik et al., "Productivity costs in patients with refractory chronic rhinosinusitis," Laryngoscope, Sep. 2014, 124(9):2007-2012.

Rupa et al., "A prospective, randomised, placebo-controlled trial of postoperative oral steroid in allergic fungal sinusitis," Eur. Arch. Otorhinolaryngol., Feb. 2010, 267(3):233-8.

Sarangapani et al., "Interspecies dose extrapolation for inhaled dimethyl sulfate: a PBPK model-based analysis using nasal cavity N7-methylguanine adducts," Inhal. Toxicol., Aug. 2004, 16(9):593-605.

Smith et al., "Cost of adult chronic rhinosinusitis: A systematic review," Laryngoscope, Jul. 2015, 125(7)1547-56, 10 pages.

Smith et al., "National burden of antibiotic use for adult rhinosinusitis," J. Allergy Clin. Immunol., Nov. 2013, 132(5):1230-1232.

Soudry et al., "Safety analysis of long-term budesonide nasal irrigations in patients with chronic rhinosinusitis post endoscopic sinus surgery," Int. Forum Allergy Rhinol., Jun. 2016, 6(6):568-72.

Tsuruo et al., "Enhancement of vincristine- and adriamycininduced cytotoxicity by verapamil in P388 leukemia and its sublines resistant to vincristine and adriamycin," Biochem. Pharmacol., Oct. 1982, 31(19):3138-40.

Vaidyanathan et al., "Treatment of chronic rhinosinusitis with nasal polyposis with oral steroids followed by topical steroids: a randomized trial," Ann. Intern. Med., Mar. 2011, 154(5):293-302, 12 pages.

Van Zele et al., "Differences in initial immunoprofiles between recurrent and nonrecurrent chronic rhinosinusitis with nasal polyps," Am. J. Rhinol. Allergy, 2014, 28(3):192-8.

Van Zele et al., "Oral steroids and doxycycline: two different approaches to treat nasal polyps," J. Allergy Clin. Immunol., May 2010, 125(5):1069-1076.e4.

Vogelgesang et al., "Stereoselective first-pass metabolism of highly cleared drugs: studies of the bioavailability of L- and D-verapamil examined with a stable isotope technique," Br. J. Clin. Pharmacol., Nov. 1984, 18(5):733-740.

Wallace et al., "The diagnosis and management of rhinitis: An updated practice parameter," J. Allergy Clin. Immunol., Aug. 2008, 122:S1-S84.

Watling et al., "Abstract: Comparison of intransal versus intravenous verapamil bioavailability," Int. J. Clin. Pharmacol. Ther. Toxicol., 1993, 31(2): 1 page.

Wenzel et al., "Dupilumab in persistent asthma with elevated eosinophil levels," N. Engl. J. Med., Jun. 2013, 368(26):2455-66.

* cited by examiner

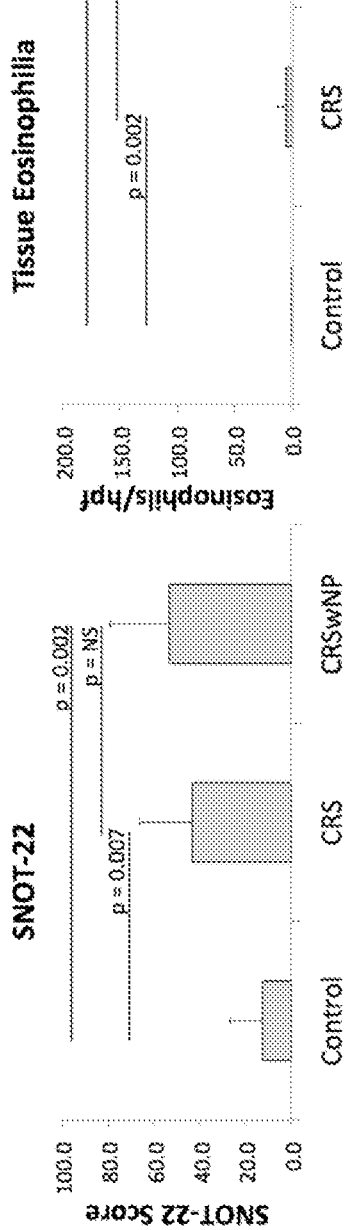
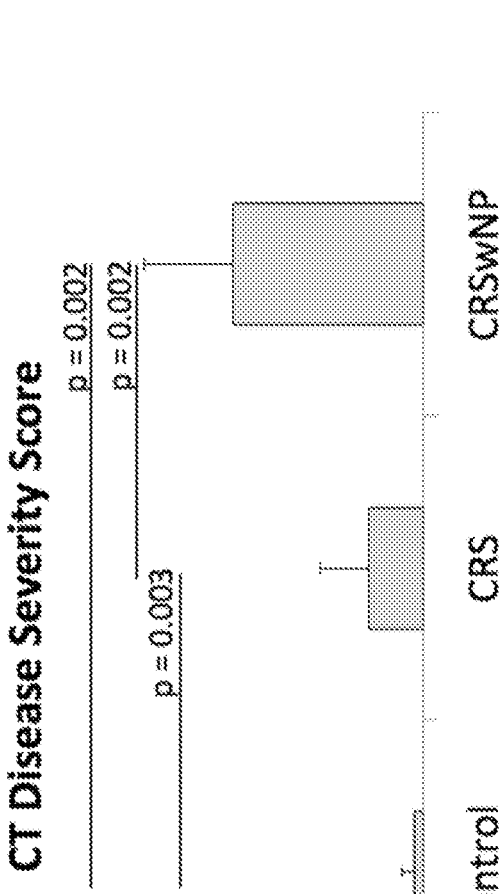
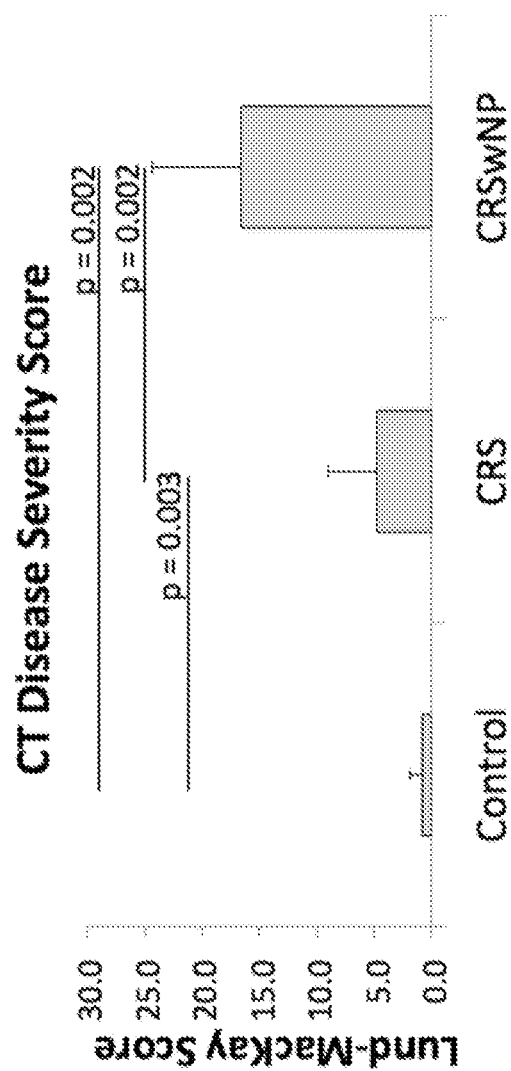
FIG. 5A
FIG. 5B
FIG. 5C

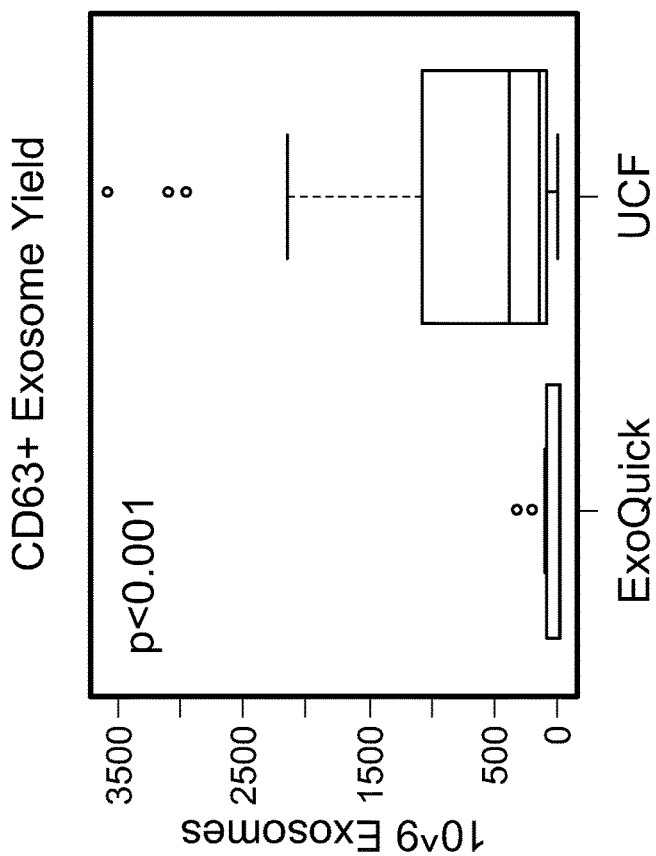
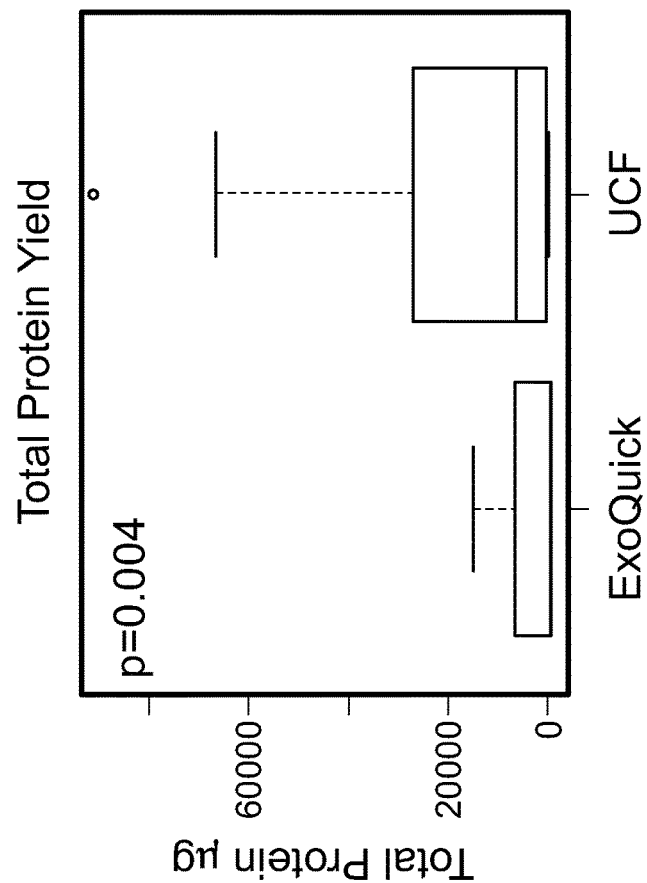
FIG. 10A
FIG. 10B

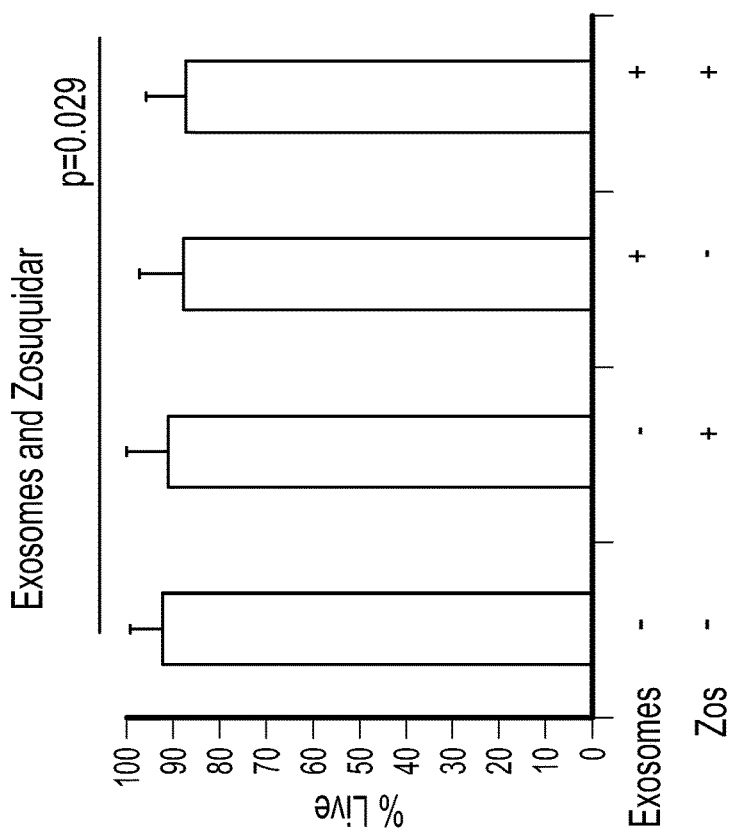
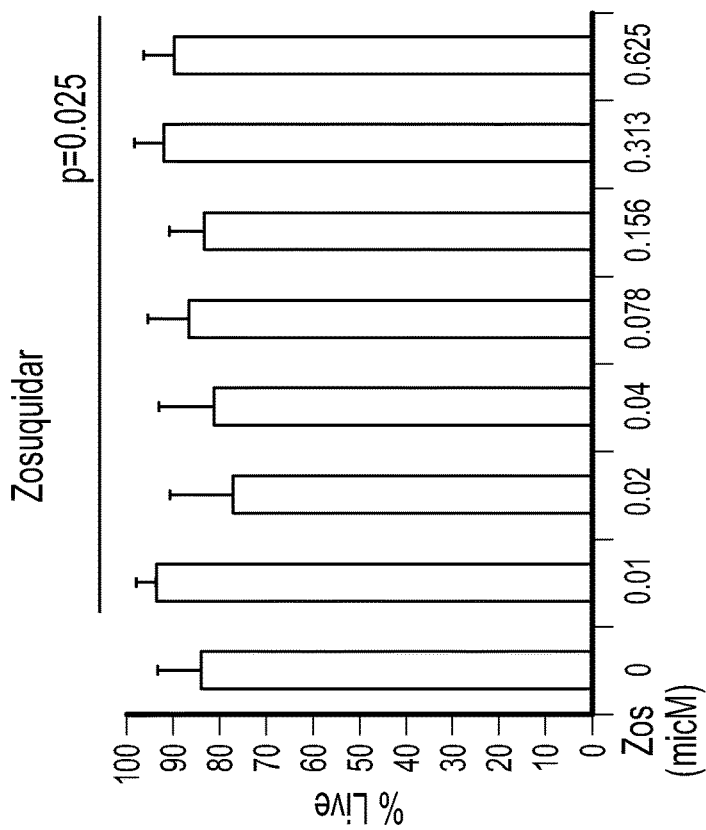
FIG. 11A
FIG. 11B

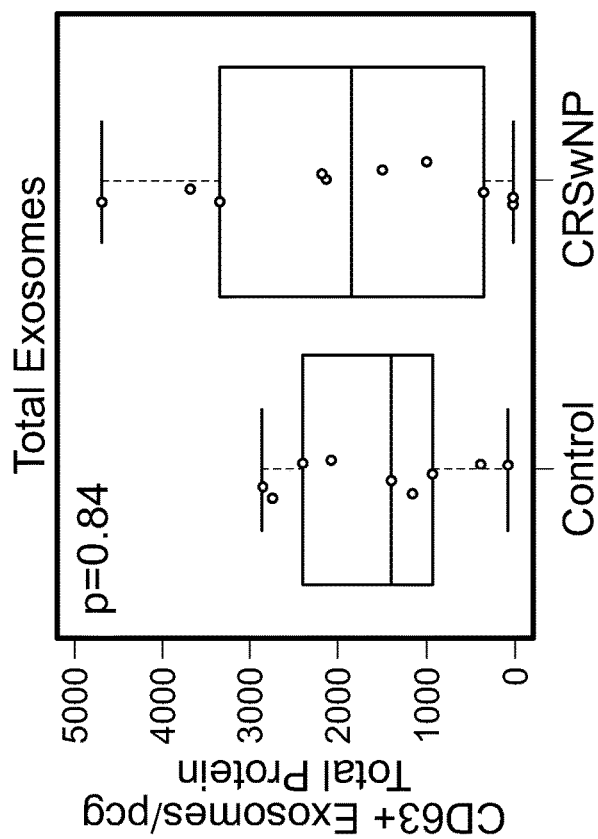
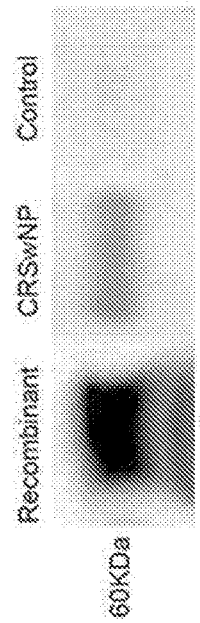
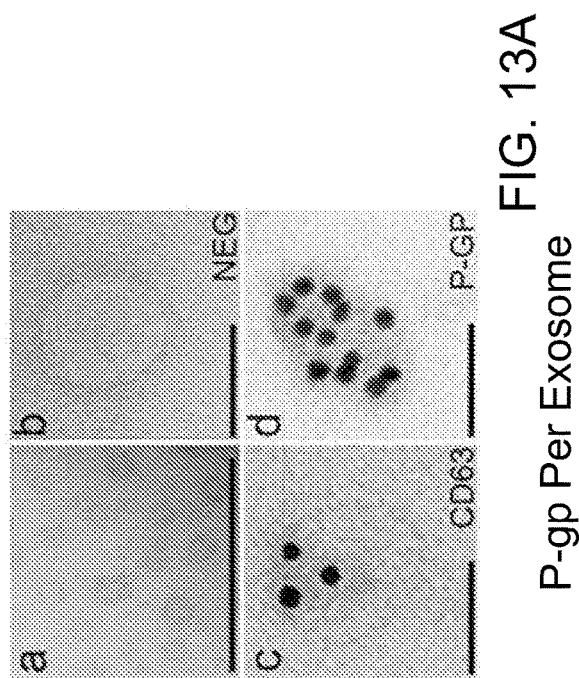
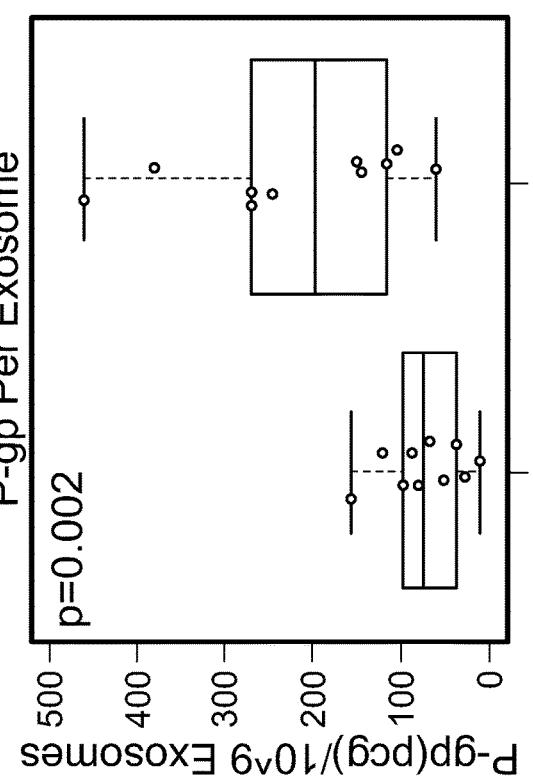
FIG. 13A
FIG. 13B
FIG. 13C
FIG. 13D

SECRETED P-GLYCOPROTEIN IS A NON-INVASIVE BIOMARKER OF CHRONIC RHINOSINUSITIS

This application is a 371 U.S. National Phase Application of PCT/US2017/013418, filed on Jan. 13, 2017, which claims the benefit of U.S. Provisional Patent Application Ser. No. 62/279,590, filed on Jan. 15, 2016. The entire contents of the foregoing are hereby incorporated by reference.

TECHNICAL FIELD

Described herein are methods for identifying and optionally treating subjects, e.g., subjects who have Chronic Rhinosinusitis (CRS), based on the detection of elevated levels of soluble p-glycoprotein.

BACKGROUND

Chronic Rhinosinusitis (CRS) is characterized by chronic inflammation of the sinonasal mucosa. While clinical manifestations of disease subtypes such as CRS with and without Nasal Polyps (NP) have long been recognized, advances in our understanding of the pathophysiology (Kern et al., Am J Rhinol. 22:549-559) of CRS have led to the adoption of the endotype paradigm (Akdis et al., J Allergy Clin Immunol. 2013; 131 (6):1479-90) of disease characterization. While phenotypic and immunologic features of CRS may exist along a spectrum within a specific endotype, this diagnostic structure provides important prognostic information and has ushered in an age of targeted medical therapies (Pauwels et al., Expert Rev Clin Immunol. 2015; 11 (3):349-61).

As personalized treatment of CRS continues to advance, the development of non-invasive biomarkers of disease endotype will become critical in order to rapidly and atraumatically categorize patients in an outpatient setting. Nasal mucus represents a natural potential reservoir for such biomarkers as it is secreted in copious volumes and may be easily sampled. Several groups have already exploited these advantages and have reported on the presence of free intranasal eosinophilic major basic protein (eMBP) as a sensitive and specific biomarker of CRS (Ponikau et al., Int Forum Allergy Rhinol. 2015; 5 (1):28-35; Schmid et al., Otolaryngol Head Neck Surg. 2010; 143 (3):386-91). Despite these findings, eMBP requires careful sampling methodology and there exists some discrepancy in the literature as to whether it is present in patients who would otherwise be considered non-eosinophilic (Ponikau et al., Int Forum Allergy Rhinol. 2015; 5 (1):28-35).

SUMMARY

The continued discovery of non-invasive biomarkers is critical to refine our ability to diagnose and treat CRS. While P-gp is secreted into nasal mucus under physiologic conditions, elevated secretion was associated with greater disease severity by both objective and subjective indices. The presence of elevated P-gp secretion may therefore represent a novel non-invasive biomarker of CRS and could also be used to predict patients who may benefit from P-gp inhibitory therapeutic strategies.

Thus, provided herein are methods for diagnosing Chronic Rhinosinusitis (CRS), e.g., T-helper cell type 2 (Th2) dominant chronic rhinosinusitis (CRS) endotype, in a subject. The methods include providing a sample comprising nasal secretions, e.g., nasal mucus, from a subject; determining a level of soluble p-glycoprotein (P-gp) in the sample; and comparing the level of P-gp in the sample to a reference level of P-gp, wherein a level of P-gp in the sample above the reference level indicates that the subject has CRS (and the method can include identifying a subjection with a level of P-gp above the reference level as having CRS). In some embodiments, the methods include identifying the subject as having CRS. In some embodiments, the methods include selecting and/or administering a treatment for CRS to the subject. In some embodiments, the treatment for CRS is administration of a therapeutically effective amount of a P-gp inhibitor.

Also provided herein are methods for selecting a subject for treatment with a P-glycoprotein inhibitor. The methods include providing a sample comprising nasal secretions, e.g., nasal mucus, from a subject; determining a level of soluble p-glycoprotein (P-gp) in the sample; and comparing the level of P-gp in the sample to a reference level of P-gp; wherein a level of P-gp in the sample above the reference level indicates that the subject is likely to benefit from treatment with a P-glycoprotein inhibitor; and selecting the subject for treatment with a P-glycoprotein inhibitor; and optionally administering to the subject an effective amount of a P-glycoprotein inhibitor.

In some embodiments, the sample comprises nasal mucus derived exosomes, and determining a level of soluble p-glycoprotein (P-gp) in the sample comprises determining a level of P-gp in the nasal mucus derived exosomes. In some embodiments, the methods include isolating nasal mucus derived exosomes from the subject; and determining a level of P-gp in the nasal mucus derived exosomes. Generally, in these embodiments, the level of P-gp is compared to a relevant reference level determined in exosomal samples.

In some embodiments, determining a level of soluble p-glycoprotein (P-gp) in the sample comprises contacting the sample with an antibody or antigen-binding fragment thereof that binds specifically to P-gp.

In some embodiments, providing a sample comprising nasal secretions, e.g., nasal mucus, from a subject comprises collecting the sample from the subject using nasal lavage or a sponge or other absorptive material.

In some embodiments of the methods described herein, the P-glycoprotein inhibitor is PSC 833, R-verapamil, GF120918, VX-710, MS-209, LY335979, OC144093, R101933, XR9051, or XR9576.

In some embodiments of the methods described herein, the P-glycoprotein inhibitor is administered systemically or locally to the subject's nasal passage and sinuses.

In some embodiments of the methods described herein, the P-glycoprotein inhibitor is delivered to the subject's nasal passage and sinuses by an inhalation device, by flushing, or by spraying.

In some embodiments of the methods described herein, the P-glycoprotein inhibitor is administered to the subject as a P-glycoprotein inhibitor eluting implant surgically placed in the subject's nasal passage or sinuses. In some embodiments of the methods described herein, the P-glycoprotein inhibitor eluting implant is bio-absorbable.

In some embodiments of the methods described herein, the presence of rhinosinusitis is confirmed by endoscopy or computed tomography.

In some embodiments of the methods described herein, the P-glycoprotein inhibitor is administered in combination with one or both of a corticosteroid and an antibiotic. In some embodiments, the corticosteroid is selected from dexamethasone, prednisone, prednisolone, triamcinolone, cortisol, budesonide, mometasone, fluticasone, flunisolide, and betamethasone. In some embodiments, the antibiotic is selected from erythromycin, doxycycline, tetracycline, penicillin, beta-lactam, macrolide, fluoroquinolone, cephalosporin, and sulfonamide.

Also provided herein are kits for use in the method of any of the preceding claims, comprising an antibody or antigen-binding fragment thereof that binds specifically to P-glycoprotein, optionally a control sample comprising a known amount of P-glycoprotein, optionally a container for containing the sample, and optionally a sponge or other absorptive material for collecting the sample.

In some embodiments, a subject (e.g., having rhinosinusitis) is identified using a methods described herein and treated, e.g., by administration to the subject an effective amount of a P-gp inhibitor or other agent such as corticosteroids which could be potentiated by the use of a P-gp inhibitor. The subject having rhinosinusitis may be further identified, or a diagnosis confirmed, by one of skill in the art based on known methods, e.g., based on detection of the presence of symptoms, by endoscopy, or by computed tomography. The efficacy of the treatment may be monitored by methods known in the art, e.g., by monitoring symptoms, by endoscopy or computed tomography.

In one aspect, a subject with rhinosinusitis is treated with a P-gp inhibitor in an amount sufficient to inhibit P-gp expression and/or activity. The P-gp inhibitor could be a first generation compound, e.g. verapamil, cyclosporin A, antihypertensive, reserpine, quinidine or yohimbine, tamoxifen, or toremifena. Preferably, the P-gp inhibitor is a second, third, or fourth generation compound as known in the art or described herein, e.g. PSC 833, R-verapamil, elacridar (GF120918/GG918), MS-209, OC144093, XR9051, LY335979, Cyclopropyldibenzosuberane zosuquidar (LY335979), laniquidar (R101933), mitotane (NSC-38721), biricodar (VX-710), ONT-093, tariquidar (XR9576), and HM30181 (See, e.g., Amin, Drug Target Insights. 2013; 7:27-34); Munagala et al., Bioorganic & Medicinal Chemistry, 22 (3):1148-1155 (2014)); Lopez and Martinez-Luis, Mar Drugs. 2014 January; 12 (1): 525-546; Palmeira et al., Current Medicinal Chemistry, 2012, 19, 1946-2025).

In another aspect, a subject with rhinosinusitis is treated with a P-gp inhibitor in an amount sufficient to decrease P-gp expression in the subject's sinonasal epithelial cells, either transcriptionally or post-transcriptionally.

In some embodiments, the P-gp inhibitor is administered systemically. In other embodiments, the P-gp inhibitor is administered locally to the subject's nasal passage and sinuses by an inhalation device, by flushing, spraying, irrigation, nebulization, atomization, or a drug eluting vehicle.

In some embodiments, a subject with rhinosinusitis is treated with a P-gp inhibitor in combination with other conventional treatments, e.g., drugs such as corticosteroids and/or antibiotics, to potentiate the effect of treatment.

In some embodiments, when a subject with rhinosinusitis has nasal polyps, or, surgical removal of such nasal polyps can be performed in addition to administration of a P-gp inhibitor to the subject. Thus, a subject with rhinosinusitis may undergo both surgery and treatment with a P-gp inhibitor. A subject without nasal polyps but with eosinophilic sinusitis may also undergo both surgery and treatment with a P-gp inhibitor.

In some embodiments, a subject with rhinosinusitis has eosinophilic sinusitis and/or other forms of mucosal inflammation.

In some embodiments, a subject continues to experience symptoms of chronic sinusitis after a sinus surgery, and a P-gp inhibitor-eluting implant, stent, or spacer is used to maintain sinus patency in the subject. The P-gp inhibitor eluting device can be made from bioabsorbable material so that the implant will be absorbed within a short period of time after the implantation and no surgical removal of the implant is necessary. The P-gp inhibitor eluting device can be in the form of solid, semisolid, gel, polymer, or particle.

In some embodiments, the P-glycoprotein inhibitor is administered in combination with one of both of a corticosteroid and/or an antibiotic. The corticosteroid can be, e.g., selected from dexamethasone, prednisone, prednisolone, triamcinolone, cortisol, budesonide, mometasone, fluticasone, flunisolide, and betamethasone. The antibiotic can be, e.g., selected from erythromycin, doxycycline, tetracycline, penicillin, beta-lactam, macrolide, fluoroquinolone, cephalosporin, and sulfonamide.

In some embodiments, a kit for treating rhinosinusitis in a subject is provided. Such a kit comprises a pharmaceutical composition comprising an effective amount of a P-gp inhibitor, and a device for delivering the pharmaceutical composition to the subject's nasal passage and sinuses. The device may deliver the pharmaceutical composition to the subject's nasal passage and sinuses in a liquid or an aerosolized form. In some embodiments, the kit also includes a corticosteroid and/or an antibiotic, in the same pharmaceutical composition as the P-gp inhibitor or in a separate composition.

As used herein, "treatment" means any manner in which one or more of the symptoms of a disease or disorder are ameliorated or otherwise beneficially altered. As used herein, amelioration of the symptoms of a particular disorder refers to any lessening, whether permanent or temporary, lasting or transient that can be attributed to or associated with treatment by the compositions and methods of the present disclosure.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

The term "subject" is used throughout the specification to describe an animal, human or non-human, to whom treatment according to the methods of the present invention is provided. Veterinary and non-veterinary applications are contemplated. The term includes, but is not limited to, mammals, e.g., humans, other primates, pigs, rodents such as mice and rats, rabbits, guinea pigs, hamsters, cows, horses, cats, dogs, sheep and goats. Typical subjects include humans, farm animals, and domestic pets such as cats and dogs.

The term "rhinosinusitis" as used herein includes acute and chronic rhinosinusitis, either with or without the presence of nasal polyps.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 5A-C 1. Histograms of clinical disease severity indices by diagnosis.

FIGS. 10A-B. Comparison of (A) protein and (B) CD63+ exosome concentration by isolation method demonstrating enhanced yield using ultracentrifugation (UCF).

FIGS. 11A-B. In vitro cytotoxicity assay demonstrating greater than 80% survival for the highest concentrations of Zosuquidar (ZOS) and Exosomes/ZOS.

FIGS. 13A-D. Characterization of mucus derived exosomes: (A) TEM images demonstrating a. Whole mounted exosomes purified from nasal mucus (bar 500 nm). b. Negative control (bar 100 nm for b-d) confirming the typical exosome size and morphology. c-d. Immunogold labeling of exosome marker CD63 and P-gp localizing to the exosome membrane. (B) Scatter/boxplots (median and interquartile range, bars represent 1.5 times the interquartile range) demonstrating similar total exosome concentrations between CRSwNP and control patients. (C) Scatter/boxplots (median and interquartile range, bars represent 1.5 times the interquartile range) demonstrating a significantly higher P-gp per exosome concentration in CRSwNP patients relative to control. (D) Western blot of P-gp in purified mucus derived exosomes (10 µg) demonstrating significantly weaker expression in control patients relative to CRSwNP (recombinant P-gp is positive control, negative loading control not shown).

DETAILED DESCRIPTION

Figure 1A:
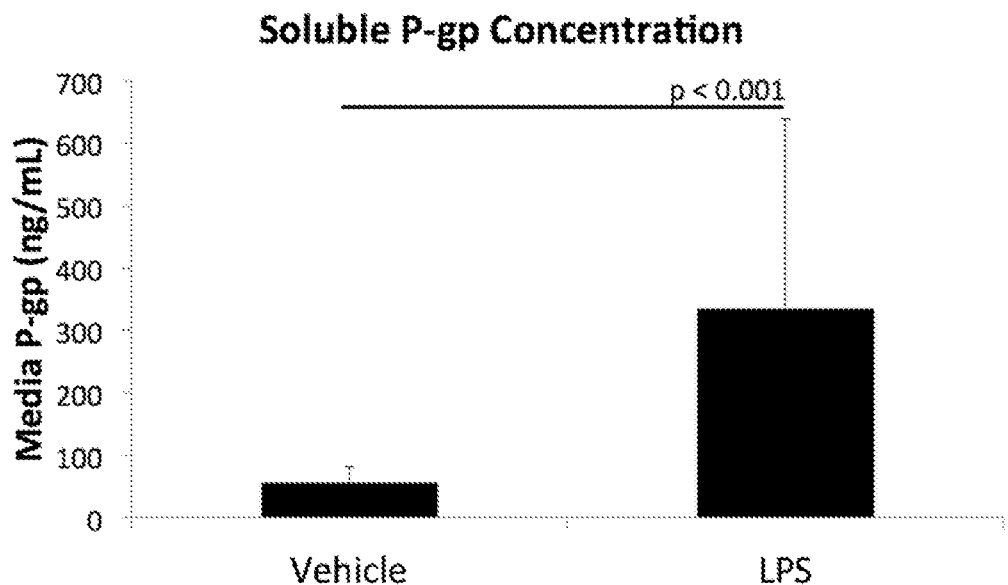
FIGS. 1A-B. A. Concentration of soluble P-gp in media after 24 hours of exposure to vehicle control or LPS (12.5 µg/mL). B. Correlation between cytoplasmic and soluble P-gp in both vehicle control and LPS exposed epithelial cells. Note the apparent upregulation of both the cytoplasmic and soluble P-gp following LPS stimulation.

P-glycoprotein (P-gp) is an ATP dependent transmembrane efflux pump which is upregulated in T-helper cell type 2 (Th2) dominant chronic rhinosinusitis (CRS) endotypes (Bleier et al., Int Forum Allergy Rhinol. 2012; 2 (2):122-5; Feldman et al. Int Forum Allergy Rhinol. 2013; 3 (8):684-7). P-gp may directly contribute to CRS related inflammation through expression dependent promotion of epithelial derived pro-inflammatory cytokine secretion (Bleier et al., Int Forum Allergy Rhinol. 2014; 4 (6):488-94; Bleier et al., Int Forum Allergy Rhinol. 2014; 5 (1):10-13). Previous studies have demonstrated that P-gp may not only reside within the cell membrane but may also be secreted into extracellular fluids (Chu et al., Biochem Biophys Res Commun. 1994; 203 (1):506-12). As P-gp is overexpressed in certain forms of CRS (Bleier et al., Int Forum Allergy Rhinol. 2012; 2 (2):122-5), the secreted form of P-gp can be used as a novel biomarker for the detection of CRS.

The results presented herein confirmed that epithelial cells do secrete P-gp and this secretion is highly correlated to the degree of P-gp expressed within the cell itself. Furthermore, the concentration of both intracellular and secreted P-gp appear to be sensitive to pro-inflammatory stimulation with LPS.

Experiments were performed to determine whether the soluble P-gp detectable in media represented a byproduct of P-gp degradation versus an intact protein as previously reported (Bleier et al., Int Forum Allergy Rhinol. 2012; 2 (2):122-5). Western blot analysis confirmed that while proteolytic byproducts were released into the media at 50 and 60 kDa, the majority of P-gp detected by ELISA was, in fact, the complete 170 kDa protein. Thus, the methods described herein can include detecting only or specifically the full length 170 kDa protein.

As shown herein, the secreted form of P-gp is present in the nasal mucus of both healthy and CRS patients. This confirms the existence of extracellular P-gp as reported in previous studies (Chu et al., Biochem Biophys Res Commun. 1994; 203 (1):506-12; Chiampanichayakul et al., Int J Hematol. 2010; 92 (2):326-33. doi:10.1007/s12185-010-0668-8). The lack of significant correlation between tissue and mucus P-gp levels at low concentrations suggests that P-gp secretion by epithelial cells likely represents a constitutive physiologic process of some unclear purpose. Based in part on previous findings (Feldman et al., Int Forum Allergy Rhinol. 2013; 3 (8):684-7), it was hypothesized that a threshold value of 300 pcg of P-gp/μg of total protein could distinguish physiologic from pathologic secretion and would be associated with a more severe disease phenotype. Patients with P-gp levels exceeding this threshold were considered "high secretors;" they accounted for 25% of patients with any form of CRS included in the present study. Furthermore, among these patients, the secreted P-gp concentration strongly and significantly correlated with tissue levels suggesting that atraumatic mucus sampling may serve as an adequate proxy for determining epithelial P-gp expression within this population.

Previous studies have demonstrated that epithelial P-gp overexpression correlates with Th2 skewed CRS (Bleier et al., Int Forum Allergy Rhinol. 2012; 2 (2):122-5; Feldman et al., Int Forum Allergy Rhinol. 2013; 3 (8):684-7). These results are echoed by the current findings in that high P-gp secreting patients demonstrated a greater proportion of CRSwNP:CRS patients relative to low secretors. Furthermore, high secretors appear to have a greater burden of disease as measured by subjective, histologic, and radiographic endpoints. The fact that the two groups were otherwise similar with respect to age, gender, and comorbidity suggests that their divergence in disease severity may be due to something intrinsic to the underlying pathophysiology of their disease.

As multiple P-gp inhibitors currently exist (see, e.g., Bleier et al., Int Forum Allergy Rhinol. 2014; 5 (1):10-13; Lam et al., Int Forum Allergy Rhinol. 2015; 00 (0):n/a-n/a. doi:10.1002/alr.21454), P-gp secretion status can also be used to predict and identify which patients may benefit from P-gp inhibitory therapies.

Methods for Diagnosing, or Selecting a Subject for Participation, or Stratifying Subjects, in a Clinical Study Provided herein are methods of identifying a subject as having rhinosinusitis, e.g., CRS, or a specific endotype of CRS and selecting a subject for treatment, or for participation in, or stratifying subjects in, a clinical study of a treatment for rhinosinusitis, e.g., CRS. Such methods can include determining a level of P-gp in a sample comprising sinus secretions from a subject, comparing the P-gp level in the sample to a reference P-gp level, and identifying the subject as having rhinosinusitis (e.g., CRS) or selecting for participation a subject having an elevated P-gp level in the sample compared to the reference P-gp level in a clinical trial of a treatment for rhinosinusitis, or stratifying subjects in a clinical trial based on P-gp levels. In some embodiments, a subject can be excluded from participation in a clinical study of a treatment for rhinosinusitis if the subject has no significant change or a decrease in the P-gp level in the sample compared to the reference P-gp level.

Also provided are methods of monitoring the efficacy of a treatment for rhinosinusitis, e.g., CRS. Such methods include determining a P-gp level in a first sample comprising sinus secretions obtained from a subject at a first time point, administering a treatment for CRS, determining a P-gp level in a second sample comprising sinus secretions obtained from the subject at a second time point after administration of at least one dose of the treatment, comparing the P-gp level in the first sample to the P-gp level in the second sample, and determining that the treatment was effecting in a subject having a decreased P-gp level in the second sample compared to the P-gp level in the first sample, or ineffective in a subject having an increased P-gp level in the second sample compared to the P-gp level in the first sample or no change in the P-gp level between the first and second samples.

In some embodiments, the presence and/or level of P-gp is comparable to the presence and/or level of the protein (s) in the disease reference, and the subject has one or more symptoms associated with rhinosinusitis, then the subject has rhinosinusitis. In some embodiments, the subject has no overt signs or symptoms of rhinosinusitis but the presence and/or level of one or more of the proteins evaluated is comparable to the presence and/or level of the protein (s) in the disease reference, then the subject has an increased risk of developing rhinosinusitis. In some embodiments, once it has been determined that a person has rhinosinusitis, or has an increased risk of developing rhinosinusitis, using a method described herein, then a treatment, e.g., as known in the art or as described herein, can be administered.

Suitable reference values can be determined using methods known in the art, e.g., using standard clinical trial methodology and statistical analysis. The reference values can have any relevant form. In some cases, the reference comprises a predetermined value for a meaningful level of P-gp, e.g., a control reference level that represents a normal level of P-gp, e.g., a level in an unaffected subject or a subject who is not at risk of developing a disease described herein, and/or a disease reference that represents a level of the proteins associated with conditions associated with rhinosinusitis e.g., a level in a subject having rhinosinusitis (e.g., CRS).

The predetermined level can be a single cut-off (threshold) value, such as a median or mean, or a level that defines the boundaries of an upper or lower quartile, tertile, or other segment of a clinical trial population that is determined to be statistically different from the other segments. It can be a range of cut-off (or threshold) values, such as a confidence interval. It can be established based upon comparative groups, such as where association with risk of developing disease or presence of disease in one defined group is a fold higher, or lower, (e.g., approximately 2-fold, 4-fold, 8-fold, 16-fold or more) than the risk or presence of disease in another defined group. It can be a range, for example, where a population of subjects (e.g., control subjects) is divided equally (or unequally) into groups, such as a low-risk group, a medium-risk group and a high-risk group, or into quartiles, the lowest quartile being subjects with the lowest risk and the highest quartile being subjects with the highest risk, or into n-quantiles (i.e., n regularly spaced intervals) the lowest of the n-quantiles being subjects with the lowest risk and the highest of the n-quantiles being subjects with the highest risk. In some embodiments, the level of P-gp in the sample is normalized to the amount of protein in the sample. In some embodiments, the reference level is 50, 100, 150, 200, 250, 300, 350, 400, 450, or 500 pcg of P-gp/µg of total protein.

In some embodiments, the predetermined level is a level or occurrence in the same subject, e.g., at a different time point, e.g., an earlier time point.

Subjects associated with predetermined values are typically referred to as reference subjects. For example, in some embodiments, a control reference subject does not have a disorder described herein (e.g. rhinosinusitis). In some cases it may be desirable that the control subject has CRS, and in other cases it may be desirable that a control subject does not have CRS.

A disease reference subject is one who has (or has an increased risk of developing) rhinosinusitis. An increased risk is defined as a risk above the risk of subjects in the general population.

Thus, in some cases the level of P-gp in a subject being less than or equal to a reference level of P-gp is indicative of a clinical status (e.g., indicative of a disorder as described herein, e.g., rhinosinusitis. In other cases the level of P-gp in a subject being greater than or equal to the reference level of P-gp is indicative of the absence of disease or normal risk of the disease. In some embodiments, the amount by which the level in the subject is the less than the reference level is sufficient to distinguish a subject from a control subject, and optionally is a statistically significantly less than the level in a control subject. In cases where the level of P-gp in a subject being equal to the reference level of P-gp the "being equal" refers to being approximately equal (e.g., not statistically different).

The predetermined value can depend upon the particular population of subjects (e.g., human subjects) selected. For example, an apparently healthy population will have a different 'normal' range of levels of P-gp than will a population of subjects which have, are likely to have, or are at greater risk to have, a disorder described herein. Accordingly, the predetermined values selected may take into account the category (e.g., sex, age, health, risk, presence of other diseases) in which a subject (e.g., human subject) falls. Appropriate ranges and categories can be selected with no more than routine experimentation by those of ordinary skill in the art.

In characterizing likelihood, or risk, numerous predetermined values can be established.

In some embodiments, additional clinical evaluation can be used to assist in diagnosing rhinosinusitis (e.g., CRS), or in selecting a subject for participation in, or stratifying subjects in, a clinical study of a treatment for rhinosinusitis. In some embodiments, computed tomography (CT) can be performed to score osteitis in a subject having rhinosinusitis.

The osteitis score, e.g., Kennedy Osteitis Score (KOS) or Global Osteitis Score (GOS) can be used to assist in diagnosing rhinosinusitis (e.g., CRS) or in selecting a subject for participation in, or stratifying subjects in, a clinical study of a treatment for rhinosinusitis. For example, a GOS or KOS above a reference level (in addition to a level of P-gp above a reference level) can indicate that the subject has rhinosinusitis (e.g., CRS), and/or should be treated, selected or stratified.

The clinical studies may be performed by a health care professional (e.g., a physician, a physician's assistant, a nurse, a phlebotomist, or a laboratory technician) in a health care facility (e.g., a hospital, a clinic, or a research center).

Subjects

The methods and compositions described can be used in any subject, but are especially useful in subjects that present with one or more symptoms of rhinosinusitis. The symptoms of rhinosinusitis include nasal congestion and obstruction, colored nasal discharge, anterior or posterior nasal drip. Subjects may also experience facial pain or pressure, and in severe cases, suffer a reduction or a loss of smell (Fokkens et al., 2012). There are two different types of rhinosinusitis: acute and chronic. Acute rhinosinusitis is characterized as rhinosinusitis with complete resolution of symptoms within 12 weeks, while chronic rhinosinusitis lasts longer than 12 weeks, and usually involves tissue damage (Fokkens et al., 2012). Nasal polyps are frequently present in some subjects with chronic rhinosinusitis based on epidemiologic studies.

In the present methods, the subjects are typically mammals, e.g., humans or non-human veterinary subjects, e.g., dogs, cats, horses, pigs, cows, sheep, goats, rabbits, or other animals.

Samples and Assays

The present methods will typically be performed using samples of nasal secretions obtained using methods known in the art. For example, spontaneous secretions can be obtained by collection of the product of nose blowing or collection of secretions dripping out of the nose, suction/microsuction. Collection of the product of nose blowing or suction following stimulation (e.g., using methacholine or histamine) can also be used. Techniques that involve dilution of the nasal secretion into a sample fluid can also be used, e.g., lavage (which may also referred be to as wash or irrigation) such as combined aspiration lavage, spray blow techniques, nasal pool lavage, standard lavage and sequential lavage. A diluted strategy can be used, e.g., a completely non-invasive saline lavage that includes the use of a saline lavage directed into the entire nasal cavity (preferably including the sinuses), e.g., a lavage of at least 50 µL up to about 30 mL, e.g., 50 µL-10 mL, 50 µL-30 mL, 10-30 mL, e.g., 18-25 mL, e.g., 20 mL. Absorptive techniques can include the use of natural or synthetic absorptive materials such as cotton wool, filter paper strips or disks, or cellular materials (foams or sponges such as polyurethane foam or surgical natural (e.g., cellulose) or synthetic sponges, e.g., compressed polyvinylalchohol sponges). See, e.g., Walsh and Falsey, J Infect Dis. 1999 May; 179 (5):1268-73; Riechelmann et al., European Respiratory Journal April 2003, 21 (4)600-605; Ruocco et al., Clin Exp Allergy. 1998 July; 28 (7):881-8; preferably the absorptive material will not significantly bind to proteins present in the sample. An exemplary sponge is a compressed sterile 2×2×5 mm or 2×3×15 mm poly-vinyl-alcohol sponge (e.g., commercially available from Medtronics, and designed to be used in the nose for hemostasis and stenting after sinus surgery or in the setting of nose bleeds). In some embodiments, the sponge is compressed and inserted it into the front of the nasal cavity and it absorbs the mucus through capillary action.

The sponge or lavage can be stored, e.g., at −80° C., preferably in the presence of a biomarker preservative, e.g., a protease inhibitor or nuclease inhibitor (such as RNase inactivating enzymes) until isolation.

Mucus samples can be extracted from the absorptive materials, e.g., by centrifugation or washing.

Exosomes

In some embodiments, the methods include isolating exosomes from the sample, and assaying levels of P-gp in the exosomes. Exosomes are vesicles of about 30-150 nm, surrounded by a lipid bilayer, that have a density of about 1.13-1.19 g/ml. Exosomes have been detected in a wide range of body fluids including blood, lymph, CSF, and urine (Lee et al., *Semin. Immunopathol.* 2011; 1-13; Lee et al., *Hum. Mol. Genet.* 2012; 21:125-134). Biophysically, exosomes are equivalent to cytoplasm enclosed in a lipid bilayer with the external domains of transmembrane proteins exposed to the extracellular environment (Schorey et al., *EMBO Rep.* 2015; 16: 24-43). The biogenesis of exosomes is controlled by the endosomal sorting complex required for transport. These events lead to the development late endosome/multivesicular bodies which can then be recycled back into the plasma membrane and released as exosomes. This process leads to exosomes becoming strongly enriched in markers including the tetraspanins CD63, CD9, CD81, and CD82 which can be used to detect their presence and quantity (Lee et al., Semin. Immunopathol. 2011; 1-13). Exosomes are capable of transporting a wide range of cargo including growth factors and their receptors, DNA, mRNA, and microRNA. Further studies have demonstrated that exosomes are able to shuttle this cargo, including integral membrane proteins such as the chemokine receptor CCR5 (Mack et al., *Nat. Med.* 2000; 6: 769-775), to adjacent cells. Exosome mediated transfer of functional P-gp has also been previously demonstrated in several cell populations including the MCF-7 human breast cancer cell line (Lv et al., *Tumor Biol.* 2014; 10773-10779) and the CCRF-CEM human acute lymphoblastic leukemia cell line (Bebawy et al., Off. J. Leuk. Soc. Am. Leuk. Res. Fund, U. K. 2009; 23: 1643-1649).

A number of methods can be used to isolate nasal mucus derived exosomes from the sample, e.g., centrifugation (e.g., traditional ultracentrifugation (UCF) as described in Théry et al., *Curr. Protoc. Cell Biol.* 2006; Chapter 3: Unit 3.22); chromatography; filtration; polymer-based precipitation; and immunological separation methods; see Yakimchik, Exosomes: isolation and characterization methods and specific markers, 2016-11-30, dx.doi.org/10.13070/mm.en.5.1450, and references cited therein. An exemplary polymer based exosome precipitation system is the ExoQuick from System Biosciences. In an exemplary UCF method, mucus and irrigant samples can be diluted, e.g., in 150 µL of 1× phosphate buffered saline (PBS) with Protease Inhibitor Cocktail. Cellular debris can be pelleted by centrifugation, e.g., at 45 min at 12,000×g at 4° C. The supernatant can then be suspended in PBS, e.g., 4.5 mL of PBS in polypropylene tubes, and ultracentrifuged, e.g., for 2 hours at 110,000×g, at 4° C. The supernatant can then be collected and the pellet resuspended in PBS, e.g., in 4.5 mL 1×PBS. The suspension can be filtered, e.g., through a 0.22-µm filter, and collected in a fresh tube. The filtered suspension can then be centrifuged again, e.g., for 70 min at 110,000×g at 4° C. The supernatant can then be collected and the pellet resuspended in a buffer, e.g., in PBS, e.g., in 200 µl PBS with protease inhibitor.

P-Glycoprotein Assays

P-glycoprotein is a 170-kDa glycoprotein encoded by the MDR1 (ABCB1) gene located on chromosome 7q21.12 and was first identified in the CHO cell line (Fernandez et al., J Pharm. Pharm. Sci. 2004 Nov. 17; 7 (3):359-71). P-gp is a member of the ATP-binding cassette (ABC) transporter family and is capable of energy dependent transport of a variety of intracellular substrates (Golden et al., J Pharm Sci. 2003; 92 (9):1739-53). P-gp is located within the plasma membrane and functions to extrude xenobiotic agents against their concentration gradient (Ehrhardt et al., Pharm. Res. 2003 April; 20 (4):545-51). Substrate recognition of P-gp occurs by a variety of mechanisms including the presence of electron donor groups which bind putative reactive hydrogen bonding sites in the interior channels formed by the 12 transmembrane helices (Golden et al., 2003).

P-gp is constitutively expressed on multiple cell types including the apical membrane of intestinal mucosal cells, the brush border of renal proximal tubules, the blood-brain barrier, and lower airway epithelial cells (Bleier B S, Int. Forum Allergy Rhinol. 2012; 2:122-125). Due to the selective distribution at the port of drug entry and exit, P-gp functions as a biochemical barrier for entry of xenobiotics and as a vacuum cleaner to expel them from the organs, such as brain, liver, kidney, and ultimately from systemic circulation (Varma et al., Pharmacological Research 2003; 48: 347-359). This xenobiotic excretion function belies the role of P-gp in reducing the systemic bioavailability of a variety of drugs. Through increased expression and active drug efflux in malignancy, P-gp has also been shown to confer chemotherapeutic resistance (Fernandez et al., 2004).

Methods known in the art can be used to detect and optionally quantitate levels of P-gp in the sample. Various methods are well known within the art for the identification and/or isolation and/or purification of a biological marker from a sample. An "isolated" or "purified" biological marker is substantially free of cellular material or other contaminants from the cell or tissue source from which the biological marker is derived i.e. partially or completely altered or removed from the natural state through human intervention.

The presence and/or level of a protein can be evaluated using methods known in the art, e.g., using standard electrophoretic and quantitative immunoassay methods for proteins, including but not limited to, Western blot; enzyme linked immunosorbent assay (ELISA); biotin/avidin type assays; protein array detection; radio-immunoassay; immunohistochemistry (IHC); immune-precipitation assay; FACS (fluorescent activated cell sorting); mass spectrometry (Kim (2010) Am J Clin Pathol 134:157-162; Yasun (2012) Anal Chem 84 (14):6008-6015; Brody (2010) Expert Rev Mol Diagn 10 (8):1013-1022; Philips (2014) PLOS One 9 (3): e90226; Pfaffe (2011) Clin Chem 57 (5): 675-687). The methods typically include revealing labels such as fluorescent, chemiluminescent, radioactive, and enzymatic or dye molecules that provide a signal either directly or indirectly. As used herein, the term "label" refers to the coupling (i.e. physically linkage) of a detectable substance, such as a radioactive agent or fluorophore (e.g. phycoerythrin (PE) or indocyanine (Cy5), to an antibody or probe, as well as indirect labeling of the probe or antibody (e.g. horseradish peroxidase, HRP) by reactivity with a detectable substance. A number of antibodies are known in the art that specifically bind to P-gp; commercial sources include Abbexa Ltd; Abbiotec; Abcam; AbD Serotec; Abgent; Abnova Corporation; Acris Antibodies GmbH; AMSBIO LLC; antibodies-online; Atlas Antibodies; BD Biosciences; BioLegend;

Biorbyt; CEDARLANE; Cell Sciences; Creative Diagnostics; Elabscience; EMD Millipore; EXBIO Praha, a.s.; Fitzgerald Industries International; GenWay Biotech, Inc.; Invitrogen Antibodies; LifeSpan BioSciences; MBL International; MyBioSource.com; Nordic BioSite; Novus Biologicals; NSJ Bioreagents; OriGene Technologies; Proteintech Group Inc; Raybiotech, Inc.; Santa Cruz Biotechnology, Inc.; Sino Biological; Source BioScience; SouthernBiotech; Spring Bioscience; Thermo Fisher Scientific; and United States Biological.

In some embodiments, an ELISA method may be used, wherein the wells of a surface such as a microtiter plate are coated with an antibody against which the protein is to be tested. The sample containing or suspected of containing the biological marker is then applied to the wells. After a sufficient amount of time, during which antibody-antigen complexes would have formed, the plate is washed to remove any unbound moieties, and a detectably labelled molecule is added. Again, after a sufficient period of incubation, the plate is washed to remove any excess, unbound molecules, and the presence of the labeled molecule is determined using methods known in the art. Variations of the ELISA method, such as the competitive ELISA or competition assay, and sandwich ELISA, may also be used, as these are well-known to those skilled in the art.

In some embodiments, an IHC method may be used. IHC provides a method of detecting a biological marker in situ. The presence and exact cellular location of the biological marker can be detected. Typically, a sample is fixed with formalin or paraformaldehyde, embedded in paraffin, and cut into sections for staining and subsequent inspection by confocal microscopy. Current methods of IHC use either direct or indirect labelling. The sample may also be inspected by fluorescent microscopy when immunofluorescence (IF) is performed, as a variation to IHC.

Mass spectrometry, and particularly matrix-assisted laser desorption/ionization mass spectrometry (MALDI-MS) and surface-enhanced laser desorption/ionization mass spectrometry (SELDI-MS), is useful for the detection of biomarkers of this invention. (See U.S. Pat. Nos. 5,118,937; 5,045,694; 5,719,060; 6,225,047).

The methods described herein can be performed, for example, by utilizing pre-packaged diagnostic kits comprising at least one antibody or antigen-binding reagent described herein, which may be conveniently used, e.g., in clinical settings, for a method described herein (e.g., diagnosis, subject selection, treatment selection, treatment monitoring, and so on).

Thus also provided herein are kits for detecting the presence of P-gp in a biological sample. For example, the kit can include a compound or agent capable of detecting P-gp protein in a biological sample; and a standard. The compound or agent can be packaged in a suitable container. The kit can further comprise instructions for using the kit to detect P-gp protein in the sample, as well as some or any items necessary for performing the method, e.g., obtaining the sample or containing the sample. When the sample to be used comprises nasal exosomes, the kits can include one or more of: a sponge for sample collection; a delivery device for placing the sponge; a collection container comprising a protease inhibitor and/or RNAse inhibitor (e.g., RNAlater) for sample preservation; sterile saline; and a cold or freezer pack for specimen preservation during shipment.

For example, for antibody-based kits, the kit can include: (1) a first antibody (e.g., attached to a solid support) which binds to a P-gp polypeptide; and, optionally, (2) a second, different antibody which binds to either P-gp or to the first antibody and is conjugated to a detectable agent. In some embodiments, the kit includes a test strip, e.g., a lateral-flow test strip. A number of test strips are known in the art; see, e.g., US PG Pubs 20140370616; 20140206100; 20130295691; 20130189794; 20130059399; 20100285610; 20100024530; 20090246886; 20080160538; 20080081341; 20070105237; 20060275920; and 20030180815.

Treatment of Rhinosinusitis Using P-Glycoprotein Inhibitors

The data presented herein show that the expression of P-gp is present in healthy sinus secretions, but is significantly elevated in secretions from subjects having CRS, with increased levels correlating with severity.

In some embodiments, a subject having rhinosinusitis or chronic rhinosinusitis, e.g., a specific endotype of chronic rhinosinusitis, is identified by a method described herein, and treated by administration to the subject of a standard treatment for sinusitis and/or an effective amount of a P-gp inhibitor. The presence of rhinosinusitis can optionally be confirmed by one of skill in the art based on known methods, e.g., based on detection of the presence of symptoms, by endoscopy, or by computed tomography. The efficacy of the treatment may be monitored by detecting changes in levels of P-gp in sinus secretions and optionally confirmed by methods known in the art, e.g., by monitoring symptoms, by endoscopy or computed tomography. The 22-item Sinonasal Outcomes Test (SNOT-22) is a questionnaire encompassing 22 major symptoms on rhinosinusitis and nasal polyps, and serves as a valuable tool to measure the severity of a subject's symptoms and their impact on health-related quality of life (Quintanilla-Dieck, et al., International Forum of Allergy & Rhinology 2012; 2 (6):437-443). The SNOT-22 assessed 12 nasal- and sinus-related symptoms (nasal blockage, loss of sense of taste and smell; need to blow nose, sneezing, runny nose, cough, postnasal discharge, thick nasal discharge, ear fullness, dizziness, ear pain, and facial pain/pressure) and 10 psychological and behavioral symptoms (difficulty falling asleep, waking up at night, lack of a good night's sleep, waking up tired, fatigue, reduced productivity, reduced concentration, frustrated/restless/irritable, sad, and embarrassed) with participants scoring each symptom on a scale of 0 (absent) to 5 (severe) on average for the last week, for a total score range of 0 to 110. The SNOT-22 score is the mean for the 22 scores (Piccirillo et al., Otolaryngol Head Neck Surg 2002; 126:41-47). The 10-symptom visual analog (VAS) scale is a questionnaire based on the major and minor symptom diagnostic criteria for CRS as described by the American Academy of Otolaryngology—Head and Neck Surgery TFR. The VAS assessed subject-reported severity of each of the following symptoms on average experienced during the prior week: nasal drainage of pus, nasal obstruction/congestion, impaired sense of smell, facial pressure/pain, headache, bad breath, weakness/fatigue, dental pain, ear fullness/pain, and cough (Ryan, et al., Laryngoscope 2011; 121:674-678). The Lund-Kennedy endoscopy scoring system quantifies the pathologic states of the nose and paranasal sinuses as assessed by nasal endoscopy, focusing on the presence of polyps, discharge, edema, scarring or adhesions, and crusting (Ryan, et al., 2011). The Lund Mackay CT scoring system is the most widely used CT grading system for chronic rhinosinusitis. This scoring system consists of a scale of 0-2 dependent on the absence (0), partial (1) or complete (2) opacification of the sinus system and the osteomeatal complex as assessed by CT imaging (Hopkins et al., Otolaryngology—Head and Neck Surgery 2007; 137:555-561). Improvements of the subject include a better symptom score, e.g. a better SNOT-22 or VAS score;

a reduction in inflammation or nasal polyp burden as revealed by endoscopy, e.g. a better Lund-Kennedy score; or a reduction in mucosal thickening or sinus opacification as revealed by computed tomography (CT), e.g. a better Lund-Mackay score.

In some embodiments, the P-gp inhibitor is administered systemically, e.g., orally, intravenously, intradermally, or subcutaneously. In other embodiments, the P-gp inhibitor is administered locally to the subject's nasal passage and sinuses by an inhalation device, by flushing, or by spraying. In some embodiments, a subject identified using a method described herein is treated with nasal drops or sprays comprising an effective amount of a P-gp inhibitor. An effective amount of the P-gp inhibitor can be delivered to the subject's nasal passage and sinuses in a liquid form by flushing or spraying. An effective amount of a P-gp inhibitor can also be delivered to the nasal passage and sinuses of a subject identified using a method described herein in an aerosolized form by an inhalation device, such as a nebulizer, an inhaler, or an OptiNose.

In some embodiments, a subject identified using a method described herein is treated with a P-gp inhibitor in combination with other conventional treatments, e.g., drugs such as corticosteroids and/or antibiotics, to potentiate the effect of treatment. For example, P-gp inhibitors may be used in combination with a corticosteroid selected from dexamethasone, prednisolone, triamcinolone, cortisol, prednisone, budesonide, mometasone, fluticasone, flunisolide, and betamethasone. In some embodiments, P-gp inhibitors are used in combination with an antibiotic selected from macrolides, e.g., erythromycin; penicillins, e.g., amoxicillin, beta-lactam, ampicillin; tetracyclines, e.g., doxycycline, tetracycline; sulfonamides, e.g. mafenide, sulfacetamide; fluoroquinolones; and cephalosporins, e.g., ceftaroline fosamil, ceftobiprole. In some embodiments, P-gp inhibitors are used in combination with a corticosteroid and an antibiotic.

In some embodiments, when a subject identified using a method described herein also has nasal polyps, surgical removal of such nasal polyps can be performed in addition to administration of a P-gp inhibitor to the subject. Thus, the subject may undergo both surgery and treatment with a P-gp inhibitor.

In some embodiments, a P-gp inhibitor-eluting implant, stent, or spacer is used to deliver P-gp to the subject. During a sinus surgery, a P-gp inhibitor eluting device can be implanted, e.g., in the ostia of the paranasal sinuses to prop open the ostia while locally eluting a P-gp inhibitor to reduce inflammation of the sinonasal epithelium after the surgery. The P-gp inhibitor eluting device can be made from bioabsorbable material so that the implant will be absorbed within a short period of time after the implantation and no surgical removal of the implant is necessary. The P-gp inhibitor eluting device can be in the form of solid, semisolid, gel, polymer, or particle. In some embodiments, the P-gp inhibitor eluting device is a bioabsorbable gel such as an alginate gel (e.g., sodium alginate), a cellulose-based gel (e.g., carboxymethyl cellulose or carboxyethyl cellulose), or a chitosan-based gel (e.g., chitosan glycerophosphate; see, e.g., Bleier et al., Am J Rhinol Allergy 23, 76-79, 2009).

In some embodiments, a tissue sample, e.g., a sinus mucosal biopsy sample, can be obtained from a subject having rhinosinusitis and one or more tests can be performed on these biopsy samples to confirm a diagnosis made using a method described herein, to assist in selecting a therapy for the subject. For example, sinus mucosal biopsy samples can be obtained from a subject identified using a method described herein and the average number of eosinophils per high powered field can be calculated, e.g., using light microscopy and staining with hematoxylin and eosin. As demonstrated herein, P-gp expression levels correlate with tissue eosinophilia, thus high levels of tissue eosinophilia (i.e., levels above a reference level) can be used as a proxy for high levels of P-gp expression. A therapy as described herein comprising administration of a P-gp inhibitor can be selected to treat rhinosinusitis in the subject when the average number of eosinophils per high powered field is determined to be above a threshold (i.e., reference level).

In some embodiments, computed tomography (CT) can be performed to score osteitis in a subject having rhinosinusitis. For example, a Kennedy Osteitis Score (KOS) (Lee J T, Kennedy D W, Palmer J N, Am J Rhinol 20:278-282, 2006) or Global Osteitis Score (GOS) (Georgalas C, Videler W, Freling N, Clin Otolaryngol 35:455-461, 2010) can be determined for the bony walls of the paranasal sinuses as previously described. As demonstrated herein, these osteitis scores correlate with P-gp expression level in patients having chronic sinusitis, and thus a high osteitis score can be used as a proxy for high P-gp expression levels. When an osteitis score is determined to be above a threshold (i.e., a reference level), a therapy as described herein comprising administration of a P-gp inhibitor can be selected to treat rhinosinusitis in the subject.

One of skill in the art would readily be able to determine and select a suitable reference level. For example, a reference level can be determined as a median, average, or cutoff point for a percentile of the population (e.g., the cutoff for the top half, top tertile, top quartile, top quintile, and so on). A reference level can be selected that represents a level of P-gp secretion in a sample, eosinophilia, KOS, or GOS in a subject that has CRS, and/or would be likely to benefit from treatment with a P-gp inhibitor, and levels at or above that reference level indicate that the subject has CRS and/or should be treated with a method comprising administration of a P-gp inhibitor as described herein.

P-Glycoprotein Inhibitors

A number of inhibitors of P-gp are known in the art (Varma et al., 2003). In general, P-gp can be inhibited (1) by blocking its substrate binding site; (2) by interfering with its ATPase activity (Shapiro, et al., Biochem Pharmacol 1997; 53:587-96); or (3) by decreasing its expression level either transcriptionally or posttranscriptionally. (Drori et al., Eur J Biochem 1995; 228:1020-9).

Based on specificity and affinity, P-gp inhibitors are classified into four generations. First-generation P-gp inhibitors are known pharmacological compounds that are in clinical use, or were developed for, for other indications but have been shown to inhibit P-gp. These include calcium channel blockers such as verapamil; immunosuppressants like cyclosporin A; anti-hypertensives, reserpine, quinidine and yohimbine; and anti-estrogens like tamoxifen and toremifena (Varma et al., 2003). The usage of these compounds has been limited by their toxicity due to the high serum concentrations achieved with the dose that is required to inhibit P-gp when administered systemically.

Second-generation P-gp modulators are agents that lack the pharmacological activity of the first-generation compounds and usually possess a higher P-gp affinity. Second-generation P-gp inhibitors include the non-immunosuppressive analogues of cyclosporin A such as PSC 833 (Valspodar: 6-[(2S,4R,6E)-4-methyl-2-(methylamino)-3-oxo-6-octenoic acid]-7-L-valine-cyclosporin A); verapamil isomers such as D-isomer of verapamil, R-verapamil, and dexverapamil; and other inhibitors such as VX-710 (Biricodar: 1,7-di (pyridin-3-yl)heptan-4-yl (2S)-1-[oxo (3,4,5- trimethoxyphenyl)acetyl]piperidine-2-carboxylate); GF120918 (Elacridar: N-(4-(2-(6,7-dimethoxy-3,4-dihydroisoquinolin-2 (1H)-yl)ethyl)phenyl)-5-methoxy-9-oxo-9, 10-dihydroacridine-4-carboxamide hydrochloride); and MS-209 (Dofequidar fumarate: 1-(4-(2-hydroxy-3-(quinolin-5-yloxy)propyl)piperazin-1-yl)-2,2-diphenylethanone) (Varma et al., 2003). However, this class of compounds often inhibits two or more ABC transporters, leading to some drug-drug interactions.

The third-generation P-gp blockers are under development with the primary purpose to improve the treatment of multidrug resistant tumors and to inhibit P-gp with high specificity and toxicity. Examples of the third-generation P-gp inhibitors include LY335979 (Zosuquidar: (2R)-1-{4-[(1aR,6r,10bS)-1,1-Difluoro-1,1a,6,10b-tetrahydrodibenzo [a,e]cyclopropa[c]cyclohepten-6-yl]piperazin-1-yl}-3-(quinolin-5-yloxy)propan-2-ol,trihydrochloride); OC144093 (4-[2-[4-[(E)-3-ethoxyprop-1-enyl]phenyl]-4-[4-(propan-2-ylamino)phenyl]-1H-imidazol-5-yl]-N-propan-2-ylaniline); R-101933 (Laniquidar: methyl 11-(1-(4-(quinolin-2-yl-methoxy)phenethyl)piperidin-4-ylidene)-6,11-dihydro-5H-benzo[d]imidazo[1,2-a]azepine-3-carboxylate); XR9576 (Tariquidar: N-[2-[[4-[2-(6,7-Dimethoxy-3,4-dihydro-1H-isoquinolin-2-yl)ethyl]phenyl]carbamoyl]-4,5-dimethoxyphenyl]quinoline-3-carboxamide); XR9051 (3-((Z)-((Z)-5-benzylidene-4-methyl-3,6-dioxopiperazin-2-ylidene) methyl)-N-(4-(2-(6,7-dimethoxy-3,4-dihydroisoquinolin-2 (1H)-yl)ethyl)phenyl)benzamide). Some third-generation P-gp modulators such as LY335979, OC144093, and XR9576 are shown to be highly potent and selective inhibitors of P-gp with a potency of about 10-fold more than the first and second-generation inhibitors. (Varma et al., 2003).

Fourth generation compounds include natural-source compounds (e.g., marine-source as described in Lopez and Martinez-Luis, Mar Drugs. 2014 January; 12 (1): 525-546, or flavonoids, alkaloids (e.g., *Strychnos* alkaloids (e.g., compound 7 in Munagala et al., Bioorganic & Medicinal Chemistry, 22 (3):1148-1155 (2014)), coumarins, cannabinoids, taccalonolides, diterpenes (e.g., taxanes), sesquiterpenes, triterpenes, ginsenosides, lignans, polyenes and polyacetylenes as described in Palmeira et al., Current Medicinal Chemistry, 2012, 19, 1946-2025); peptides and peptidomimetics, e.g., reversins such as reversin 121, peptide 15, and diketopiperazine XR9051; and dual ligands, e.g., aminated thioxanthones such as 1-[2-(1H-benzimidazol-2-yl) ethanamine]-4-propoxy-9H-thioxanthen-9-one; see, e.g., Palmeira et al., Current Medicinal Chemistry, 2012, 19, 1946-2025.

Pharmaceutical Compositions, Dosage, and Methods of Administration

The methods of treatment described herein also include the use of pharmaceutical compositions, which include P-gp inhibitors described herein as active ingredients. In some embodiments the composition also includes one or more supplementary active compounds incorporated therein, e.g., one or more corticosteroids and/or one or more antibiotics. The corticosteroid can be, e.g., selected from dexamethasone, prednisone, prednisolone, triamcinolone, cortisol, budesonide, mometasone, fluticasone, flunisolide, or betamethasone. The antibiotic can be, e.g., selected from erythromycin, doxycycline, tetracycline, penicillin, beta-lactam, macrolide, fluoroquinolone, cephalosporin, and sulfonamide. Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

Pharmaceutical compositions are typically formulated to be compatible with its intended route of administration. Examples of routes of administration include parenteral, e.g., intravenous, intradermal, subcutaneous, oral (e.g., inhalation), transdermal (topical), transmucosal, and rectal administration.

Methods of formulating suitable pharmaceutical compositions are known in the art, see, e.g., *Remington: The Science and Practice of Pharmacy,* 22nd ed., Allen Ed. Mack Publishing Co., Easton, Pa., 2012; and the books in the series *Drugs and the Pharmaceutical Sciences: a Series of Textbooks and Monographs* (Dekker, N.Y.). For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use can include sterile aqueous solutions (where water soluble) or dispersions and sterile powders, for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Systemic administration of a therapeutic compound as described herein can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the therapeutic compounds are prepared with carriers that will protect the therapeutic compounds against rapid elimination from the body, such as a controlled release formulation, including implants and microencapsulated delivery systems.

The pharmaceutical compositions can be included in a container, pack, or dispenser together with instructions for administration.

In some embodiments, a kit for treating rhinosinusitis in a subject is provided. Such a kit comprises a pharmaceutical composition comprising an effective amount of a P-glycoprotein inhibitor, optionally a corticosteroid and/or an antibiotic, and a device for delivering the pharmaceutical composition to the subject's nasal passage and sinuses, such as a nebulizer, an inhaler, or an OptiNose. The device may deliver the pharmaceutical composition to the subject's nasal passage and sinuses in a liquid or an aerosolized form.

In non-limiting examples, the pharmaceutical composition containing at least one pharmaceutical agent is formulated as a liquid (e.g., a thermosetting liquid), as a component of a solid (e.g., a powder or a biodegradable biocompatible polymer (e.g., a cationic biodegradable biocompatible polymer)), or as a component of a gel (e.g., a biodegradable biocompatible polymer). In some embodiments, the at least composition containing at least one pharmaceutical agent is formulated as a gel selected from the group of an alginate gel (e.g., sodium alginate), a cellulose-based gel (e.g., carboxymethyl cellulose or carboxyethyl cellulose), or a chitosan-based gel (e.g., chitosan glycerophosphate). Additional, non-limiting examples of drug-eluting polymers that can be used to formulate any of the pharmaceutical compositions described herein include, carrageenan, carboxymethylcellulose, hydroxypropylcellulose, dextran in combination with polyvinyl alcohol, dextran in combination with polyacrylic acid, polygalacturonic acid, galacturonic polysaccharide, polysalactic acid, polyglycolic acid, tamarind gum, xanthum gum, cellulose gum, guar gum (carboxymethyl guar), pectin, polyacrylic acid, polymethacrylic acid, N-isopropylpolyacrylomide, polyoxyethylene, polyoxypropylene, pluronic acid, polylactic acid, cyclodextrin, cycloamylose, resilin, polybutadiene, N-(2-Hydroxypropyl)methacrylamide (HPMA) copolymer, maleic anhydrate-alkyl vinyl ether, polydepsipeptide, polyhydroxybutyrate, polycaprolactone, polydioxanone, polyethylene glycol, polyorganophosphazene, polyortho ester, polyvinylpyrrolidone, polylactic-co-glycolic acid (PLGA), polyanhydrides, polysilamine, poly N-vinyl caprolactam, and gellan.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a therapeutic compound (i.e., an effective dosage) depends on the therapeutic compounds selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the therapeutic compounds described herein can include a single treatment or a series of treatments.

Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

EXAMPLES

The invention is further described in the following examples, which do not limit the scope of the invention described in the claims.

Example 1. Intact Soluble P-Glycoprotein is Secreted by Sinonasal Epithelial Cells P-glycoprotein (P-gp) is a 170 kDa trans-membrane efflux pump which is upregulated in chronic rhinosinusitis (CRS). Studies in leukemia have demonstrated that P-gp may also be secreted in an intact soluble form. The purpose of this study was to explore whether sinonasal epithelial cells were capable of secreting soluble P-gp and whether it has any functional role.

Methods

The following Materials and Methods were used in Example 1.

Epithelial Cell Procurement

Procurement of the sinus mucosal biopsies used to generate the human sinonasal epithelial cell cultures (HSNECCs) was approved by the Massachusetts Eye and Ear Infirmary Institutional Review Board. Samples were taken from patients with healthy sinus tissue (ie. controls) undergoing endoscopic sinus surgery for orbital or skull base pathologies and from patients diagnosed with CRS according to EPOS' criteria. Exclusion criteria included ciliary dysfunction, autoimmune disease, cystic fibrosis, or any known immunodeficiency.

Human Sinonasal Epithelial Cell Culture

HSNECCs from 7 control patients and 6 CRS patients were grown as previously described[8]. Briefly, mucosal samples were washed and digested in Pronase for 90 minutes at 37° C. Cell suspensions were separated from particulate matter by centrifugation and resuspended in bronchial epithelial growth media (BEGM). Cells were plated for 2 hours on standard tissue culture plates to remove contaminating fibroblasts. Cells were then expanded for 3-5 days on human collagen type IV-coated (Collagen from human placenta, Bornstein and Traub Type IV, Sigma Aldrich, St. Louis, Mo.) 75 cm$^2$ dishes (Corning Life Sciences, Corning, N.Y.). Once confluent, the HSNECCs were trypsinized and re-seeded evenly in human collagen type IV-coated black walled 24-well (PerkinElmer, Cambridge, Mass.) or 96-well (Corning 96 well Plates) tissue culture plates for 24 hours in BEGM prior to analysis. CRS derived HSNECCs were exposed to media (vehicle control) or lipopolysaccharide (LPS, 12.5 μg/mL, Sigma Aldrich) for 24 hours prior to media and cytoplasm collection. Control patient derived cells were exposed to recombinant human P-glycoprotein (USCN Life Sciences Inc., Wuhan, P.R. China) at doses ranging from 100-2000 ng/mL for 24 hours prior to performing the immunohistochemistry or calcein acetoxymethyl ester (AM) assay described below.

Quantification of Cytoplasmic and Soluble P-Glycoprotein

Media was collected from the CRS derived wells after vehicle control or LPS exposure. Contaminating debris and non-adherent cells were removed by centrifugation (950 rpm for 3 minutes). The cytoplasmic protein fraction was isolated using the Native Membrane Protein Extraction kit (Proteoextract, Billerica, Mass.). P-glycoprotein concentration within the media and cytoplasmic fractions were quantified using a commercially available enzyme-linked immunosorbent assay (ELISA) (USCN Life Sciences Inc.).

Protein Extraction and Western Blot Analysis

Western blot was used to determine the molecular weight of the soluble P-glycoprotein released into the media from the CRS derived epithelial cells. After centrifugation to remove contaminating cells and debris as described above, the amount of total protein in the supernatant was determined using a Micro BCA assay Kit (Pierce, Rockford, Ill.). 10 μg of total protein and Laemmli loading buffer (2× Laemmli sample buffer, Bio-Rad, Hercules, Calif., with β-mercaptoethanol, Sigma, St. Louis, Mo.) were denatured at 95° C. for 3 minutes and separated on precast NOVEX® 4-20% Tris-Glycine Mini Protein Gels (1.0 mm, 9 wells, Life Technologies) (polyacrylamide gels based on traditional Laemmli protein electrophoresis, which allows the use of Laemmli sample and running buffers). The protein was transferred onto a polyvinylidene fluoride membrane by IBLOT® Dry Blotting System (Invitrogen, Carlsbad, Calif.) (Western blot transfer system). The membrane was blocked with 1% milk in Tris buffered saline and Tween-20 (TBST, Sigma Aldrich) for 30 minutes at room temperature. The primary antibody (Monoclonal Anti-P-glycoprotein Clone F4, 1:2000, in 1% milk in TBST) was added and incubated at 4° C. overnight. After 3 washes of 15 minutes with TBST, the secondary antibody (Anti-Mouse IgG (Fab specific)—Peroxidase antibody produced in goat in 1% milk in TBST, Sigma) was incubated for 1 hour at room temperature. The membrane was washed again 3 times of 15 minutes with TBST and SuperSignal™ West Pico Chemiluminescent Substrate (Life Technologies) was applied for 5 minutes before visualization with ChemiDoc MP (Bio-Rad). Recombinant P-gp (USCN Life Sciences Inc., Wuhan, P.R. China) was used as a control and a monoclonal anti-GAPDH antibody produced in mouse (Sigma Aldrich) was used as a loading control.

Quantitative Fluorescent Immunocytochemistry

Fluorescent immunocytochemistry for membranous P-gp interpolation following recombinant P-gp exposure was performed using previously described techniques[8]. Following blocking, a primary antibody to the P-gp extracellular epitope (Monoclonal Anti-P-glycoprotein Clone F4, 1:250; Sigma Aldrich) was applied for 24 hours at 4° C. The cells were then rinsed, followed by application of the Cy3 (Cy™3 AffiniPure F (ab')$_2$ Fragment Goat Anti-Mouse IgG, 1:100; Jackson Immunoresearch, West Grove, Pa.) or FITC (Anti-Mouse IgG [Fc-specific] F (ab)$_2$ fragment-FITC, 1:160) conjugated secondary antibody for 30 minutes at room temperature. The wells were then rinsed 3 times and imaged in phosphate buffered saline. Negative control wells were considered those in which the primary antibody was omitted from the staining procedure.

Fluorescent staining intensity was quantified according to previously described techniques[9]. Briefly, 20× fields were chosen and images were analyzed in Image J v1.49t. The cells and 3 background areas were circled in Image J using the free hand sections tool and the integrated density, area of selected cell, and mean fluorescence of the backgrounds were measured using the region of interest (ROI) manager. The corrected total cell fluorescence (CTCF) was calculated as the integrated density−(area of selected cell×mean fluorescence of background readings). CTCF values were averaged by well and then averaged across patients.

Calcein AM P-Glycoprotein Activity Assay

A calcein AM assay was performed to determine whether the interpolated P-gp was functional following 24 hours of recombinant P-gp exposure as described above. Pre-warmed calcein AM (Life Technologies) was added to each well for a final calcein concentration of 2.5 µM as previously described[4]. After 15 minutes, each well was washed 3 times with cold phosphate buffered saline and the calcein fluorescence within each well was quantified using a spectrophotometer (Molecular Devices SpectraMax M5, Sunnyvale, Calif.) at an excitation and emission wavelength of 494 nm and 517 nm, respectively. A decrease in fluorescence was considered an indication of increased P-gp function as previously described[4].

Statistical Analysis

All studies were performed in technical duplicates. Normality was assessed using the Shapiro-Wilk test. In vitro P-gp secretion in the presence or absence of LPS was compared using a Kruskal-Wallis non-parametric test. The correlation between soluble and cytoplasmic P-gp was determined using a Spearman's rank correlation coefficient. The changes in CTCF and calcein fluorescence following recombinant P-gp exposure were compared using a 2-tailed Student's t-test. A p-value of less than 0.05 was considered significant.

Example 1.1 In Vitro Soluble P-Glycoprotein Secretion

Figure 1B:
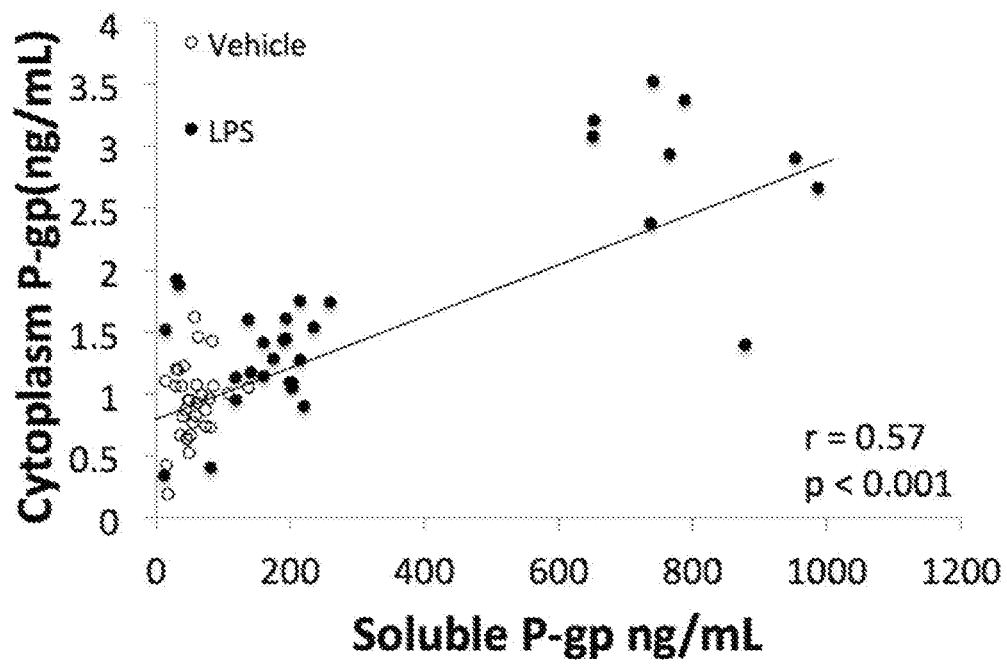

Among the vehicle control CRS derived epithelial cultures (n=6), soluble P-gp was detected at a concentration of 55.43+/−26.26 ng/mL (mean+/−SD). P-gp secretion significantly increased to a concentration of 333.27+/−305.98 ng/mL (p<0.001) following stimulation with LPS (n=6) (FIG. 1A). The concentration of soluble P-gp across all conditions strongly and significantly correlated with the cytoplasmic P-gp concentration within the same well (r=0.57, p=0.000001) (FIG. 1B).

Example 1.2 Western Blot Analysis

Figure 2:
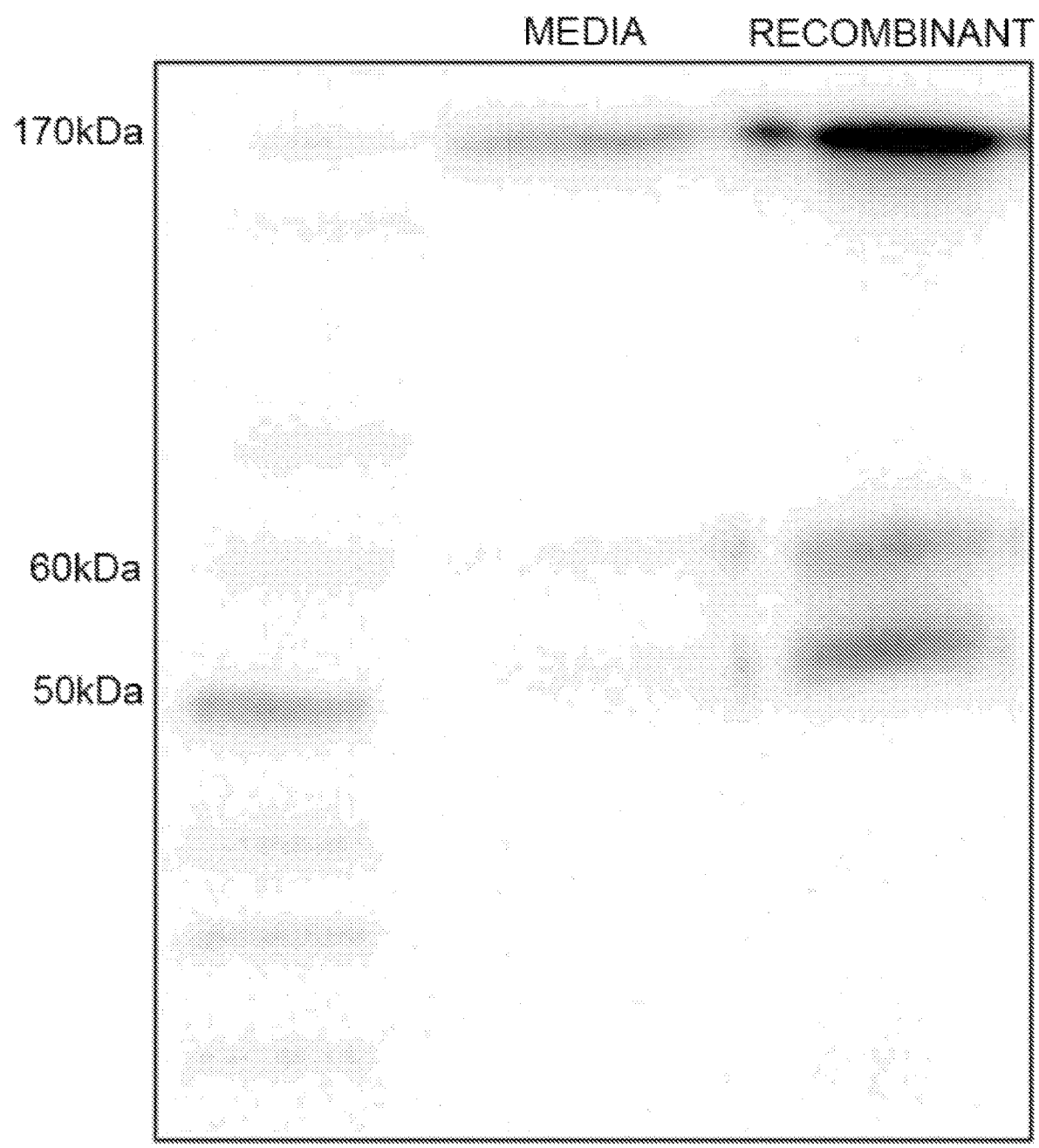
FIG. 2. Western blot confirming that a significant proportion of the soluble P-gp detected within the media in FIG. 1 is secreted intact as evidenced by the strong band at 170 kDa which correlates with the molecular weight of the native protein. Additional degradation bands are seen at both 50 and 60 kDa.

Western blot analysis of the culture media following 24 hours of incubation with control primary epithelial cells revealed a band of intact P-gp at 170 kDa which correlated with the positive recombinant P-gp control lane. Similarly, in both the conditioned media and recombinant P-gp lanes, degradation products were observed at approximately 50 and 60 kDa) (FIG. 2).

Example 1.3 Membranous Interpolation and Function of Recombinant P-Glycoprotein

Figure 3:
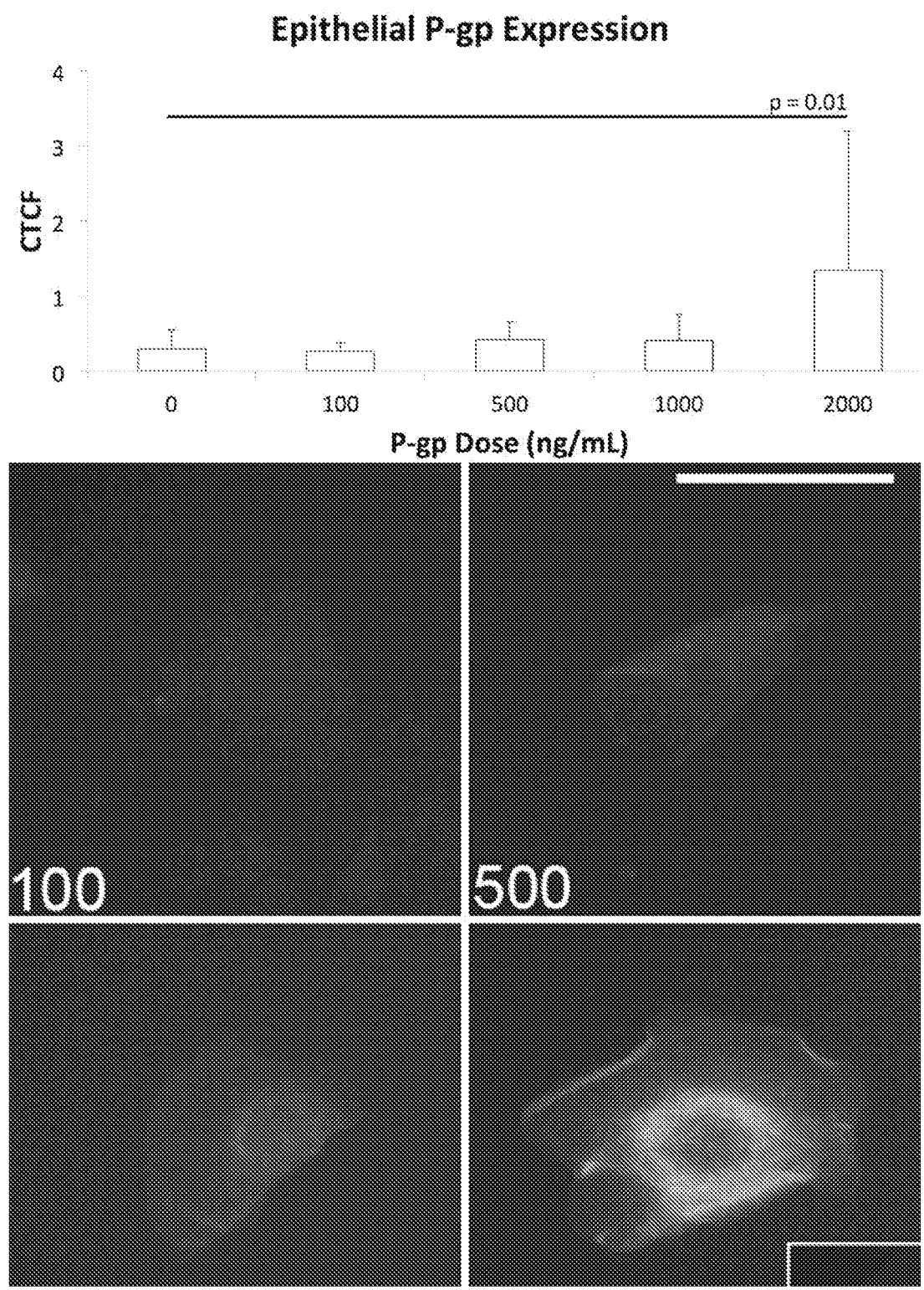
FIG. 3. Histogram of fluorescent P-gp staining intensity (CTCF—corrected total cell fluorescence) in epithelial culture demonstrating a dose response following exposure to exogenous recombinant human P-gp. Images demonstrate representative fluorescent immunocytochemical staining of epithelial cells at the same recombinant P-gp doses as the histogram (inset represent vehicle control, bar=10 µm).
Figure 4:
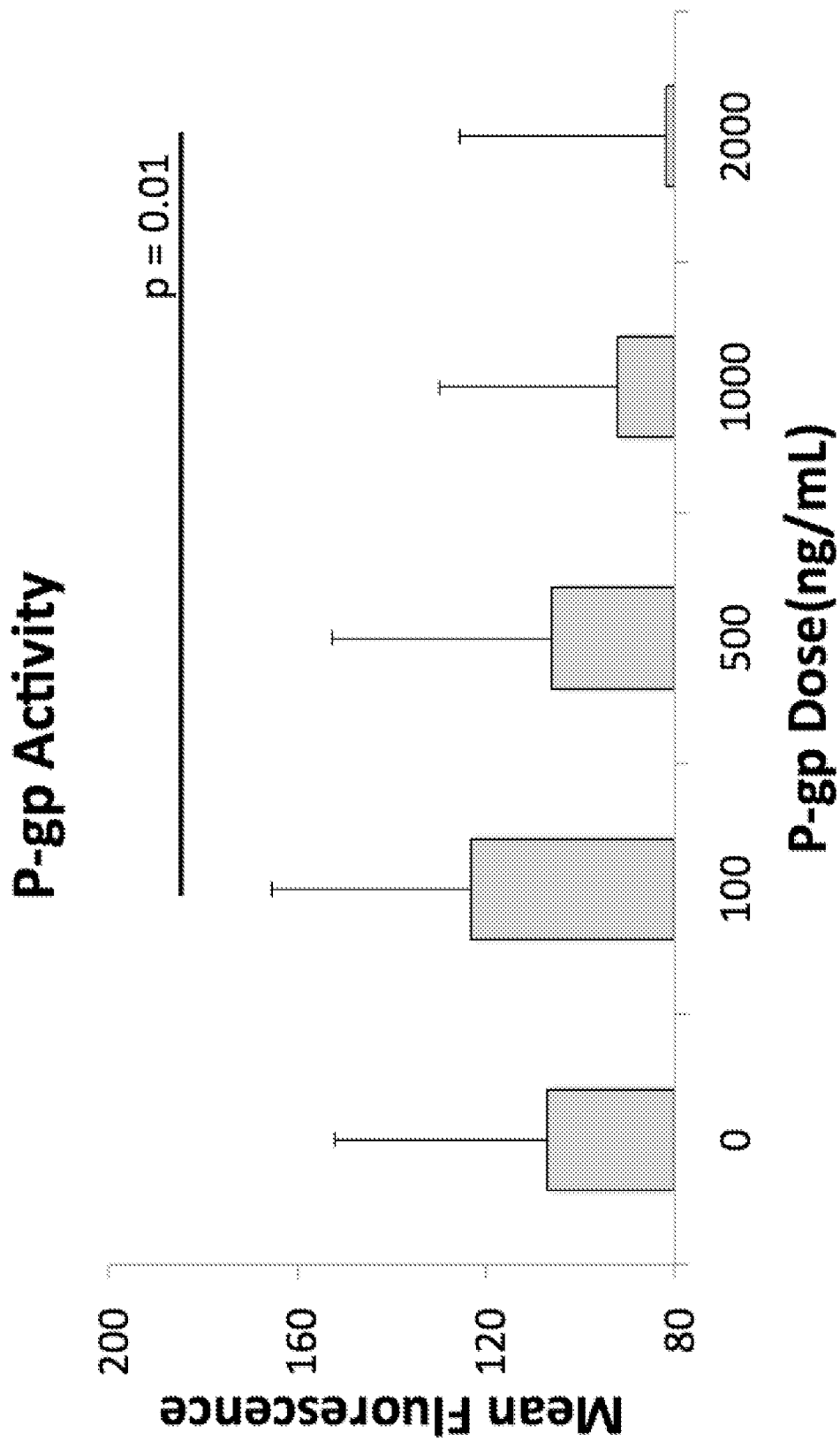
FIG. 4. Calcein AM functional P-gp assay in epithelial cells following recombinant P-gp exposure. A dose response is evident with increasing P-gp function with higher recombinant doses as demonstrated by a decrease in calcein fluorescence.

The baseline mean CTCF among the healthy patient derived epithelial cell cultures was 0.29+/−0.26 (n=7). A successive dose dependent increase in CTCF was observed following exposure to 100-2000 ng/mL of exogenous recombinant human P-gp. The CTCF at 2000 ng/mL (1.34+/−1.85, n=7) was significantly greater than that of the vehicle control wells (p=0.01) (FIG. 3). These findings correlated with the qualitative fluorescent immunocytochemical results (FIG. 3). Similarly, the calcein AM functional P-gp assay revealed a dose response with a significant reduction in mean fluorescence between the 100 ng/mL dose (123.11+/−42.16, n=7) and the 2000 ng/mL dose (82.03+/−43.69, n=7, p=0.01) (FIG. 4).

This study demonstrates that cultured sinonasal epithelial cells are able to both secrete an intact form of P-gp and functionally interpolate exogenous P-gp into their cell membrane. While the mechanism of this P-gp cycling remains unclear, the current in vitro findings suggest that soluble P-gp may be present in nasal mucus as a potential biomarker and could participate in the maintenance of P-gp overexpression in CRS. Future efforts will be directed towards quantifying soluble P-gp in vivo and exploring the pathways involved in its secretion and uptake.

REFERENCES FOR EXAMPLE 1

1. Chiampanichayakul S, Anuchapreeda S, Chruewkamlow N, Mahasongkram K, Thanaratanakorn P, Kasinrerk W. Production of monoclonal antibodies to P-glycoprotein: its application in detection of soluble and surface P-glycoprotein of leukemia patients. *Int J Hematol.* 2010; 92 (2):326-33. doi:10.1007/s12185-010-0668-8.
2. Bleier B S, Article O. Regional expression of epithelial MDR1/P-glycoprotein in chronic rhinosinusitis with and without nasal polyposis. *Int Forum Allergy Rhinol.* 2012; 2 (2):122-5. doi:10.1002/alr.21004.
3. Feldman R E, Lam A C, Sadow P M, Bleier B S. P-glycoprotein is a marker of tissue eosinophilia and radiographic inflammation in chronic rhinosinusitis without nasal polyps. *Int Forum Allergy Rhinol.* 2013; 3 (8):684-7. doi:10.1002/alr.21176.
4. Bleier B S, Nocera A L, Iqbal H, et al. P-glycoprotein promotes epithelial T helper 2-associated cytokine secretion in chronic sinusitis with nasal polyps. *Int Forum Allergy Rhinol.* 2014; 4 (6):488-94. doi:10.1002/alr.21316.
5. Bleier B S, Kocharyan A, Singleton A, Han X. Verapamil modulates interleukin-5 and interleukin-6 secretion in organotypic human sinonasal polyp explants. *Int Forum Allergy Rhinol.* 2014; 5 (1):10-13. doi:10.1002/alr.21436.
6. Chu T M, Lin T H, Kawinski E. Detection of soluble P-glycoprotein in culture media and extracellular fluids. *Biochem Biophys Res Commun.* 1994; 203 (1):506-12. doi:10.1006/bbrc.1994.2211.
7. Fokkens W J, Lund V J, Mullol J, et al. European Position Paper on Rhinosinusitis and Nasal Polyps 2012. *Rhinol Suppl.* 2012; (23):3 p preceding table of contents, 1-298. Available at: ncbi.nlm.nih.gov/pubmed/22764607. Accessed Feb. 11, 2014.
8. Bleier B S, Nocera A L, Iqbal H, Hoang J D, Feldman R E, Han X. P-glycoprotein functions as an immunomodulator in healthy human primary nasal epithelial cells. *Int Forum Allergy Rhinol.* 2013; 3 (6):433-8. doi:10.1002/alr.21166.
9. McCloy R a., Rogers S, Caldon C E, Lorca T, Castro A, Burgess A. Partial inhibition of Cdk1 in G2 phase overrides the SAC and decouples mitotic events. *Cell Cycle.* 2014; 13 (9):1400-1412. doi:10.4161/cc.28401.
10. Wioland M A, Fleury-Feith J, Corlieu P, et al. CFTR, MDR1, and MRP1 immunolocalization in normal human nasal respiratory mucosa. *J Histochem Cytochem.* 2000; 48:1215-1222. doi:10.1177/002215540004800905.
11. Kandimalla K K, Donovan M D. Localization and differential activity of P-glycoprotein in the bovine olfactory and nasal respiratory mucosae. *Pharm Res.* 2005; 22 (7):1121-8. doi:10.1007/s11095-005-5420-3.
12. Wolking S, Schaeffeler E, Lerche H, Schwab M, Nies A T. Impact of Genetic Polymorphisms of ABCB1 (MDR1, P-Glycoprotein) on Drug Disposition and Potential Clinical Implications: Update of the Literature. *Clin Pharmacokinet.* 2015; 54 (7):709-35. doi:10.1007/s40262-015-0267-1.

13. Henrique R, Oliveira A I, Costa V L, et al. Epigenetic regulation of MDR1 gene through post-translational histone modifications in prostate cancer. BMC Genomics. 2013; 14:898. doi:10.1186/1471-2164-14-898.

Example 2. Secreted P-Glycoprotein is a Non-Invasive Biomarker of Chronic Rhinosinusitis The discovery of non-invasive biomarkers of Chronic Rhinosinusitis (CRS) endotypes is critical to advance our ability to provide prognostic information and targeted medical therapy. Epithelial P-glycoprotein (P-gp) is overexpressed in CRS and exists in an extracellular, secreted form. The purpose of this study was to determine whether 1) secreted P-gp could be detected in nasal mucus and 2) whether a threshold value of secreted P-gp could be used to predict CRS endotype and disease severity.

Methods

The following Materials and Methods were used in Example 2.

Sinonasal Mucus and Mucosal Tissue Procurement

The procurement of all patient samples used in this study was approved by the Massachusetts Eye and Ear Infirmary Institutional Review Board. Mucus samples were taken from patients undergoing sinonasal surgery by placing a compressed polyvinyl alcohol sponge (Medtronic, Minneapolis, Minn.) against the ethmoid bulla for 5 minutes taking care not to abrade the mucosa or contaminate the sponge with blood. After sponge removal, mucosal tissue samples were taken from the adjacent ethmoid bulla. Both samples were immediately frozen and stored at −80° C. for batched analysis. Samples were taken from healthy control patients undergoing endoscopic sinus surgery for orbital or skull base pathologies and from patients diagnosed with Chronic Rhinosinusitis (CRS) with or without Nasal Polyps (NP) according to EPOS[11] criteria. Exclusion criteria included ciliary dysfunction, autoimmune disease, cystic fibrosis, or any known immunodeficiency.

Sinonasal Mucus and Mucosal Tissue Protein Quantification

After thawing, mucus samples were extracted from the sponge by centrifugation (1500 g at 4° C. for 30 minutes). The mucus was then diluted in 1200 uL of 1× phosphate buffered saline (PBS, Life Technologies, Carlsbad, Calif.) with Protease Inhibitor Cocktail (1:100, Sigma, St. Louis, Mo.). Cellular debris were pelleted out following 10 minutes of additional centrifugation (17,000 g at 4° C.). Mucosal tissue samples were thawed and rinsed with 1×PBS prior to protein extraction using CelLytic MT (Sigma, with 1:100 Protease Inhibitor Cocktail). The tissue and CelLytic MT solution were homogenized for 60 seconds and then incubated at 4° C. for 15 minutes. Tissue debris were pelleted by centrifugation at 17,000 g at 4° C. for 10 minutes. The supernatant was then collected for analysis. The total protein concentration within the mucus and tissue samples were determined using a Micro BCA Protein Assay Kit (Pierce, Rockford, Ill.). P-gp and eMBP concentrations within the mucus and tissue samples were quantified using commercially available enzyme-linked immunosorbent assays (ELISA) (USCN Life Sciences Inc, Wuhan, China). Final P-gp and eMBP concentrations were corrected for dilution and normalized to the total protein concentration within the same sample.

Quantification of Clinical Disease Severity

Clinical indicators of disease severity were measured according to previously described methods. The validated 22 item Sino-Nasal Outcomes Test (SNOT-22)[12] was administered to all patients upon presentation. Computed tomography (CT) severity scores were graded by two independent and blinded observers according to the Lund-Mackay method[13]. Tissue eosinophilia in each patient was quantified using two representative hematoxylin and eosin slides generated as part of their routine pathologic analysis. The number of eosinophils per five 400× high powered fields (hpf) were recorded by two independent and blinded observers as previously described[7]. The values were averaged to generate a mean eosinophil per hpf score for each patient.

Statistical Analysis

All samples were analyzed in duplicate. Normality was assessed using the Shapiro-Wilk test and the data was found to be uniformly non-parametric. Continuous variables between groups were compared using the Mann-Whitney U test. Correlations between P-gp and eMBP values were performed using the Spearman's rank-order correlation test. Patient demographics between groups were compared using the chi-square test. A p-value of less than 0.05 was considered statistically significant.

Example 2.1 Patient Demographics

Our population consisted of 38 patients (10 Control, 16 CRS, and 12 CRSwNP) with subjective and objective diseases severity indices that varied as expected by diagnosis. The mean SNOT-22 scores among the control patients (12.6+/−14.2, mean+/−SD) were significantly lower than those of the CRS (43.4+/−22.8, p=0.007) and CRSwNP patients (53.4+/−25.5, p=0.002). The mean eosinophils/hpf among the control patients (0.3+/−0.5) were significantly lower than those of the CRS (5.5+/−7.4, p=0.002) and CRSwNP patients (70.5+/−74.2, p<0.001). Similarly, the Lund-Mackay scores among the control patients (0.8+/−1.0) were significantly lower than those of the CRS (4.8+/−4.2, p=0.003) and the CRSwNP patients (16.7+/−7.6, p=0.002) (FIGS. 5A-C). A cutoff of 300 pcg of secreted P-gp/µg of total protein was established to differentiate a low versus high P-gp secretor population. There were no significant differences between low and high secretors with respect to age, gender, or the prevalence of asthma and environmental allergy (Table 1).

TABLE 1

Patient demographics by secretor status demonstrating no significant difference between groups.
Patient Demographics

| Variable | Low Secretors (N = 31) | High Secretors (N = 7) | p-value |
| --- | --- | --- | --- |
| Age-Years(+/−SD) | 50.1 (18.9) | 45.6 (7.4) | 0.43 |
| Gender-No. (%) | | | |
| Male | 16 (51.6) | 3 (42.9) | 1.0 |
| Female | 15 (48.4) | 4 (57.1) | 1.0 |
| Asthma-No. (%) | 8 (25.8) | 4 (57.1) | 0.18 |
| Allergy-No. (%) | 10 (32.3) | 2 (28.6) | 1.0 |

Example 2.2 Quantification of Secreted P-Glycoprotein

Secreted P-gp was detected in both the mucus and mucosal tissue samples of all 38 patients tested, regardless of their clinical diagnosis. Among the low secreting patients (n=31), there was no significant correlation between secreted and mucosal P-gp concentrations (r=−0.24, p=NS).

Figures 6A, 6B:
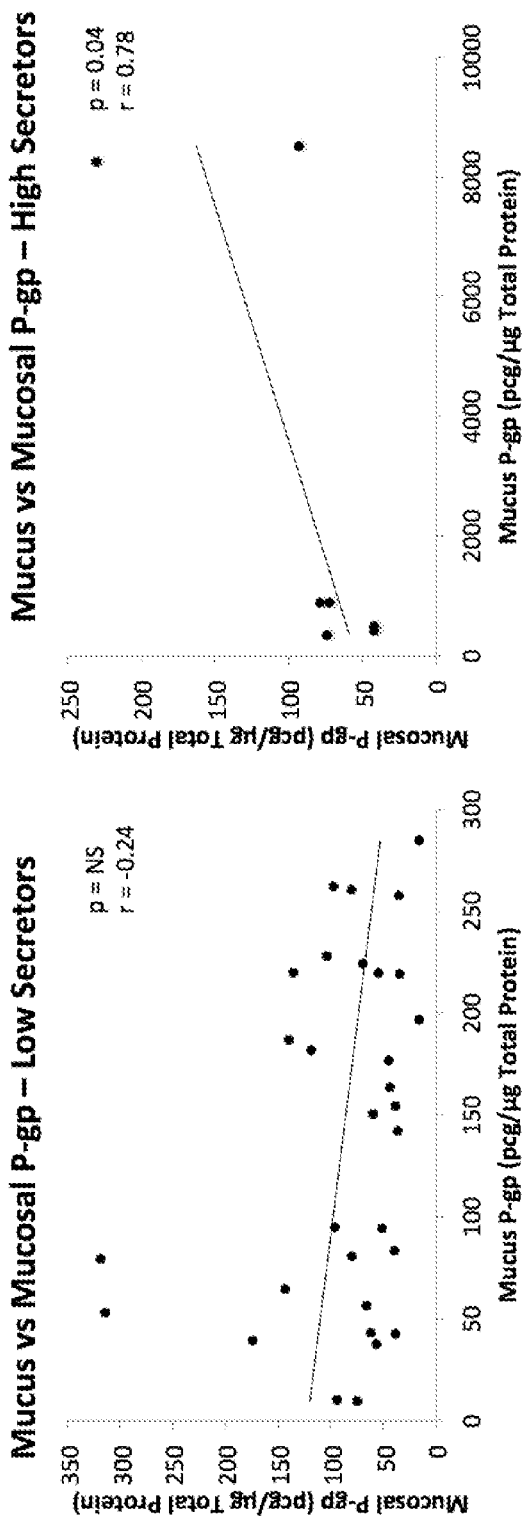
FIGS. 6A-B. Correlation between mucus and mucosal tissue levels of P-glycoprotein (P-gp) by low (A) and high (B) secretor status demonstrating a strong and significant correlation among the high secretor population.
Figures 7A, 7B:
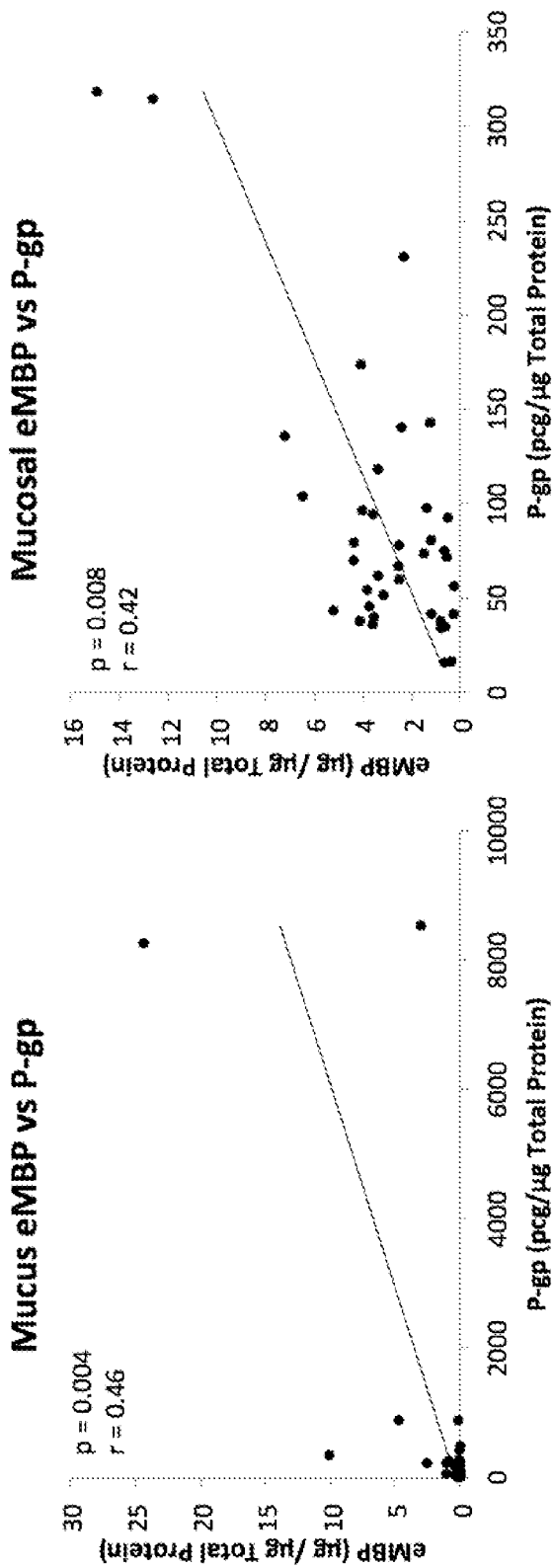
FIGS. 7A-B. Correlation between mucus (A) and mucosal tissue (B) P-gp levels and eMBP, an established biomarker of chronic rhinosinusitis, demonstrating a moderate and statistically significant correlation in both samples.

However, among the high P-gp secreting patients, a strong and statistically significant correlation was seen between secreted and mucosal P-gp concentrations (r=0.78, p=0.04) (FIGS. 6A-B). The concentration of secreted P-gp demonstrated a moderate and statistically significant correlation with that of free mucus eMBP (r=0.46, p=0.004). Similarly, tissue concentrations of P-gp demonstrated a moderate and statistically significant correlation with that of mucosal eMBP (r=0.42, p=0.008) (FIGS. 7A-B).

Figure 8:
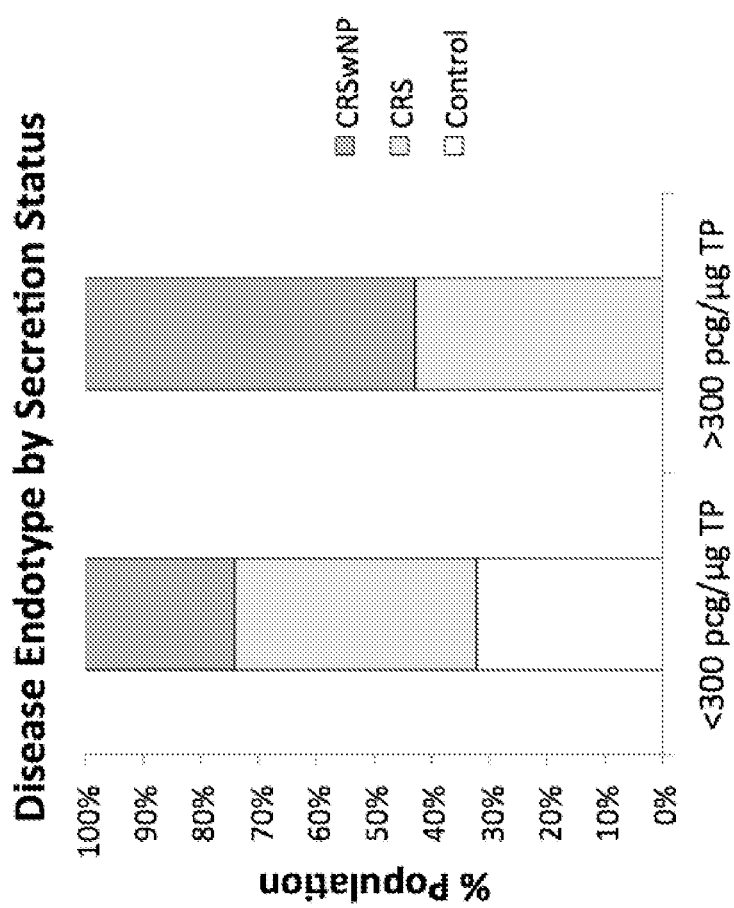
FIG. 8. Distribution of endotypes by low (<300 pcg of secreted P-gp/µg of total protein (TP)) and high (>300 pcg of secreted P-gp/µg of TP) secretor status demonstrating a shift towards a predominance of CRSwNP patients within the high P-gp secretor population.

Example 2.3 Secreted P-Glycoprotein is a Sensitive Predictor of Disease Severity The distribution of control, CRS, and CRSwNP patients among the low secretors was 32.3%, 41.9%, 25.8%; respectively. In contrast, the relative distribution among the high secretor patients shifted to a predominance of CRSwNP patients (57.1%) with the remaining 42.9% consisting only of CRS patients (FIG. 8). This high secretor group accounted for 25% of all patients in our population with any form of CRS. The cutoff of 300 pcg of secreted P-gp/µg of total protein was associated with a sensitivity of 100% and specificity of 25% for the presence of CRS.

Figures 9A, 9B:
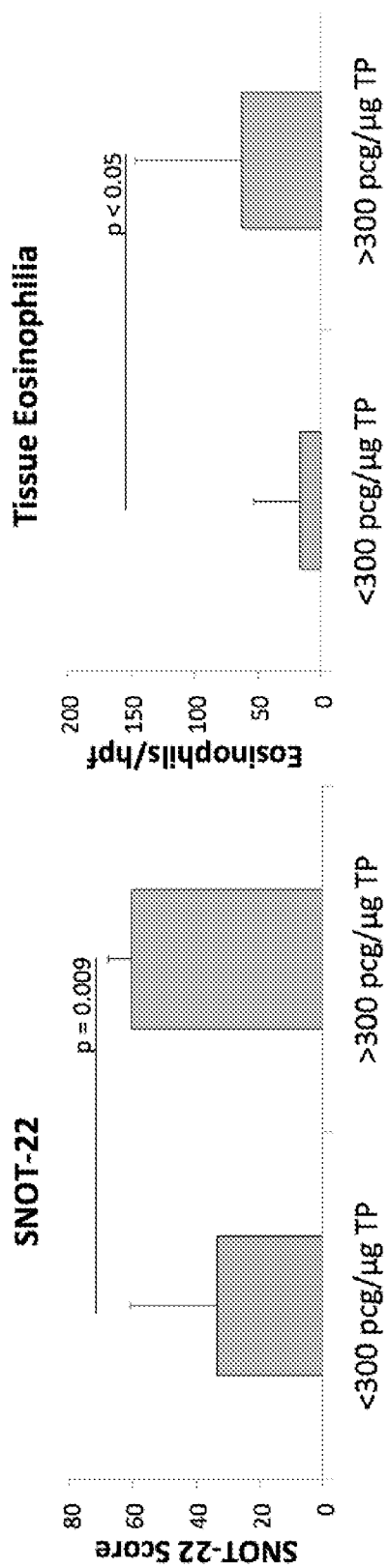
FIGS. 9A-C. Histograms of clinical disease severity indices by P-gp secretor status.
Figure 9C:
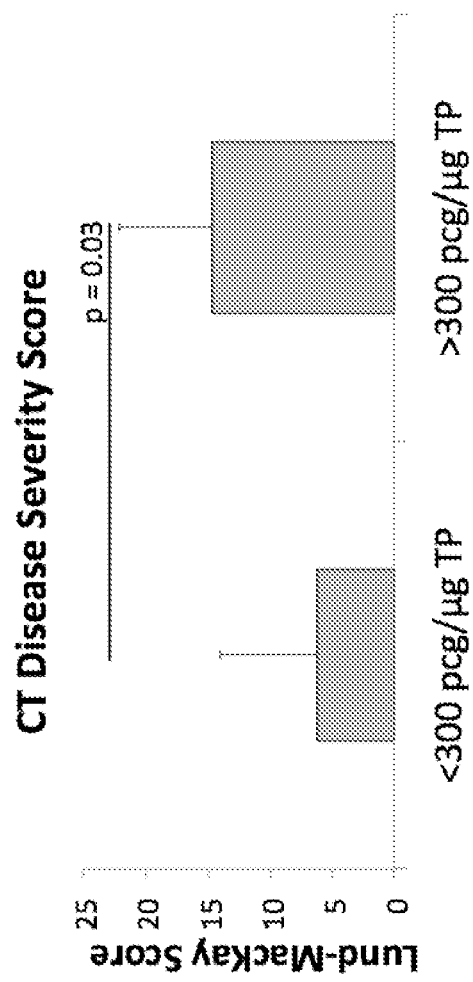

The finding of high P-gp secretion was also associated with a greater disease severity as measured by both subjective and objective endpoints. High secretors had significantly greater SNOT-22 scores (60+/−7), eosinophils/hpf (62+/−84), and Lund-Mackay scores (15+/−8) as compared to their low secretor counterparts (34+/−27, p=0.009; 16+/−36, p<0.05; and 6+/−8, p=0.03; respectively) (FIGS. 9A-C).

REFERENCES FOR EXAMPLE 2

1. Kern R C, Conley D B, Walsh W, et al. Perspectives on the etiology of chronic rhinosinusitis: an immune barrier hypothesis. *Am J Rhinol.* 22:549-559. doi:10.2500/ajr.2008.22.3228.
2. Akdis C A, Bachert C, Cingi C, et al. Endotypes and phenotypes of chronic rhinosinusitis: a PRACTALL document of the European Academy of Allergy and Clinical Immunology and the American Academy of Allergy, Asthma & Immunology. *J Allergy Clin Immunol.* 2013; 131 (6):1479-90. doi:10.1016/j.jaci.2013.02.036.
3. Pauwels B, Jonstam K, Bachert C. Emerging biologics for the treatment of chronic rhinosinusitis. *Expert Rev Clin Immunol.* 2015; 11 (3):349-61. doi:10.1586/1744666X.2015.1010517.
4. Ponikau J U, Winter L A, Kephart G M, et al. An immunologic test for chronic rhinosinusitis based on free intranasal eosinophilic major basic protein. *Int Forum Allergy Rhinol.* 2015; 5 (1):28-35. doi:10.1002/alr.21421.
5. Schmid C, Habermann W, Braun H, et al. Released intranasal eosinophilic major basic protein as a diagnostic marker for polypoid chronic rhinosinusitis. *Otolaryngol Head Neck Surg.* 2010; 143 (3):386-91. doi:10.1016/j.otohns.2010.05.017.
6. Bleier B S, Article O. Regional expression of epithelial MDR1/P-glycoprotein in chronic rhinosinusitis with and without nasal polyposis. *Int Forum Allergy Rhinol.* 2012; 2 (2):122-5. doi:10.1002/alr.21004.
7. Feldman R E, Lam A C, Sadow P M, Bleier B S. P-glycoprotein is a marker of tissue eosinophilia and radiographic inflammation in chronic rhinosinusitis without nasal polyps. *Int Forum Allergy Rhinol.* 2013; 3 (8):684-7. doi:10.1002/alr.21176.
8. Bleier B S, Nocera A L, Iqbal H, et al. P-glycoprotein promotes epithelial T helper 2-associated cytokine secretion in chronic sinusitis with nasal polyps. *Int Forum Allergy Rhinol.* 2014; 4 (6):488-94. doi:10.1002/alr.21316.
9. Bleier B S, Kocharyan A, Singleton A, Han X. Verapamil modulates interleukin-5 and interleukin-6 secretion in organotypic human sinonasal polyp explants. *Int Forum Allergy Rhinol.* 2014; 5 (1):10-13. doi:10.1002/alr.21436.
10. Chu T M, Lin T H, Kawinski E. Detection of soluble P-glycoprotein in culture media and extracellular fluids. *Biochem Biophys Res Commun.* 1994; 203 (1):506-12. doi:10.1006/bbrc.1994.2211.
11. Fokkens W J, Lund V J, Mullol J, et al. European Position Paper on Rhinosinusitis and Nasal Polyps 2012. *Rhinol Suppl.* 2012; (23):3 p preceding table of contents, 1-298. Available at: ncbi.nlm.nih.gov/pubmed/22764607. Accessed Feb. 11, 2014.
12. Hopkins C, Gillett S, Slack R, Lund V J, Browne J P. Psychometric validity of the 22-item Sinonasal Outcome Test. *Clin Otolaryngol.* 2009; 34:447-454. doi:10.1111/j.1749-4486.2009.01995.x.
13. Lund V J, Mackay IS. Staging in rhinosinusitus. *Rhinology.* 1993; 31 (4):183-4. Available at: ncbi.nlm.nih.gov/pubmed/8140385.
14. Chiampanichayakul S, Anuchapreeda S, Chruewkamlow N, Mahasongkram K, Thanaratanakorn P, Kasinrerk W. Production of monoclonal antibodies to P-glycoprotein: its application in detection of soluble and surface P-glycoprotein of leukemia patients. *Int J Hematol.* 2010; 92 (2):326-33. doi:10.1007/s12185-010-0668-8.
15. Lam A, Hoang J D, Singleton A, Han X, Bleier B S. Itraconazole and clarithromycin inhibit P-glycoprotein activity in primary human sinonasal epithelial cells. *Int Forum Allergy Rhinol.* 2015 June; 5(6):477-80.

Example 3. Inter-Epithelial Transfer of Exosomal P-Glycoprotein Promotes Inflammation in Chronic Sinusitis with Nasal Polyps Exosomes are vesicles of about 30-150 nm diameter; at least some are capable of and participate in intercellular membrane protein transfer. P-glycoprotein (P-gp) is a membrane efflux pump that promotes epithelial cytokine secretion in Chronic Rhinosinusitis with Nasal Polyps (CRSwNP). The purpose of this study was to determine 1) whether CRSwNP mucus exosomes are enriched with P-gp, 2) whether exosomal P-gp can be functionally transferred to autologous epithelial cells, and 3) whether exosome transfer enhances P-gp dependent epithelial cytokine secretion.

Methods

The following Materials and Methods were used in Example 3.

Sinonasal Mucosa and Mucus Sampling

Tissue and mucus sampling was approved by the Massachusetts Eye and Ear Infirmary Institutional Review Board. All samples were taken from patients undergoing sinonasal surgery and had not been exposed to antibiotics or steroids for at least 4 weeks prior to harvest. Inclusion criteria included patients diagnosed with CRSwNP by European Position Paper on Rhinosinusitis and Nasal Polyps (EPOS) [16] criteria and healthy patients (i.e. controls, n=10 per group) undergoing endoscopic sinus surgery for orbital or skull base pathologies. Exclusion criteria included ciliary dysfunction, autoimmune disease, cystic fibrosis, or immunodeficiency. The validated disease specific 22-item Sinonasal Outcome Test (SNOT-22)[17] was obtained on all patients. Mucus samples were taken from the middle meatus by placing a compressed polyvinyl alcohol sponge (PVA, Medtronic, Minneapolis, Minn.) against the ethmoid bulla for 5 minutes taking care not to abrade the mucosa or contaminate the sponge with blood. Mucosal samples were then taken from the ethmoid bulla.

Exosome Purification from Whole Mucus

The exosome purification procedure was adapted from the ultracentrifugation (UCF) procedure described by Théry et al[18]. This technique was compared with a commercially available precipitation method (ExoQuick™, System Biosciences, Palo Alto, Calif.) and provided greater purity with higher protein and exosome yield in agreement with van Deun et al[19](FIGS. 10A-B). Mucus samples were extracted from the PVA sponge by centrifugation (1500 g at 4° C. for 30 minutes). The mucus was then diluted in 150 μL of 1× phosphate buffered saline (PBS, Life Technologies, Carlsbad, Calif.) with Protease Inhibitor Cocktail (1:100, Sigma, St. Louis, Mo.). Cellular debris was pelleted by centrifugation at 45 min at 12,000×g at 4° C. The supernatant was then suspended in 4.5 mL of PBS in polypropylene tubes (Thinwall, 5.0 mL, 13×51 mm, Beckman Coulter, Indianapolis, Ind.) and ultracentrifuged for 2 hours at 110,000×g, at 4° C. The supernatant was collected and the pellet was resuspended in 4.5 mL 1×PBS. The suspension was filtered through a 0.22-μm filter (Fisher Scientific, Pittsburgh, Pa.) and collected in a fresh ultracentrifuge tube. The filtered suspension was then centrifuged for 70 min at 110,000×g at 4° C. The supernatant was collected and the pellet was resuspended in 200 μl PBS with protease inhibitor. Prior to cell culture dosing the exosome concentration of each pellet was determined using a commercially available enzyme linked immunosorbent assay (ELISA) for the established exosome markers CD63 and CD9 (ExoELISA, System Biosciences, Palo Alto, Calif.) as previously described [20].

Transmission Electron Microscopy of Mucus Derived Exosomes

The exosome transmission electron microscopy (TEM) procedure was adapted from Théry et al[18]. Isolated exosomes were fixed for 1 hour at room temperature in 2% paraformaldehyde in 0.1M sodium phosphate buffer (Electron Microscopy Sciences, Hatfield, Pa.). 5 μL of the exosomes were absorbed on to Formvar-carbon coated electron microscopy grids (Electron Microscopy Sciences) for 20 minutes. After absorption, the grids were rinsed in PBS 3 times and then transferred to PBS/50 mM glycine (Sigma Aldrich, St. Louis Mo.) for 4 washes. The grids were blocked in 5% Bovine Serum Albumin (BSA, Fisher Scientific) in 1× phosphate buffered saline (buffer) for 10 minutes at room temperature. The grids were incubated at 4° C. overnight in the primary antibody (1:25, Purified Mouse Anti-Human CD63 Clone H5C6, BD Biosciences) diluted in 1% BSA buffer. The grids were then rinsed in 0.1% BSA buffer and then 0.5% BSA buffer 6 times each. Then the secondary Protein-G antibody (1:20 in 1% BSA buffer, EM Grade, 10 nm, Electron Microscopy Services, Hatfield, Pa.) in 5% BSA buffer was applied for 1 hour at room temperature and rinsed 8 times with 1×PBS. The grids were incubated in 1% glutaraldehyde in 0.1M sodium phosphate buffer (Electron Microscopy Services) for 5 minutes. After rinsing 8 times in deionized water, the grids were contrasted in uranyl-oxalate solution, pH 7 (UA, Electron Microscopy Services) for 5 minutes. The grids were blotted on filter paper and air dried prior to imaging. The exosomes were observed using a FEI Tecnai G2 Spirit transmission electron microscope (FEI, Hillsboro, Oreg.) at an accelerating voltage of 100 kV interfaced with an AMT XR41 digital CCD camera (Advanced Microscopy Techniques, Woburn, Mass.) for digital TIFF file image acquisition. Rabbit IgG (Vector Laboratories, Burlingame, Calif.) and CD63 lysate (Novus Biologicals CD63 Overexpression Lysate (Native), Fisher Scientific) were used as negative and positive controls, respectively.

In Vivo Quantification of Mucus Derived Exosomal P-gp Concentration

Mucus was collected from both control and CRSwNP patients for in vivo characterization of exosomal P-gp concentration (see Table 2). The mucus was collected using a PVA sponge followed by exosome purification as described above. The purified exosome fraction was subjected to P-gp, CD63, and CD9 (Systems Bioscience) ELISAs to determine the relative P-gp concentration within the purified exosomal fraction. All values were normalized to the total protein concentration within the same sample using a Micro BCA Protein Assay Kit (Pierce, Rockford, Ill.).

TABLE 2

Patient demographics

|  | Control (n = 10) | CRSwNP (n = 10) |
|---|---|---|
| Age-Median Years (Interquartile Range) | 57 (24.8-70.5) | 53.5 (40.3-60.8) |
| Sex |  |  |
| Male | 2 (20%) | 6 (60%) |
| Female | 8 (80%) | 4 (40%) |
| Race |  |  |
| African-American | 1 (10%) | 0 (0%) |
| Asian | 1 (10%) | 3 (30%) |
| Caucasian | 7 (70%) | 5 (50%) |
| Hispanic | 1 (10%) | 2 (20%) |
| Asthma | 2 (20%) | 5 (50%) |
| Allergy | 4 (40%) | 3 (30%) |
| Aspirin Allergy | 1 (10%) | 1 (10%) |

Western Blot

Western blot was used to additionally verify the presence of P-gp within the mucus derived exosome fraction. After exosome isolation as described above, total protein was determined using the Micro BCA assay Kit. 10 μg of total protein and Laemmli loading buffer (2× Laemmli sample buffer, Bio-Rad, Hercules, Calif., with β-mercaptoethanol, Sigma, St. Louis, Mo.) were denatured at 95° C. for 3 minutes and separated on precast NOVEX® 4-20% Tris-Glycine Mini Protein Gels (1.0 mm, 9 wells, Life Technologies) (polyacrylamide gels based on traditional Laemmli protein electrophoresis, which allows the use of Laemmli sample and running buffers). The protein was transferred onto a polyvinylidene fluoride membrane by IBLOT® Dry Blotting System (Invitrogen, Carlsbad, Calif.) (Western blot transfer system). The membrane was blocked with 5% skim milk in Tris buffered saline and Tween-20 (TBST, Sigma Aldrich) for 1 hour at room temperature. The primary antibody (Monoclonal Anti-P-glycoprotein Clone F4, 1:1000, in 5% milk in TBST) was added and incubated at 4° C. overnight. After 3 washes of 15 minutes each with TBST, the secondary antibody (Anti-Mouse IgG (Fab specific)—Peroxidase antibody produced in goat in 5% milk in TBST, Sigma) was incubated for 1 hour at room temperature. The membrane was washed again 3 times of 15 minutes each with TBST and SuperSignal™ West Pico Chemiluminescent Substrate (Life Technologies) was applied for 5 minutes before visualization with ChemiDoc MP (Bio-Rad). Recombinant P-gp (USCN Life Sciences Inc., Wuhan, P.R. China)

was used as a control and a monoclonal anti-GAPDH antibody produced in mouse (Sigma Aldrich) was used as a loading control Primary Human Sinonasal Epithelial Cell Culture Human sinonasal epithelial cell cultures (HSNECCs) were grown as previously described [21]. Briefly, mucosal biopsy samples were washed and digested in Pronase for 90 minutes at 37° C. Cell suspensions were separated from particulate matter by centrifugation and resuspended in bronchial epithelial growth media (BEGM, Lonza, Basel, Switzerland). Cells were plated for 2 hours on standard tissue culture plates to remove contaminating fibroblasts. Cells were then expanded for 3-5 days on human collagen type IV-coated (Collagen from human placenta, Bornstein and Traub Type IV, Sigma Aldrich, St. Louis, Mo.) 75 cm$^2$ dishes (Corning Life Sciences, Corning, N.Y.). Once confluent, the HSNECCs were trypsinized and re-seeded evenly in human collagen type IV-coated black walled 96-well (Corning 96-well Plates) tissue culture plates in BEGM and grown to 80% confluence prior to analysis. All in vitro experiments were associated with less than 20% cytotoxicity as determined by the ReadyProbes Cell Viability Imaging Kit (Blue/Green, Life Technologies, Carlsbad, Calif.) (see FIGS. 11A-B).

Determination of In Vitro Internalization of Mucus Derived Exosomes by HSNECCs

Autologous isolated exosomes were dyed using 10× commercially available Exo-Red™ Acridine Orange (AO) and Exo-Green™ carboxyfluorescein succinimidyl diacetate ester (CFSE) fluorescent labels (Systems Bioscience), according to the manufacturer's instructions, to characterize RNA and protein (respectively) internalization into HSNECCs derived from the same patient. After labeling, 25 µL of the purified autologous exosomes (1.25×10$^9$ exosomes/mL) were added to the HSNECCs in a black walled 96-well plate. The wells were imaged every 10 minutes for 30 minutes using a Leica DM IL LED fluorescent microscope (Leica, Buffalo Grove, Ill.) and a 20× objective. The same field of view was used for all time points.

Quantification of Exosome Mediated Transfer of Functional P-gp

A Calcein Acetoxymethylester (AM) assay[22] was performed on the HSNEC cultures following dosing with autologous purified mucus derived exosomes to quantify the relative acquisition of functional P-gp activity. HSNECCs were exposed to BEGM containing exosomes (1.25×10$^9$ exosomes/mL) or exosomes along with 0.625 µM of the 3rd generation P-gp inhibitor Zosuquidar 3HCl (Medkoo, Chapel Hill, N.C.) [23]. Pre-warmed Calcein AM (Life Technologies) was added to each well for a final concentration of 2.5 µM as previously described [22]. After 15 minutes, each well was washed 3× with cold phosphate buffered saline and the wells were imaged in triplicate. Fluorescence was quantified using the corrected total cell fluorescence method as previously described by McCloy et al. [24]. A reduction in calcein fluorescence corresponds to a gain in P-gp function while an increase in fluorescence corresponds to successful inhibition [22].

Analysis of Exosome Derived P-gp Regulation of Epithelial Cytokine Secretion

Confluent HSNECCs were exposed to 23 hours of vehicle control (BEGM), 0.625 µM Zosuquidar HCl, in the presence or absence of 50 µL purified autologous exosomes (5.3×10$^{10}$ exosomes/mL) applied for 1 hour. Control wells were those exposed to vehicle control alone. Following exposure, the media was collected from each well. Cytokine concentrations for TSLP (Thymic Stromal Derived Lymphopoietin), Interleukin (IL)-6, and IL-8 were determined by ELISA according to the manufactures guidelines (eBioscience, San Diego, Calif.). All secreted cytokine concentrations were normalized to total protein concentrations using the Micro BCA Protein Assay Kit (Pierce, Rockford, Ill.).

Statistics

Statistical analysis was performed using R v3.3.0. The Shapiro-Wilk test was used for assessing normality. For the non-parametric data, the Kruskal-Wallis test was used to examine statistical differences between multiple groups and the Mann-Whitney rank sum test was used to examine statistical differences between two independent groups. Correlations were tested using the 2-tailed Spearman's rank-order correlation. Values falling outside 1.5 times the interquartile range of their respective data set were considered outliers and indiscriminately excluded from analysis. Results were considered significant when a P value of <0.05 was obtained. All in vitro studies were performed in technical duplicates.

Figure 12:
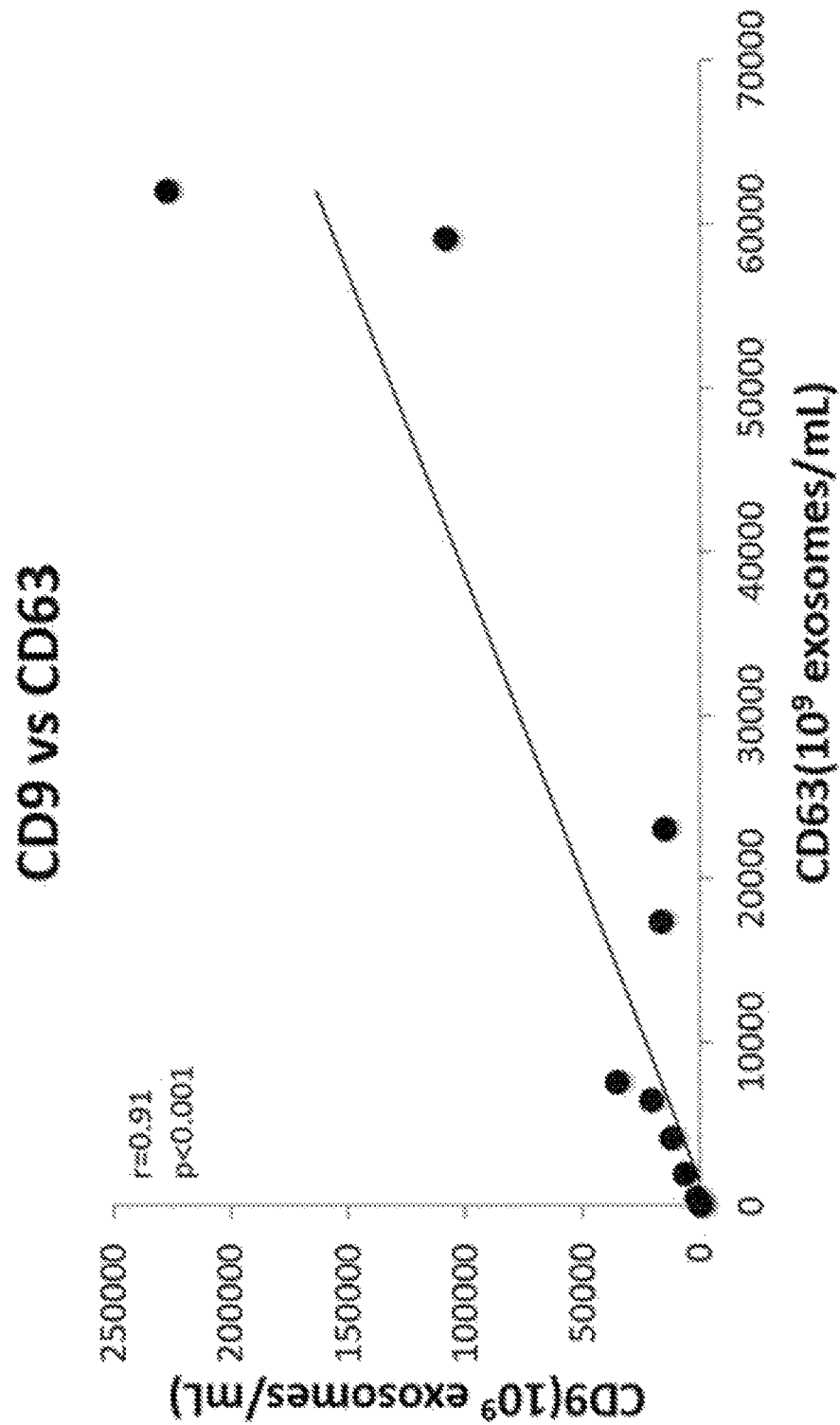
FIG. 12. Correlation curve demonstrating a strong and significant correlation between exosome tetraspanin markers CD63 and CD9 within purified mucus exosome fractions.

Example 3.1 Exosomes are Present in Sinonasal Mucus and are Enriched with P-gp Among Patients with CRSwNP The first series of experiments were designed to quantify the presence of exosomes within nasal mucus and to characterize the relative abundance of exosomal P-gp by patient group. CD63 is one of the most commonly utilized exosome markers and correlated strongly with CD9, another exosome associated tetraspanin (FIG. 12). CD63 was therefore used as the primary exosome marker throughout the study[10]. Among both the control and CRSwNP purified exosome fractions, we found structures corresponding to the expected 30-150 nm size and spheroid morphology of exosomes using TEM [12]. Subsequent immunogold labeling then confirmed the presence of both CD63 and P-gp epitopes within the exosome superstructure (FIG. 13A). Having confirmed the presence of P-gp containing exosomes in nasal mucus by TEM, we next sought to determine whether there was a difference in secreted exosome volume or P-gp composition between the mucus of control and CRSwNP patients (n=10 per group, see Table 2) by ELISA. We found no significant difference between median total exosome concentration between the CRSwNP (1831.0, IQR 519.3 to 3073.4 exosomes/pcg total protein) and control group (1405.3, IQR 934.4 to 2403.7; p=0.84) (FIG. 13B). However, among the CRSwNP patients, the median concentration of P-gp per exosome was significantly greater (198.5, IQR 123.6 to 270.5 pcg P-gp/10$^9$ exosomes) than that of the control patients (74.4, IQR 41.3 to 95.0, p=0.002) (FIG. 13C). Finally, in order to confirm both the presence and relative abundance of exosomal P-gp in the TEM and ELISA studies, we utilized western blot which again demonstrated P-gp within the purified CRSwNP exosome fractions as well as a faint signal within the control samples (FIG. 13D).

Figure 14A:
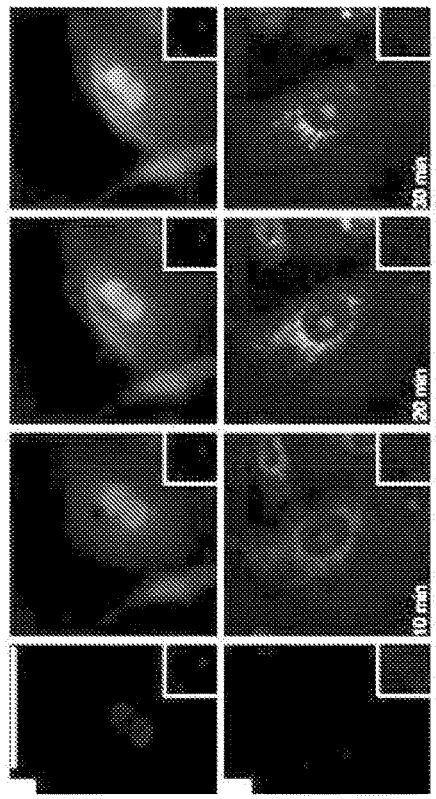
FIGS. 14A-B. Epithelial cell internalization of autologous exosomes: (A) Time lapse fluorescent images of exosomal uptake by autologous epithelial cells (bar 50 µm, blue-nuclear stain, green-CFSE exosome protein stain, orange-AO exosome RNA stain). Within 10 min of exposure, the exosomes can be clearly seen within the membrane and cytoplasm of the cell. Over the subsequent 20 minutes the protein signal spreads throughout the cell while the exosomal RNA concentrates around the nucleus (insets represent time matched unstained exosome negative controls). (B) Histogram (median, error bars represent IQR) of Calcein AM fluorescence demonstrating a differential gain of P-gp function following exosome exposure in CRSwNP patients relative to control which is abrogated by P-gp specific inhibition with Zosuquidar.
Figure 14B:
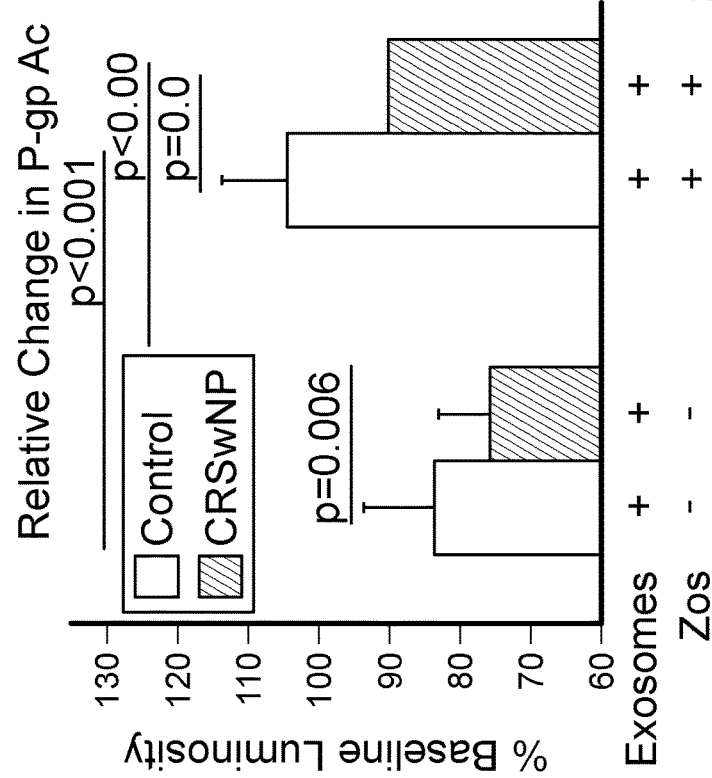

Example 3.2 Autologous Exosomes are Capable of Transferring Functional P-gp to Cultured Sinonasal Epithelial Cells After establishing the presence of P-gp within mucus derived exosomes from both control and CRSwNP patients, we next sought to determine whether these exosomes could be transferred from the mucus to naïve cultured epithelial cells. After exposing the cells to purified autologous exosomes, we demonstrated a rapid and progressive uptake of labeled exosomal protein and RNA as early as 10 minutes (FIG. 14A). This time scale is consistent with the possibility of inter-epithelial transfer of exosomes as a consequence of physiologic mucociliary clearance transport. We next studied whether uptake of these exosomes was associated with the transfer of functional P-gp. Utilizing an established calcein AM P-gp activity assay [22], we found that exosome exposure resulted in a significant reduction in calcein fluorescence indicating a gain of P-gp function. The median reduction was significantly greater in the CRSwNP group (75.6% Baseline, Interquartile range (IQR) 74.1% to 81.5%) relative to control (83.8% Baseline, IQR 77.3% to 87.3%; p=0.007) which is consistent with the relative enrichment of exosomal P-gp evident in the ELISA and western blot findings. Furthermore, this gain in function was abrogated by the addition of Zosuquidar, a highly potent and specific inhibitor of P-gp [22] (FIG. 14B), providing confirmatory evidence for the exosomal mediated transfer of functional P-gp.

Figure 15B:
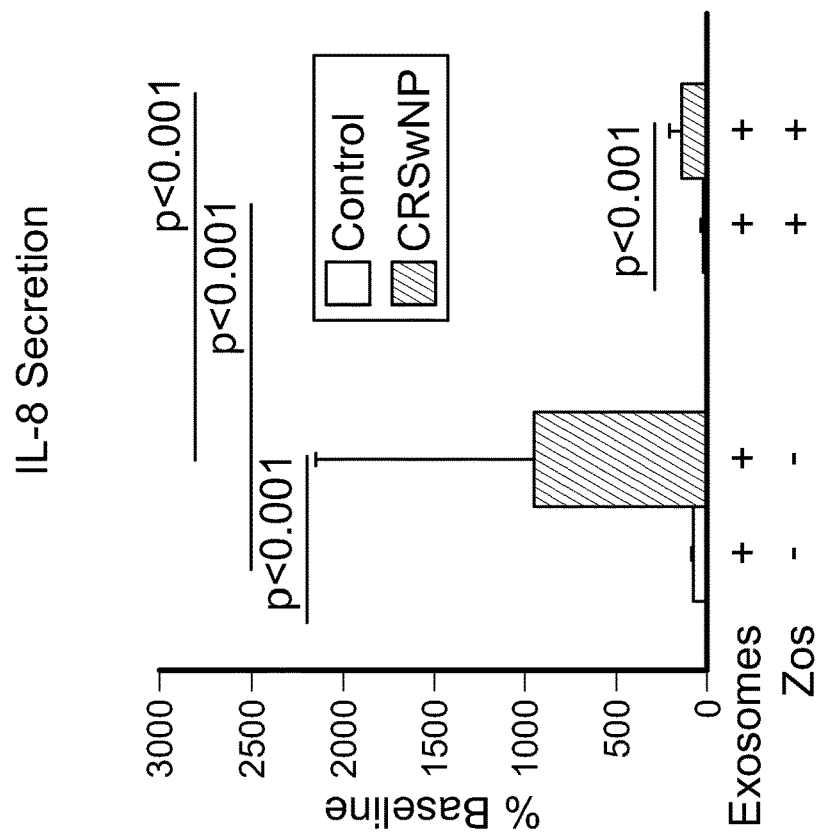
FIGS. 15A-B. (A) Histogram (median, error bars represent IQR) of IL-6 secretion following exosome exposure demonstrating a differential increase in secretion among CRSwNP patients relative to control which is abrogated by P-gp specific inhibition with Zosuquidar; (B) Histogram (median, error bars represent IQR) of IL-8 secretion following exosome exposure demonstrating a differential increase in secretion among CRSwNP patients relative to control which is abrogated by P-gp specific inhibition with Zosuquidar.
Figure 15A:
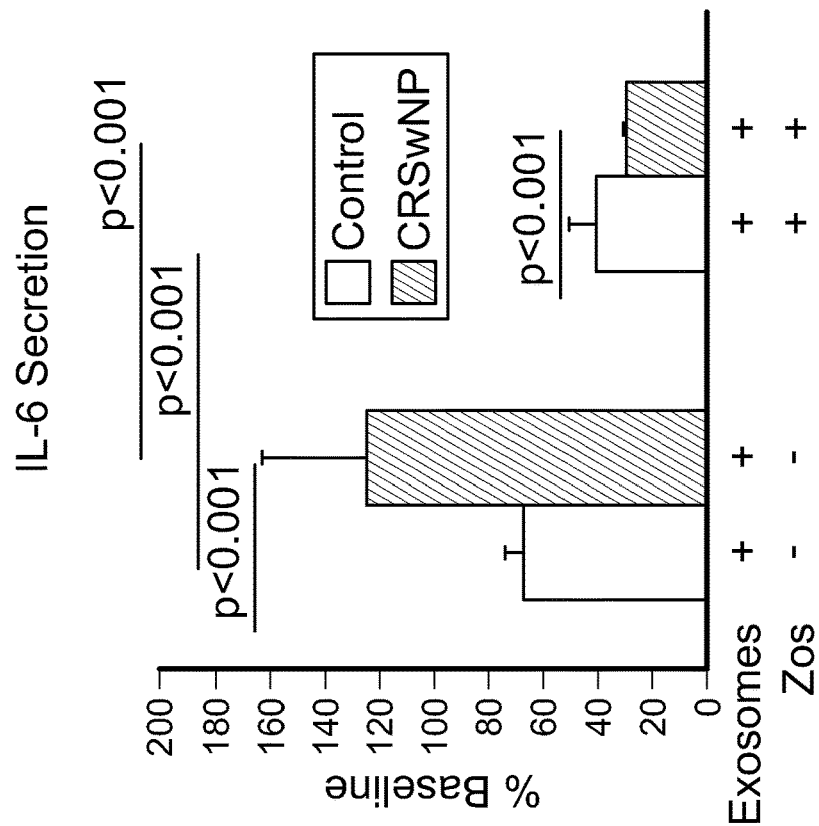

Example 3.3 Exosome Derived P-gp is Capable of Modulating Epithelial Derived Cytokine Secretion Previous studies from our group have demonstrated that P-gp is capable of modulating epithelial cytokine secretion in a concentration dependent manner [5]. Following confirmation of exosome derived functional P-gp transfer, we next examined whether exosome exposure was capable of conferring enhanced P-gp dependent cytokine secretion to the recipient cells. Exosome exposure significantly promoted P-gp dependent secretion of IL-6 (124.3% Baseline; IQR 105.2-143.4%) and IL-8 (942.6%; 344.2-1541.1%) in CRSwNP cultures relative to control (67%; 63.7-70.3%; p<0.001 and 72.7%; 70.2-75.2%; p<0.001; respectively). Abrogation of this secretion by the subsequent addition of Zosuquidar confirmed that the effect was mediated by P-gp (FIGS. 15A-B). TSLP secretion remained below the ELISA detection threshold (8 pcg/mL) among all conditions in both groups.

Figure 16:
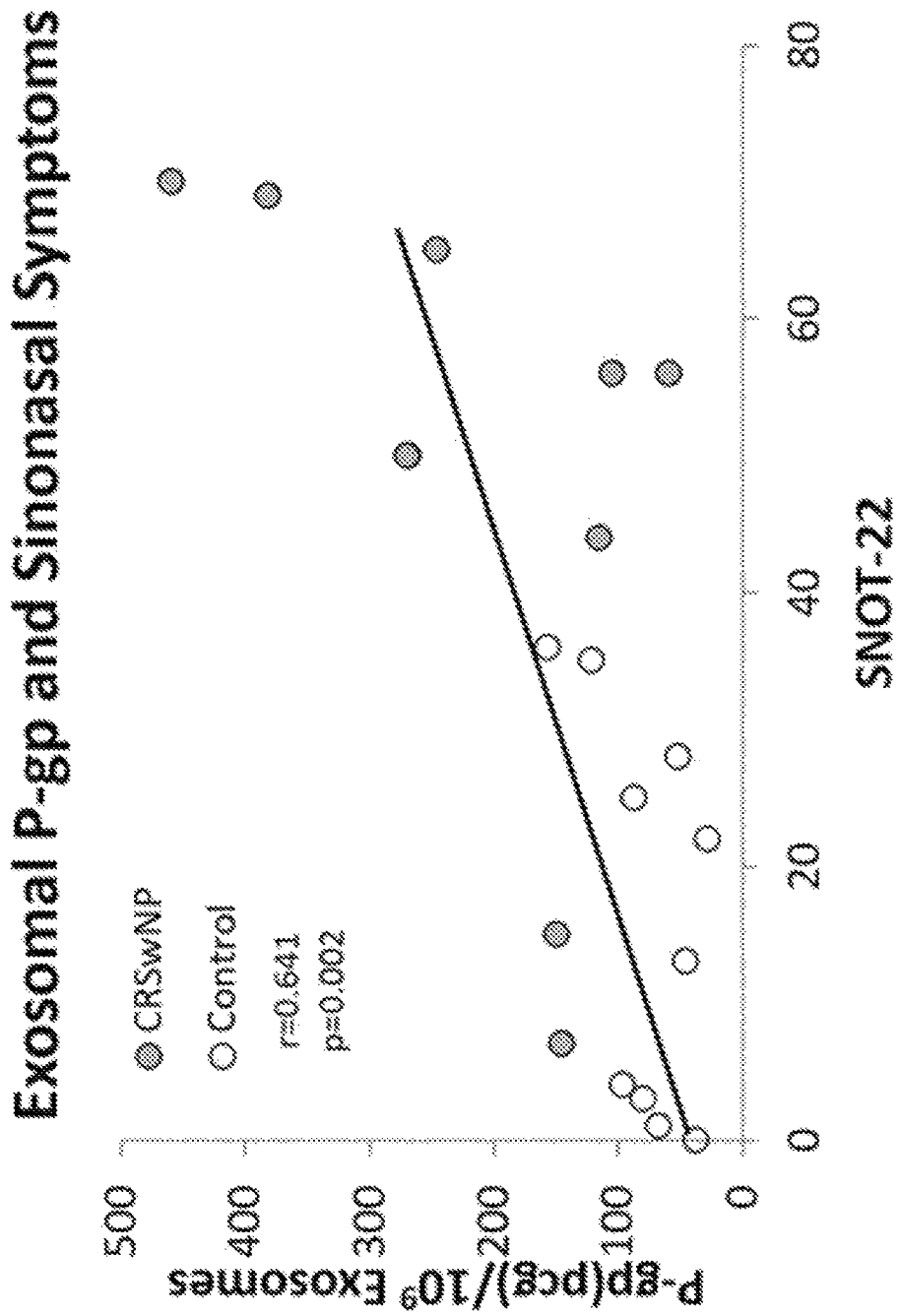
FIG. 16. Correlation curve demonstrating a significant correlation between subjective nasal symptoms scores (SNOT-22) and exosomal P-gp concentration among all patients studied.

Example 3.4 Mucus Derived Exosomal P-gp Levels Correlate with Sinonasal Symptoms The P-gp/exosome concentration among all patients was moderately and significantly correlated with their subjective nasal symptoms scores as measured by SNOT-22 (r=0.641, p=0.002) (FIG. 16).

Taken as a whole, the data presented in Example 3 points to a novel mechanism for the maintenance of inflammation in CRSwNP, which shows that exosomes within the nasal mucus of patients with CRSwNP are enriched with P-gp, and can be functionally transferred to adjacent epithelial cells through mucociliary flow. This P-gp can, in turn, promote the secretion of epithelial derived cytokines thereby maintaining the chronic inflammatory state characteristic of the disease.

REFERENCES FOR EXAMPLE 3

1. Fernandez C, Buyse M, German-Fattal M, Gimenez F. Influence of the pro-inflammatory cytokines on P-glycoprotein expression and functionality. *J. Pharm. Pharm. Sci.* 2004; 7:359-371.
2. Cleves A E, Kelly R B. Rehearsing the ABCs. Protein translocation. *Curr. Biol.* 1996; 6:276-8.
3. Drach J, Gsur A, Hamilton G, et al. Involvement of P-glycoprotein in the transmembrane transport of interleukin-2 (IL-2), IL-4, and interferon-gamma in normal human T lymphocytes. *Blood* 1996; 88:1747-1754.
4. Bleier B S, Nocera A L, Iqbal H, Hoang J D, Feldman R E, Han X. P-glycoprotein functions as an immunomodulator in healthy human primary nasal epithelial cells. *Int. Forum Allergy Rhinol.* 2013; 3:433-8.
5. Bleier B S, Kocharyan A, Singleton A, Han X. Verapamil modulates interleukin-5 and interleukin-6 secretion in organotypic human sinonasal polyp explants. *Int. Forum Allergy Rhinol.* 2014; 5:10-13.
6. Bleier B S, Singleton A, Nocera A L, Kocharyan A, Petkova V, Han X. P-glycoprotein regulates *Staphylococcus aureus* enterotoxin B-stimulated interleukin-5 and thymic stromal lymphopoietin secretion in organotypic mucosal explants. *Int Forum Allergy Rhinol.* 2016 February; 6(2):169-77. Epub 2015 Dec. 1.
7. Bleier B S, Article O. Regional expression of epithelial MDR1/P-glycoprotein in chronic rhinosinusitis with and without nasal polyposis. *Int. Forum Allergy Rhinol.* 2012; 2:122-5.
8. Feldman R E, Lam A C, Sadow P M, Bleier B S. P-glycoprotein is a marker of tissue eosinophilia and radiographic inflammation in chronic rhinosinusitis without nasal polyps. *Int. Forum Allergy Rhinol.* 2013; 3:684-7.
9. Nocera A L, Muerer A T, Singleton A, et al. Intact Soluble P-glycoprotein is Secreted by Sinonasal Epithelial Cells. *Am. J. Rhinol. Allergy* 2016; 4:246-9
10. Lee T H, D'Asti E, Magnus N, Al-Nedawi K, Meehan B, Rak J. Microvesicles as mediators of intercellular communication in cancer—the emerging science of cellular 'debris'. *Semin. Immunopathol.* 2011; 1-13.
11. Lee Y, El Andaloussi S, Wood M J a. Exosomes and microvesicles: Extracellular vesicles for genetic information transfer and gene therapy. *Hum. Mol. Genet.* 2012; 21:125-134.
12. Schorey J S, Cheng Y, Singh P P, Smith V L. Exosomes and other extracellular vesicles in host-pathogen interactions. *EMBO Rep.* 2015; 16:24-43.
13. Mack M, Kleinschmidt a, Bral H, et al. Transfer of the chemokine receptor CCR5 between cells by membrane-derived microparticles: a mechanism for cellular human immunodeficiency virus 1 infection. *Nat. Med.* 2000; 6:769-775.
14. Lv M M, Zhu X Y, Chen W X, et al. Exosomes mediate drug resistance transfer in MCF-7 breast cancer cells and a probable mechanism is delivery of P-glycoprotein. *Tumor Biol.* 2014; 10773-10779.
15. Bebawy M, Combes V, Lee E, et al. Membrane microparticles mediate transfer of P-glycoprotein to drug sensitive cancer cells. *Leuk. Off. J. Leuk. Soc. Am. Leuk. Res. Fund,* U. K 2009; 23:1643-1649.
16. Fokkens W J, Lund V J, Mullol J, et al. European Position Paper on Rhinosinusitis and Nasal Polyps 2012. *Rhinol. Suppl.* 2012; 3 p preceding table of contents, 1-298.
17. Hopkins C, Gillett S, Slack R, Lund V J, Browne J P. Psychometric validity of the 22-item Sinonasal Outcome Test. *Clin. Otolaryngol.* 2009; 34:447-454.
18. Théry C, Amigorena S, Raposo G, Clayton A. Isolation and characterization of exosomes from cell culture supernatants and biological fluids. *Curr. Protoc. Cell Biol.* 2006; Chapter 3:Unit 3.22.
19. Van Deun J, Mestdagh P, Sormunen R, et al. The impact of disparate isolation methods for extracellular vesicles on downstream RNA profiling. *J. Extracell. vesicles* 2014; 1:1-14.

20. Mallegol J, Van Niel G, Lebreton C, et al. T84-Intestinal Epithelial Exosomes Bear MHC Class II/Peptide Complexes Potentiating Antigen Presentation by Dendritic Cells. *Gastroenterology* 2007; 132:1866-1876.
21. Bleier B S, Mulligan R M, Schlosser R J. Primary human sinonasal epithelial cell culture model for topical drug delivery in patients with chronic rhinosinusitis with nasal polyposis. *J. Pharm. Pharmacol.* 2012; 64:449-56.
22. Bleier B S, Nocera A L, Iqbal H, et al. P-glycoprotein promotes epithelial T helper 2-associated cytokine secretion in chronic sinusitis with nasal polyps. *Int. Forum Allergy Rhinol.* 2014; 4:488-94.
23. Lam A, Hoang J D, Singleton A, Han X, Bleier B S. Itraconazole and clarithromycin inhibit P-glycoprotein activity in primary human sinonasal epithelial cells. *Int. Forum Allergy Rhinol.* 2015; June; 5(6):477-80.
24. McCloy R a., Rogers S, Caldon C E, Lorca T, Castro A, Burgess A. Partial inhibition of Cdk1 in G2 phase overrides the SAC and decouples mitotic events. *Cell Cycle* 2014; 13:1400-1412.
25. Wu G, Yang G, Zhang R, et al. Altered microRNA Expression Profiles of Extracellular Vesicles in Nasal Mucus From Patients With Allergic Rhinitis. *Allergy Asthma Immunol Res.* 2015; 7:449-457.
26. Gudis D, Zhao K, Cohen N A. Acquired cilia dysfunction in chronic rhinosinusitis. *Am. J. Rhinol. Allergy* 26:1-6.
27. Levchenko A, Mehta B M, Niu X, et al. Intercellular transfer of P-glycoprotein mediates acquired multidrug resistance in tumor cells. *Proc. Natl. Acad. Sci. U.S.A.* 2005; 102:1933-1938.
28. Pasquier J, Galas L, Boulange-Lecomte C, et al. Different modalities of intercellular membrane exchanges mediate cell-to-cell P-glycoprotein transfers in MCF-7 breast cancer cells. *J. Biol. Chem.* 2012; 287:7374-7387.
29. Bebawy M, Combes V, Lee E, et al. Tumor cell-derived exosomes: A message in a bottle. i 2015; 5:1-13.
30. Tomassen P, Vandeplas G, Van Zele T, et al. Inflammatory endotypes of chronic rhinosinusitis based on cluster analysis of biomarkers. *J. Allergy Clin. Immunol.* 2016

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of diagnosing and treating Chronic Rhinosinusitis (CRS) in a human subject, the method comprising:
providing a sample comprising nasal secretions comprising secreted p-glycoprotein (P-gp) from the subject;
detecting the level of secreted p-glycoprotein (P-gp) in the sample;
comparing the level of P-gp in the sample to a reference level of P-gp,
wherein the level of P-gp in the sample above the reference level indicates that the subject has CRS;
identifying the subject as having CRS; and
administering a therapeutically effective amount of a P-gp inhibitor to the subject.

2. The method of claim 1, wherein detecting the level of secreted p-glycoprotein (P-gp) in the sample comprises contacting the sample with an antibody or antigen-binding fragment thereof that binds specifically to P-gp.

3. The method of claim 1, wherein the sample comprises nasal mucus derived exosomes, and detecting a level of secreted p-glycoprotein (P-gp) in the sample comprises detecting a level of P-gp in the nasal mucus derived exosomes.

4. The method of claim 3, comprising:
isolating nasal mucus derived exosomes from the subject; and
detecting the level of P-gp in the nasal mucus derived exosomes.

5. A method of selecting a human subject for treatment with a P-glycoprotein inhibitor, and treating the subject, the method comprising:
providing a sample comprising nasal secretions from the subject;
detecting a level of secreted p-glycoprotein (P-gp) in the sample; and
comparing the level of P-gp in the sample to a reference level of P-gp;
wherein the level of P-gp in the sample above the reference level indicates that the subject is likely to benefit from treatment with a P-glycoprotein inhibitor; and
selecting the subject for treatment with a P-glycoprotein inhibitor; and
administering to the subject an effective amount of a P-glycoprotein inhibitor.

6. The method of claim 5, wherein the sample comprises nasal mucus derived exosomes, and detecting the level of secreted p-glycoprotein (P-gp) in the sample comprises detecting the level of P-gp in the nasal mucus derived exosomes.

7. The method of claim 6, comprising:
isolating nasal mucus derived exosomes from the subject; and
detecting the level of P-glycoprotein (P-gp) in the nasal mucus derived exosomes.

8. The method of claim 1, wherein the P-glycoprotein inhibitor is verapamil2-(methylamino)-3-oxo-6-octenoic acid]-7-L-valine-cyclosporin A (PSC 833), R-verapamil4-(2-(6,7-dimethoxy-3,4-dihydroisoquinolin-2 (1H)-yl)ethyl) phenyl)-5-methoxy-9-oxo-9,10-dihydroacridine-4-carboxamide hydrochloride (GF120918), 1,7-di (pyridin-3-yl) heptan-4-yl (2S)-1-[oxo (3,4,5-trimethoxyphenyl)acetyl] piperidine-2-carboxylate (VX-7101-(4-(2-hydroxy-3-(quinolin-5-yloxy) propyl)piperazin-1-yl)-2,2-diphenylethanone (MS-2093-(quinolin-5-yloxy) propan-2-ol,trihydrochloride (LY3359794-(propan-2-ylamino) phenyl]-1H-imidazol-5-yl]-N-propan-2-ylaniline (OC14409311-(1-(4-(quinolin-2-ylmethoxy) phenethyl)piperidin-4-ylidene)-6,11-dihydro-5H-benzo[d]imidazo[1,2-a]azepine-3-carboxylate (R1019333-((Z) 4-(2-(6,7-dimethoxy-3,4-dihydroisoquinolin-2 (1H) henyl)benzamide (XR9051), or N-(4-(2-(6,7-dimethoxy-3,4-dihydroisoquinolin-2 (1H)-yl)ethyl)phenyl)benzamide (XR9051), or N-[2-[[4-[2-(6,7-Dimethoxy-3,4-dihydro-1H-isoquinolin-2-yl)ethyl]phenyl]carbamoyl]-4,5-dimethoxyphenyl]quinoline-3-carboxamide (XR9576).

9. The method of claim 1, wherein the P-glycoprotein inhibitor is administered systemically or locally to the subject's nasal passage and sinuses.

10. The method of claim 9, wherein the P-glycoprotein inhibitor is delivered to the subject's nasal passage and sinuses by an inhalation device, by flushing, or by spraying.

11. The method of claim 9, wherein the P-glycoprotein inhibitor is administered to the subject as a P-glycoprotein inhibitor eluting implant surgically placed in the subject's nasal passage or sinuses.

12. The method of claim 11, wherein the P-glycoprotein inhibitor eluting implant is bio-absorbable.

13. The method of claim 1, wherein the presence of rhinosinusitis was confirmed by endoscopy or computed tomography.

14. The method of claim 1, wherein the P-gp inhibitor is administered in combination with one or both of a corticosteroid and an antibiotic.

15. The method of claim 14, wherein the corticosteroid is selected from dexamethasone, prednisone, prednisolone, triamcinolone, cortisol, budesonide, mometasone, fluticasone, flunisolide, and betamethasone.

16. The method of claim 14, wherein the antibiotic is selected from erythromycin, doxycycline, tetracycline, penicillin, beta-lactam, macrolide, fluoroquinolone, cephalosporin, and sulfonamide.

* * * * *